(12) United States Patent
Terliuc et al.

(10) Patent No.: US 9,119,532 B2
(45) Date of Patent: Sep. 1, 2015

(54) ASSEMBLIES FOR USE WITH AN ENDOSCOPE

(75) Inventors: Gad Terliuc, Ra'anana (IL); Gilad Luria, Givataim (IL); Ori Nissan, Ramat Gan (IL)

(73) Assignee: SMART MEDICAL SYSTEMS LTD., Ra'anana (IL)

( * ) Notice: Subject to any disclaimer, the term of this patent is extended or adjusted under 35 U.S.C. 154(b) by 860 days.

(21) Appl. No.: 12/934,775

(22) PCT Filed: Mar. 23, 2009

(86) PCT No.: PCT/IL2009/000322
§ 371 (c)(1),
(2), (4) Date: Dec. 10, 2010

(87) PCT Pub. No.: WO2009/122395
PCT Pub. Date: Oct. 8, 2009

(65) Prior Publication Data
US 2011/0105840 A1    May 5, 2011

Related U.S. Application Data

(60) Provisional application No. 61/064,881, filed on Mar. 31, 2008.

(51) Int. Cl.
  *A61B 1/32* (2006.01)
  *A61B 1/00* (2006.01)
  *A61B 1/04* (2006.01)
(52) U.S. Cl.
  CPC ......... *A61B 1/00131* (2013.01); *A61B 1/00082* (2013.01); *A61B 1/00101* (2013.01); *A61B 1/00135* (2013.01)
(58) Field of Classification Search
  USPC ........ 29/727, 890.043, 890.044; 72/120–123; 606/205, 191, 198; 600/121–125, 127, 600/129, 201, 210–217, 219, 224, 225, 101, 600/12
  See application file for complete search history.

(56) References Cited

U.S. PATENT DOCUMENTS

| 4,040,413 A | 8/1977 | Ohshiro |
| 4,066,070 A | 1/1978 | Utsugi |

(Continued)

FOREIGN PATENT DOCUMENTS

| JP | 2003-250896 A | 9/2003 |
| WO | 83/01893 A1 | 6/1983 |

(Continued)

OTHER PUBLICATIONS

Olympus; "Single Balloon Enteroscope System", Single Balloon Endoscope product, including SIF-Q 180 enteroscope, ST-SB1 overtube, which interface with balloon pump control OBCU and EVIS EXERA II system video system all commercially available from Olympus Inc., of 3500 Corporate Parkway Center Valley, PA 18034-0610, USA.

(Continued)

*Primary Examiner* — Ryan Henderson
(74) *Attorney, Agent, or Firm* — Ladas & Parry LLP

(57) ABSTRACT

An expander for mounting a resilient outer tubular article over an elongate article including a chassis element having associated therewith at least one outwardly movable element which is selectably engageable with at least a portion of the resilient outer tubular article, a driver which is movable with respect to the chassis element and is operative to selectably engage the at least one outwardly movable element, when the outwardly movable element is in engagement with the at least a portion of the resilient outer tubular article, for producing corresponding outward motion and outward expansion thereof and an engagement element, associated with the driver, for insertion into the at least a portion of the resilient outer tubular article upon expansion thereof by operation of the driver, the engagement element being configured to accommodate at least a portion of the elongate article.

8 Claims, 45 Drawing Sheets

(56) References Cited

U.S. PATENT DOCUMENTS

| | | | |
|---|---|---|---|
| 4,148,307 | A | 4/1979 | Utsugi |
| 4,176,662 | A | 12/1979 | Frazer |
| 4,195,633 | A | 4/1980 | Nehring et al. |
| 4,195,637 | A | 4/1980 | Gruntzig et al. |
| 4,224,929 | A | 9/1980 | Furihata |
| 4,445,892 | A | 5/1984 | Hussein et al. |
| 4,453,545 | A | 6/1984 | Inoue |
| 4,616,652 | A | 10/1986 | Simpson |
| 4,646,722 | A | 3/1987 | Silverstein et al. |
| 4,646,988 | A | 3/1987 | Campbell |
| 4,676,228 | A | 6/1987 | Krasner et al. |
| 4,690,131 | A | 9/1987 | Lyddy, Jr. et al. |
| 4,807,593 | A | 2/1989 | Ito |
| 4,862,874 | A | 9/1989 | Kellner |
| 4,983,165 | A | 1/1991 | Loiterman |
| 5,025,778 | A | 6/1991 | Silverstein et al. |
| 5,050,585 | A | 9/1991 | Takahashi |
| 5,135,001 | A | 8/1992 | Sinofsky et al. |
| 5,144,848 | A | 9/1992 | Uenishi et al. |
| 5,152,277 | A | 10/1992 | Honda et al. |
| 5,259,366 | A | 11/1993 | Reydel et al. |
| 5,398,670 | A | 3/1995 | Ortiz et al. |
| 5,518,501 | A | 5/1996 | Oneda et al. |
| 5,575,797 | A | 11/1996 | Neubauer et al. |
| 5,577,992 | A | 11/1996 | Chiba et al. |
| 5,662,587 | A | 9/1997 | Grundfest et al. |
| 5,679,110 | A | 10/1997 | Hamazaki |
| 5,762,604 | A | 6/1998 | Kieturakis |
| 5,876,329 | A | 3/1999 | Harhen |
| 5,904,657 | A | 5/1999 | Unsworth et al. |
| 5,938,586 | A | 8/1999 | Wilk et al. |
| 5,944,657 | A * | 8/1999 | Djurovic ............... 600/218 |
| 6,007,482 | A | 12/1999 | Madni et al. |
| 6,161,049 | A | 12/2000 | Rudie et al. |
| 6,162,171 | A | 12/2000 | Ng et al. |
| 6,309,346 | B1 | 10/2001 | Farhadi |
| 6,461,294 | B1 | 10/2002 | Oneda et al. |
| 6,485,409 | B1 | 11/2002 | Voloshin et al. |
| 6,585,639 | B1 | 7/2003 | Kotmel et al. |
| 6,663,589 | B1 | 12/2003 | Halevy |
| 6,702,735 | B2 | 3/2004 | Kelly |
| 6,939,291 | B2 | 9/2005 | Phee Soo Jay et al. |
| 6,951,554 | B2 | 10/2005 | Johansen et al. |
| 6,988,986 | B2 | 1/2006 | Gross |
| 7,056,284 | B2 | 6/2006 | Martone et al. |
| 7,169,105 | B2 | 1/2007 | Iwasaka et al. |
| 7,798,992 | B2 | 9/2010 | Ortiz |
| 2001/0018596 | A1* | 8/2001 | Selmon et al. ............ 606/198 |
| 2002/0143237 | A1 | 10/2002 | Oneda et al. |
| 2002/0156347 | A1 | 10/2002 | Kim et al. |
| 2003/0032975 | A1* | 2/2003 | Bonutti .................. 606/192 |
| 2003/0065250 | A1 | 4/2003 | Chiel et al. |
| 2004/0102681 | A1 | 5/2004 | Gross |
| 2005/0038319 | A1 | 2/2005 | Goldwasser et al. |
| 2005/0038335 | A1 | 2/2005 | Gross et al. |
| 2005/0059931 | A1 | 3/2005 | Garrison et al. |
| 2005/0124856 | A1 | 6/2005 | Fujikura et al. |
| 2005/0125005 | A1 | 6/2005 | Fujikura |
| 2005/0133453 | A1 | 6/2005 | Woodruff et al. |
| 2005/0137457 | A1 | 6/2005 | Machida |
| 2005/0159645 | A1 | 7/2005 | Bertolero et al. |
| 2005/0165233 | A1 | 7/2005 | Hamedi et al. |
| 2005/0165273 | A1 | 7/2005 | Takano |
| 2005/0273021 | A1 | 12/2005 | Burgermeister |
| 2006/0111610 | A1 | 5/2006 | Machida |
| 2006/0161044 | A1 | 7/2006 | Oneda et al. |
| 2006/0241345 | A1 | 10/2006 | Oishi et al. |
| 2007/0244361 | A1 | 10/2007 | Ikeda et al. |

FOREIGN PATENT DOCUMENTS

| | | |
|---|---|---|
| WO | 99/53827 A1 | 10/1999 |
| WO | 02/064028 A1 | 8/2002 |
| WO | 03/080155 A1 | 10/2003 |
| WO | 2004/101059 A1 | 11/2004 |
| WO | 2009/122395 A2 | 10/2009 |

OTHER PUBLICATIONS

Fujinon-Fujifilm; "Double Balloon Endoscopy System", Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, New Jersey, USA.

Sleeve Expander Tool product, manufactured by Hellermann Tyton of 7930 N. Faulkner Road., Milwaukee, Wisconsin USA and commercially distributed in the UK by Canford Audio PLC of Crowther Road, Washington, UK under catalog No. 55-601.

An Office Action dated Mar. 23, 2009 which issued during the prosecution of Applicant's Israel Patent Application No. 177148. (Including a translation of the relevant part).

An Office Action dated Sep. 23, 2009, which issued during the prosecution of Applicant's Israel Patent Application No. 177148. (Including a translation of the relevant part).

USPTO OA mailed Feb. 11, 2011 in connection with U.S. Appl. No. 11/980,046.

USPTO NOA mailed Feb. 24, 2011 in connection with U.S. Appl. No. 11/980,025.

USTPO OA mailed Sep. 2, 2010 in connection with U.S. Appl. No. 11/980,025.

USPTO OA mailed Sep. 8, 2010 in connection with U.S. Appl. No. 11/980,046.

An Office Action dated Sep. 28, 2009, which issued during the prosecution of Applicant's Australian Patent Application No. 2005211257.

USPTO OA mailed Oct. 9, 2009 in connection with U.S. Appl. No. 10/588,131.

USPTO OA mailed Apr. 9, 2010 in connection with U.S. Appl. No. 10/588,131.

An Office Action dated Nov. 3, 2007, which issued during the prosecution of Applicant's Chinese Patent Application No. 200580004311.4.

An Office Action dated Jan. 25, 2010, which issued during the prosecution of Applicant's Chinese Patent Application No. 200810173921.2.

An ISR dated Sep. 1, 2005, which issued during the prosecution of Applicant's PCT/IL05/00152.

An ISR dated Jun. 2, 2010 which issued during the prosecution of Applicant's PCT/IL09/00940.

An ISR dated Sep. 1, 2009 which issued during the prosecution of Applicant's PCT/IL09/00322.

An ISR dated Jul. 9, 2009, which issued during the prosecution of Applicant's PCT/IL08/00687.

An ISR dated Jul. 18, 2008, which issued during the prosecution of Applicant's PCT/IL07/00832.

An ISR dated Apr. 21, 2008, which issued during the prosecution of Applicant's PCT/IL05/00849.

An ISR dated May 19, 2008, which issued during the prosecution of Applicant's PCT/IL07/00600.

An English Translation of an Office Action dated Jul. 3, 2012, which issued during the prosecution of Israel Patent Application No. 208291.

* cited by examiner

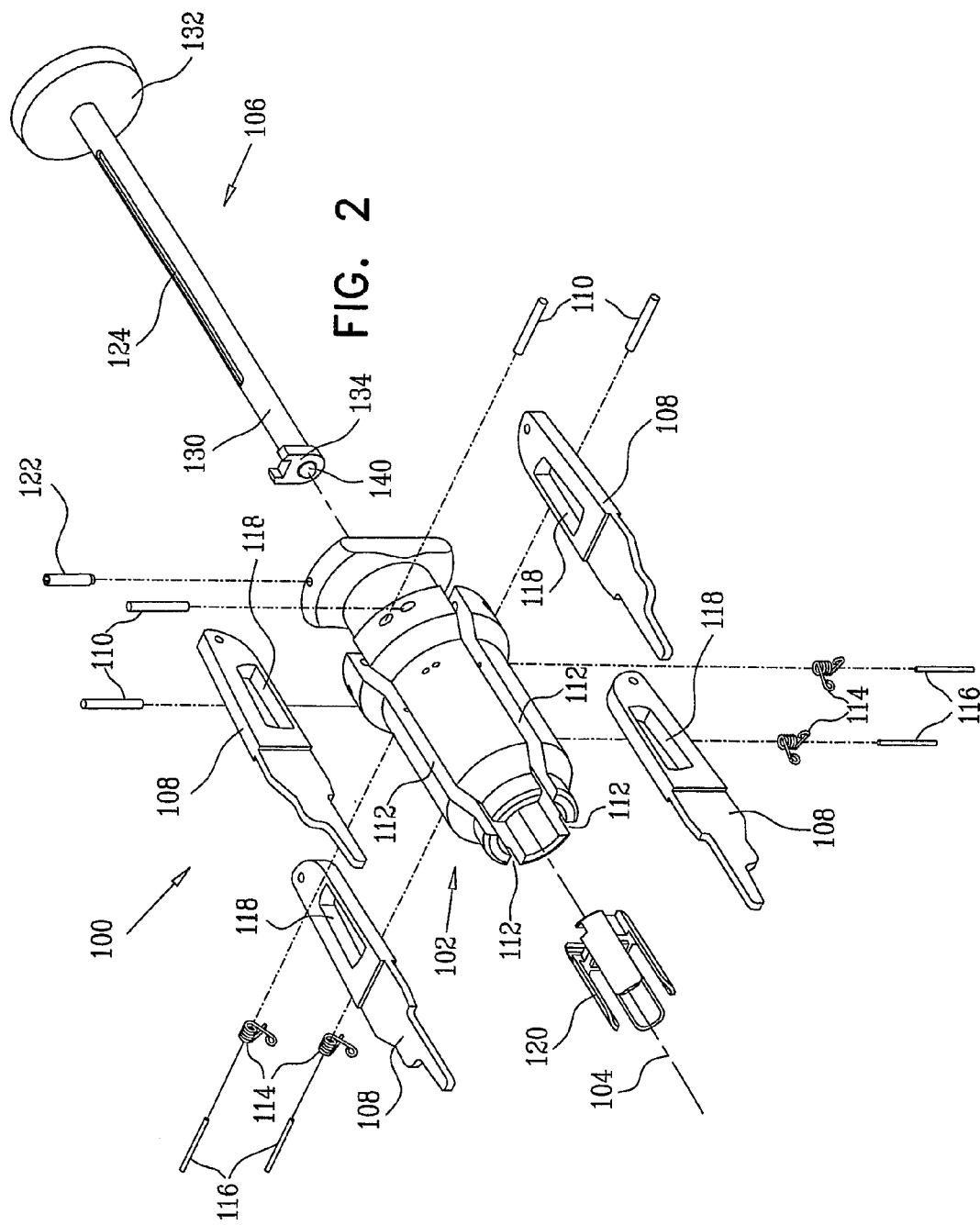

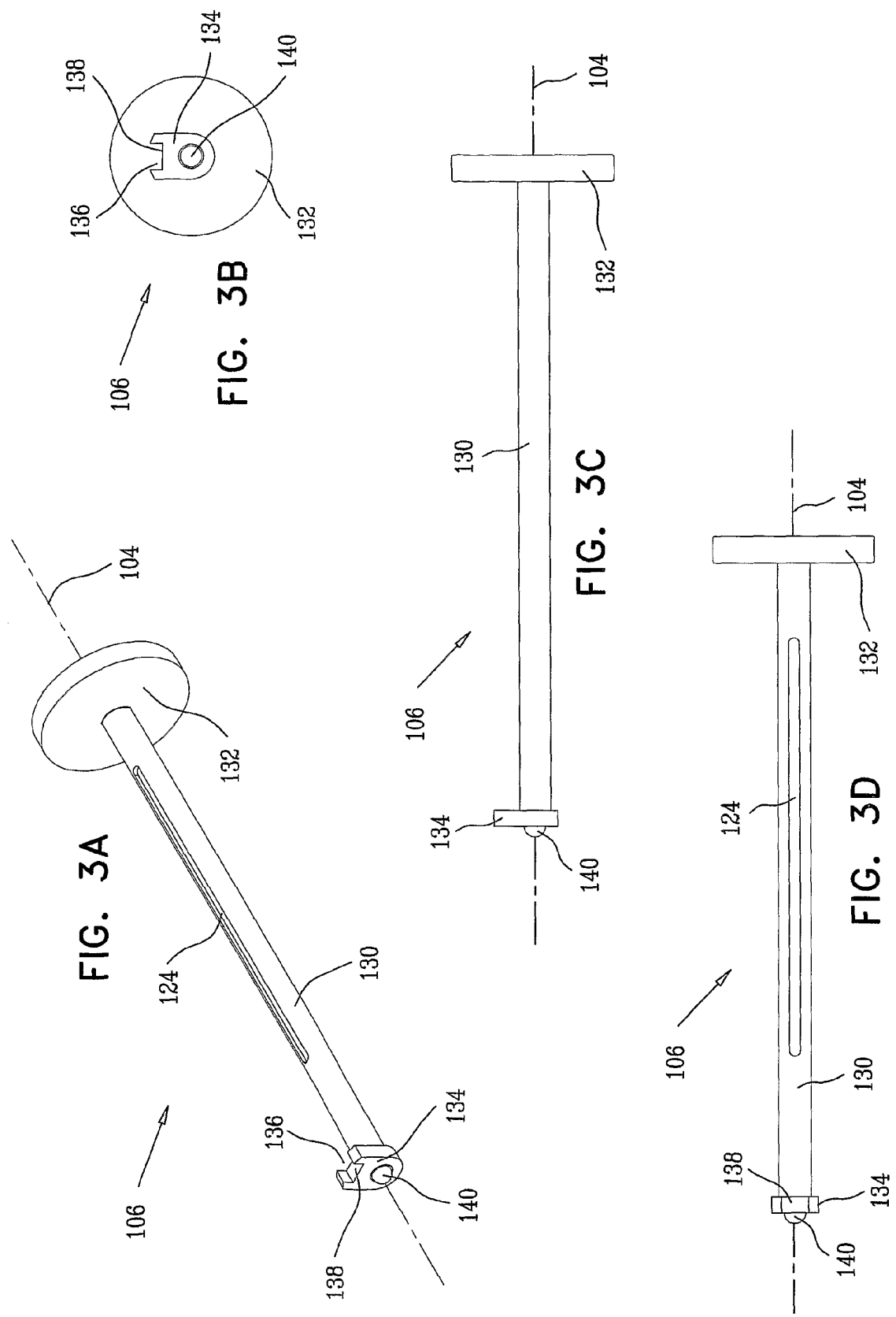

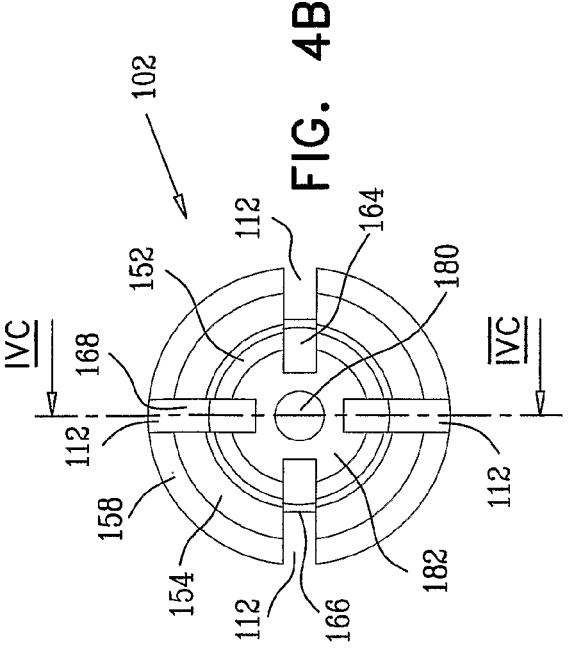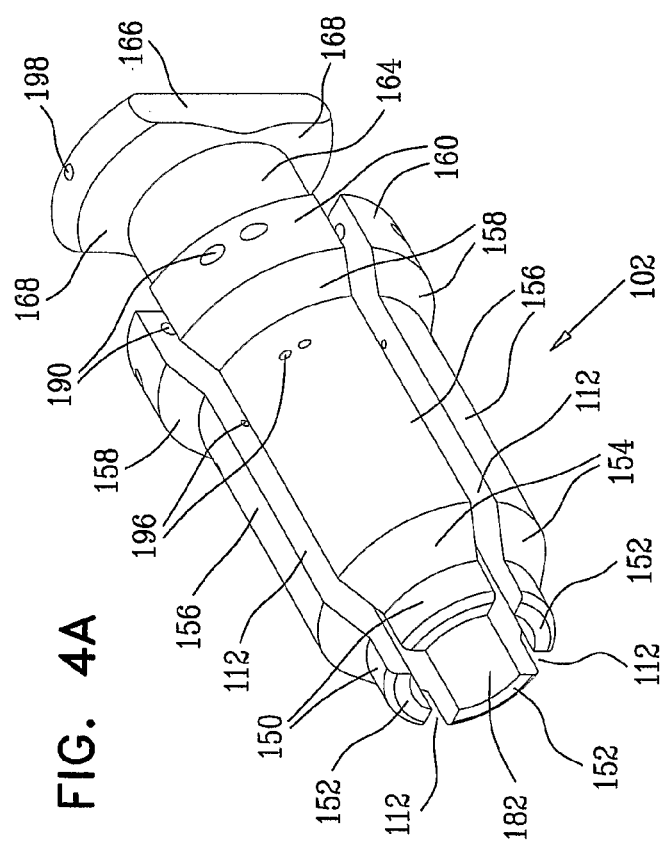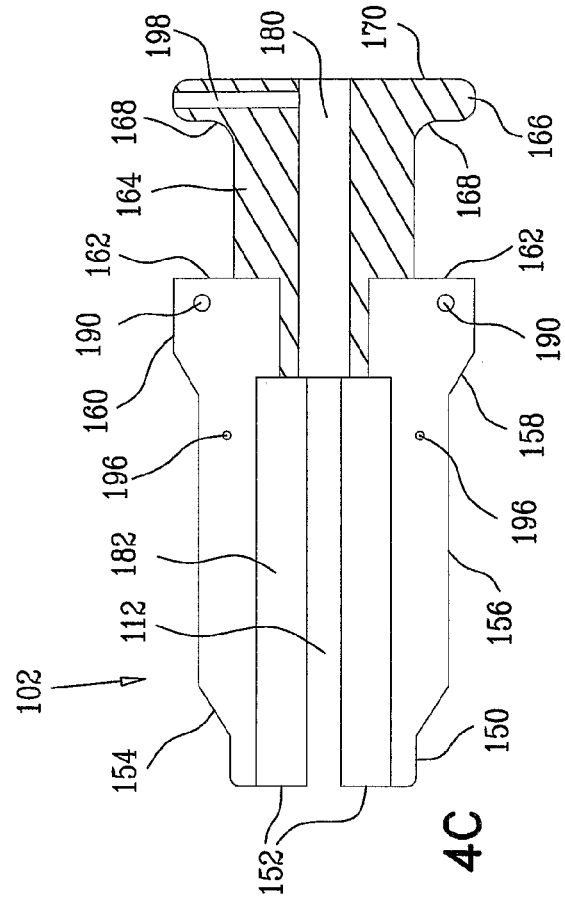

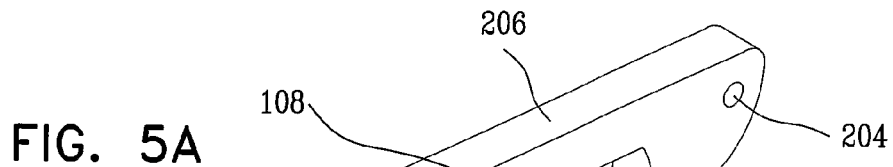
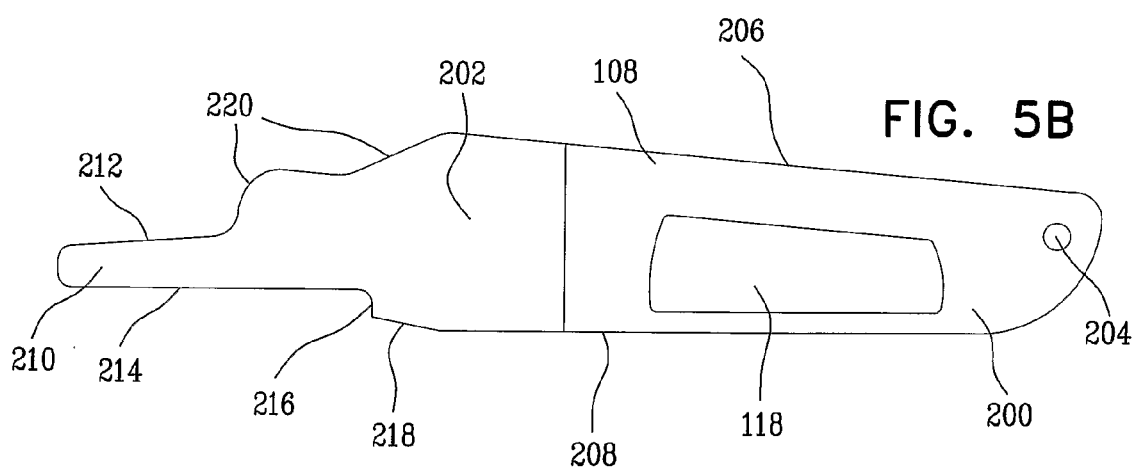
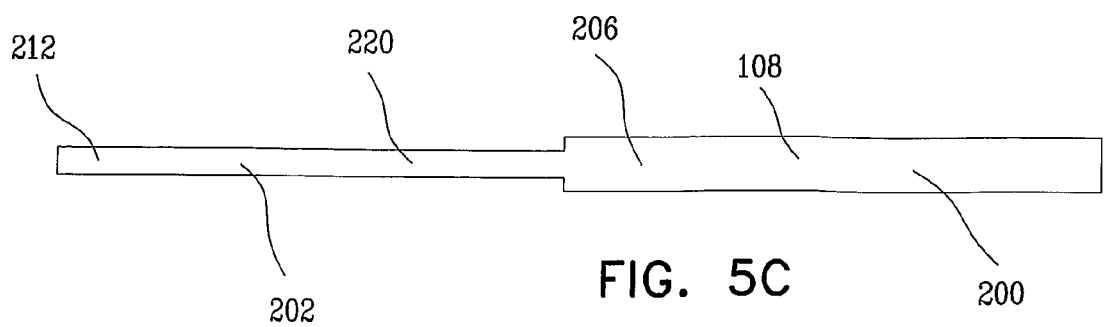

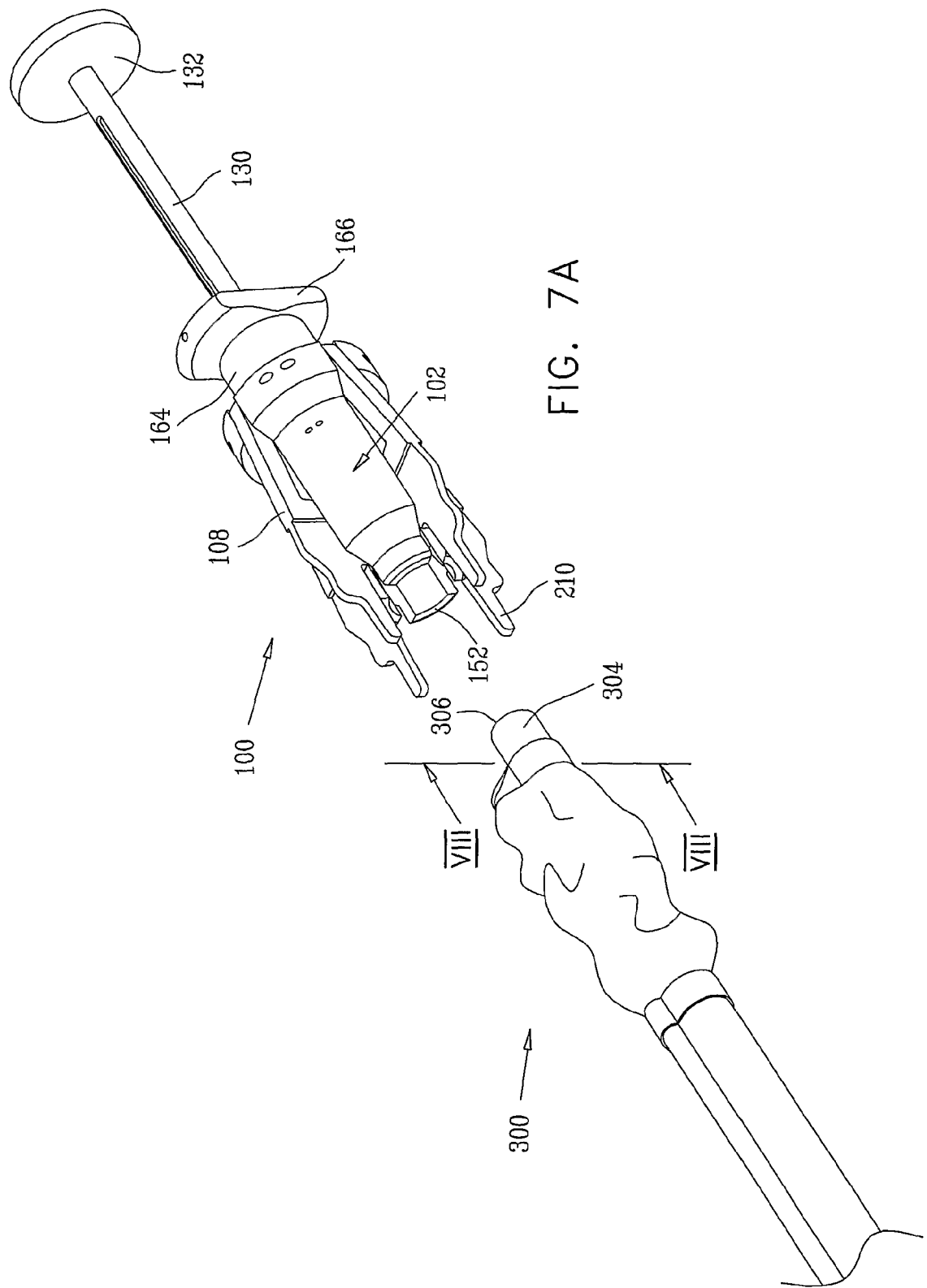

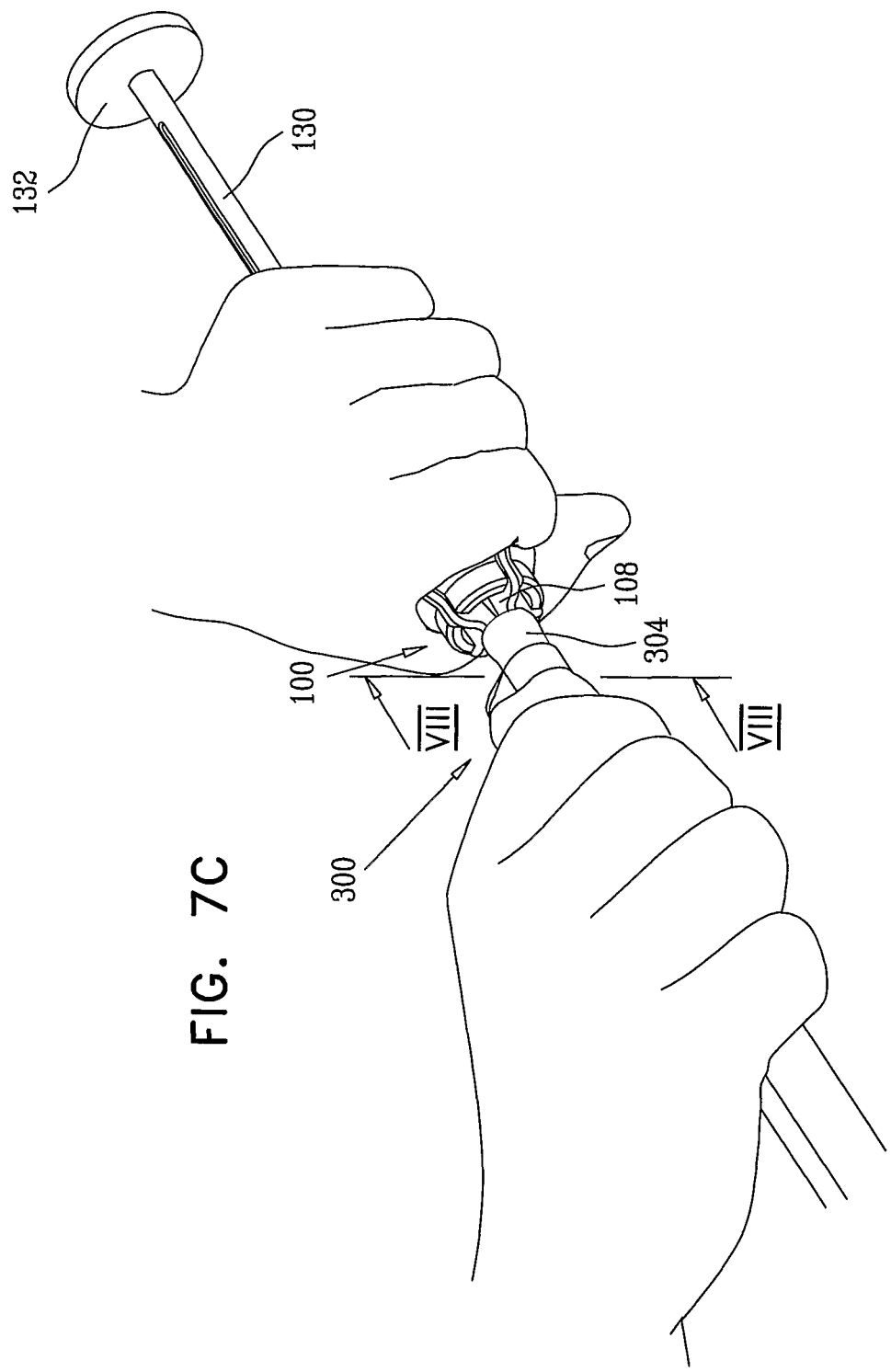

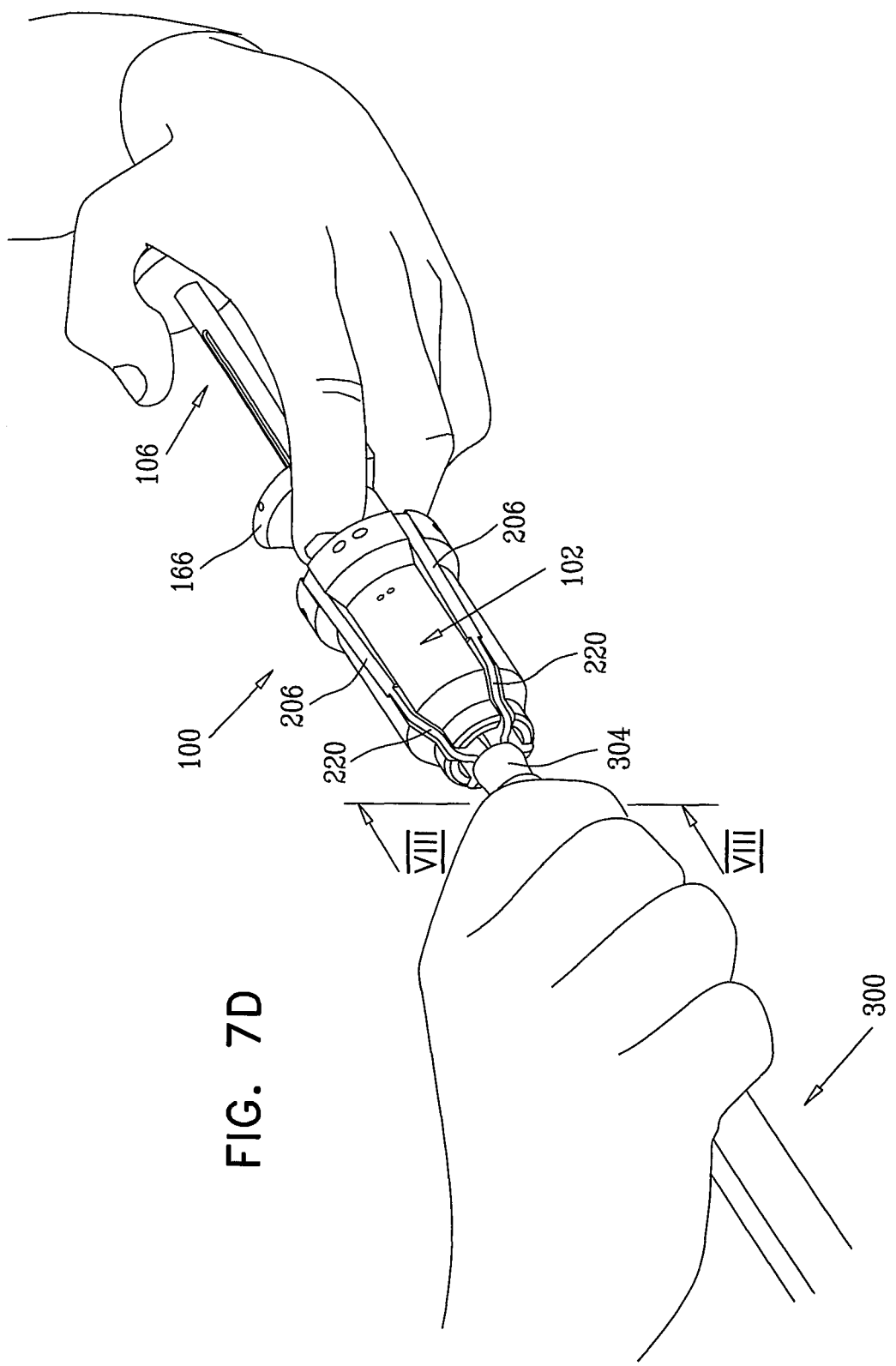

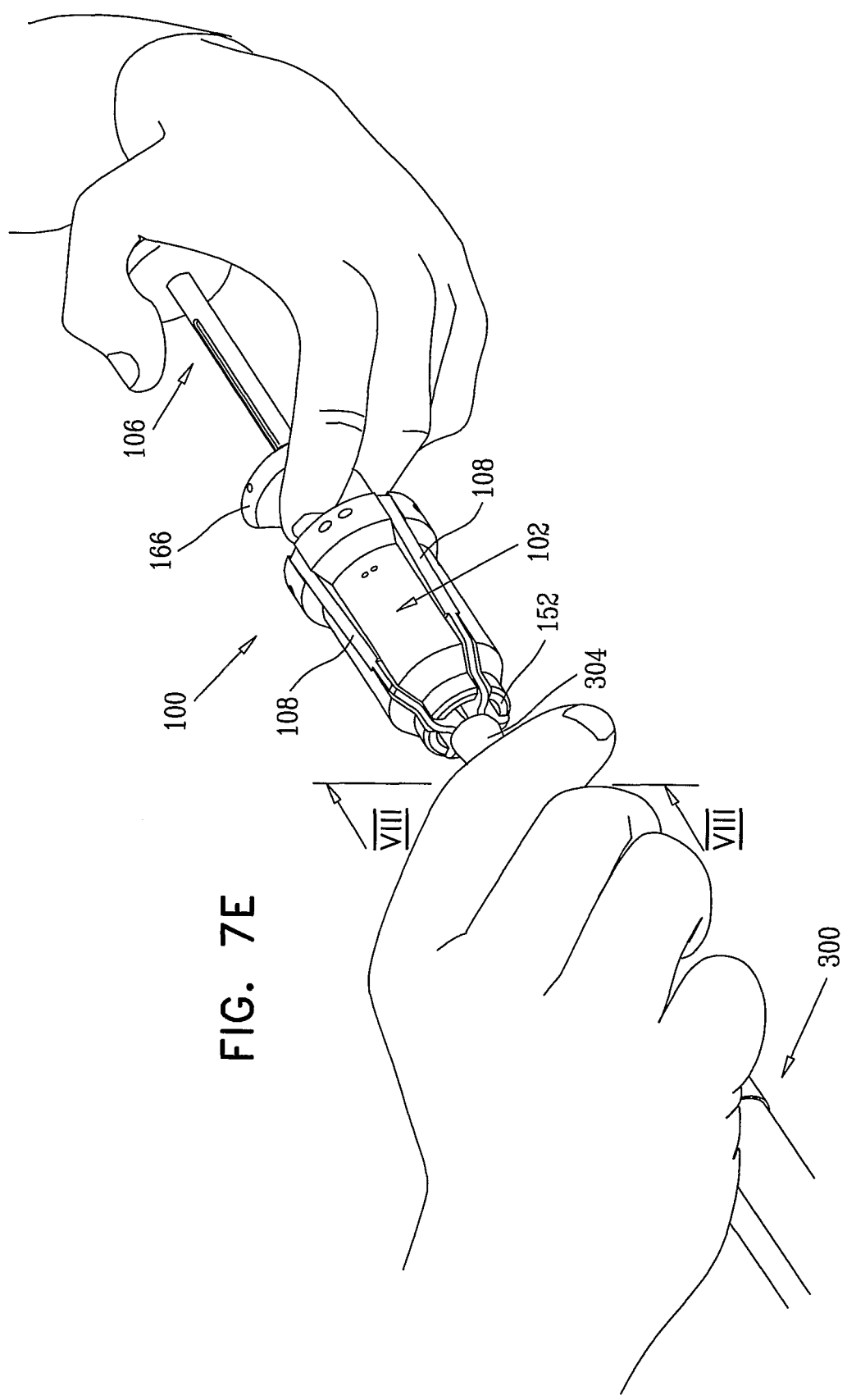

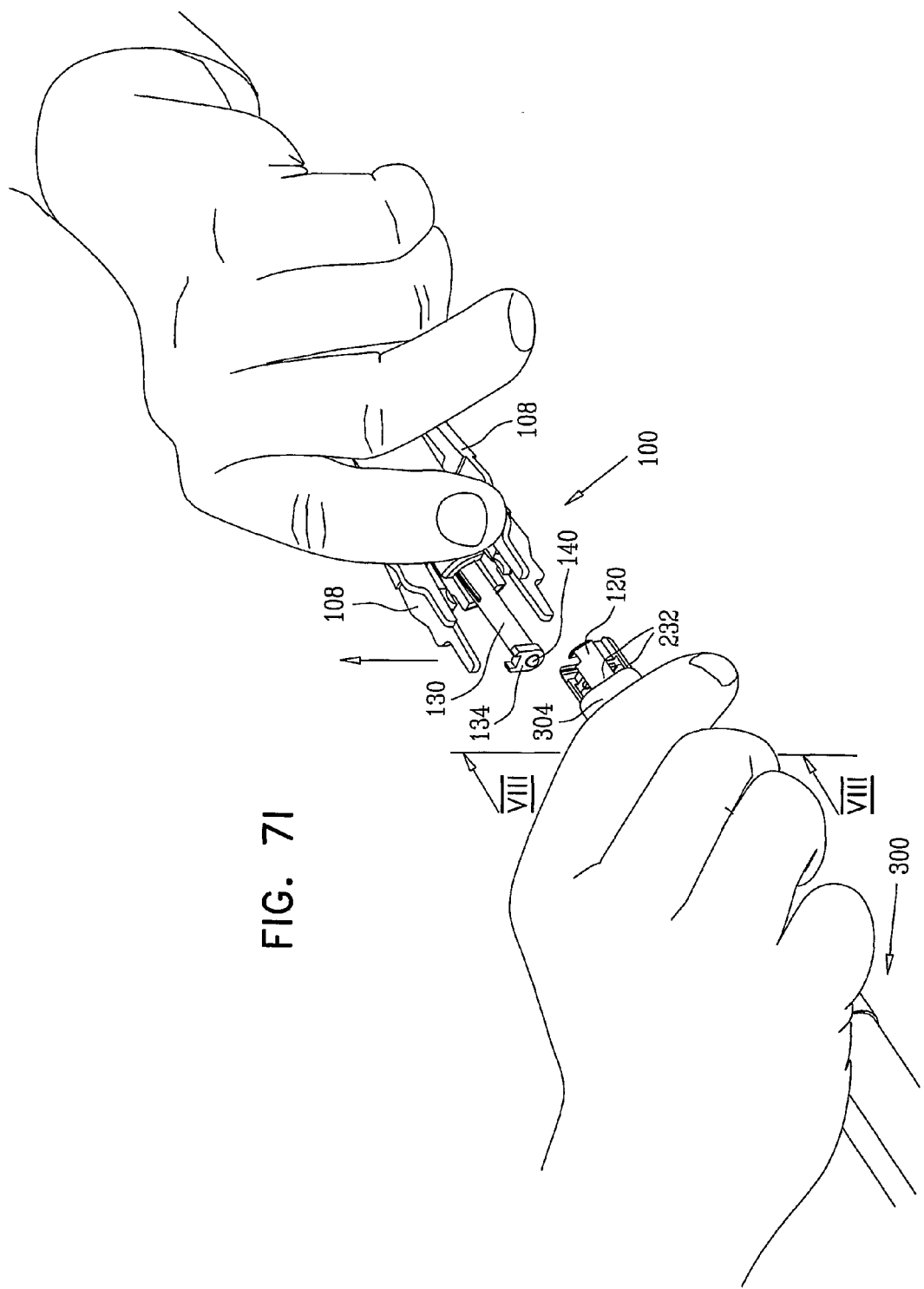

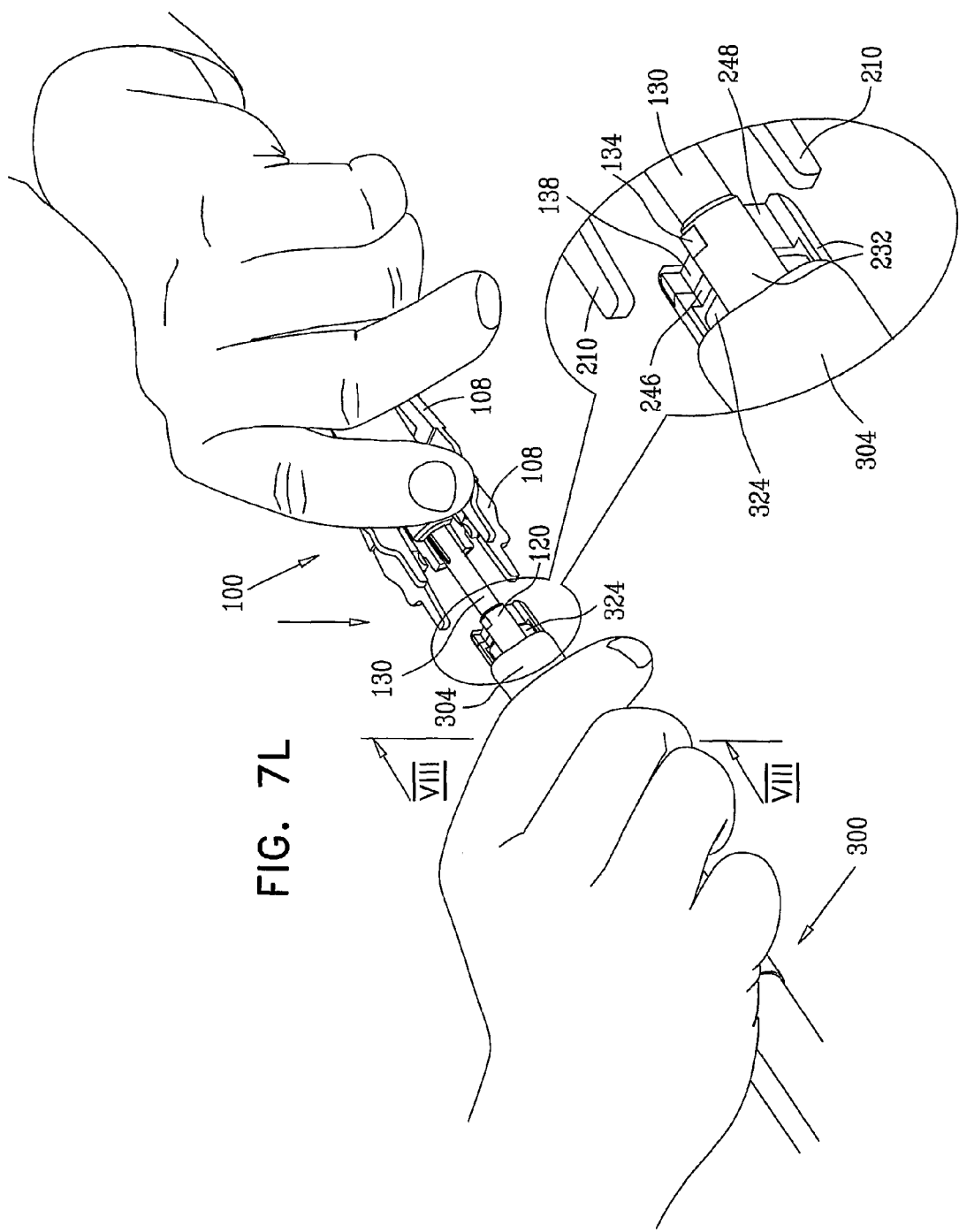

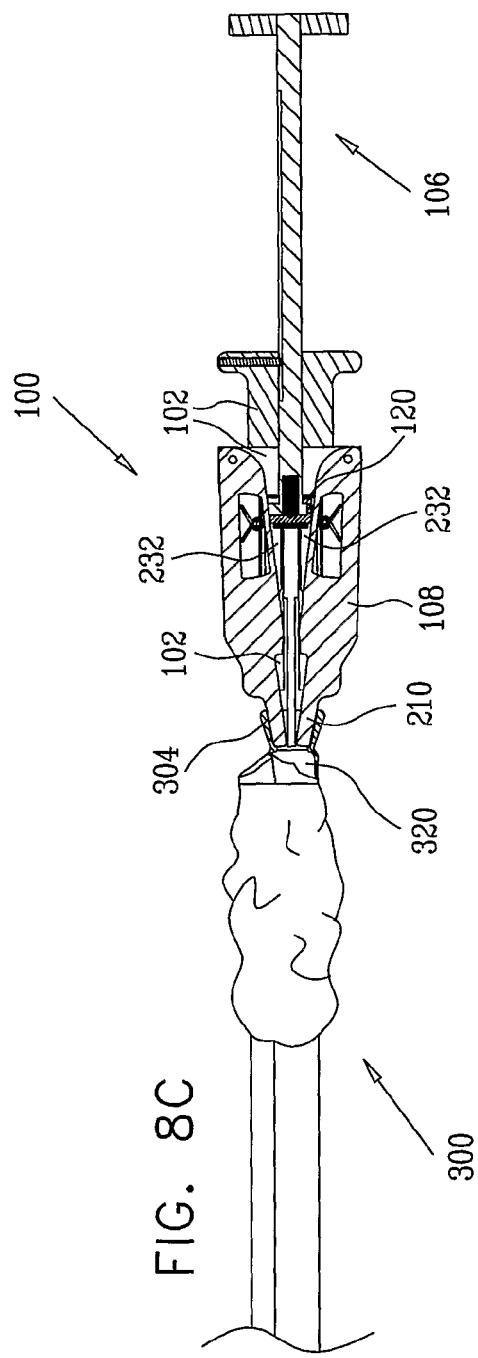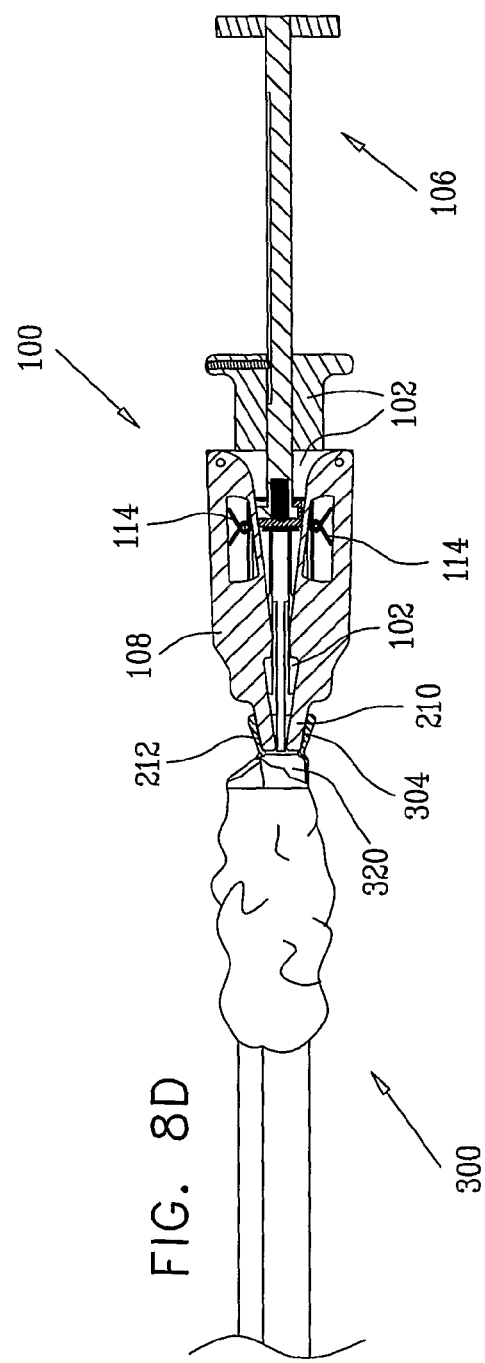

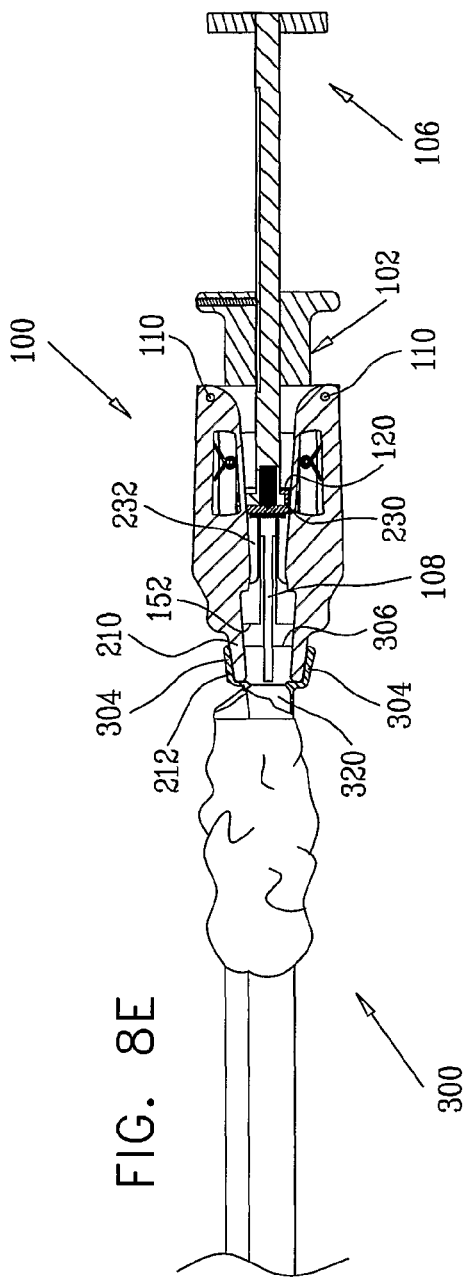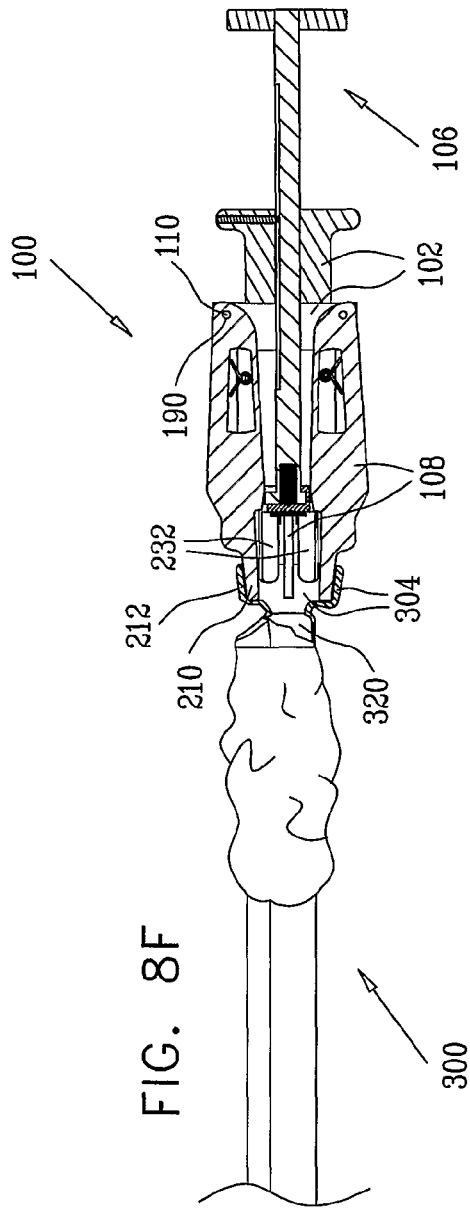

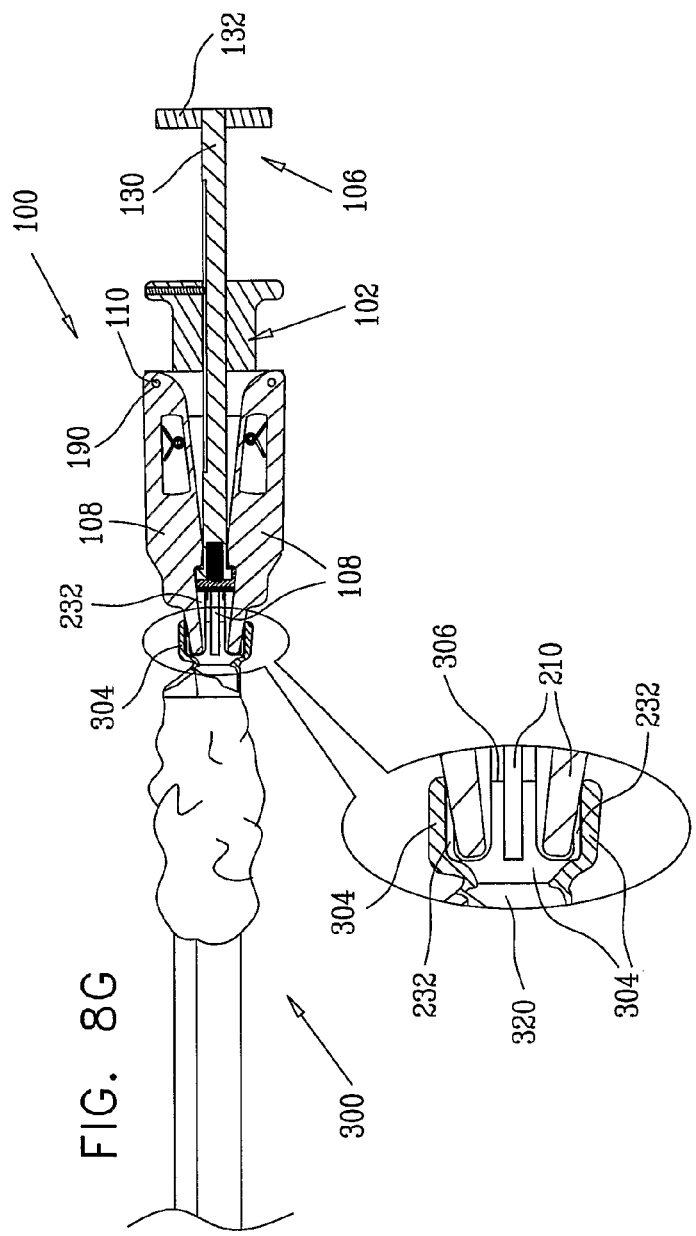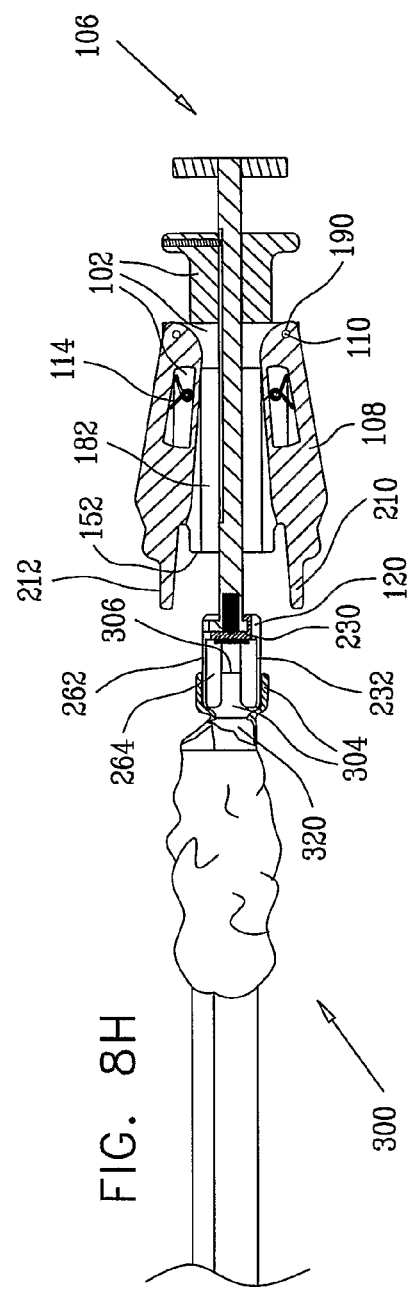
FIG. 8G
FIG. 8H

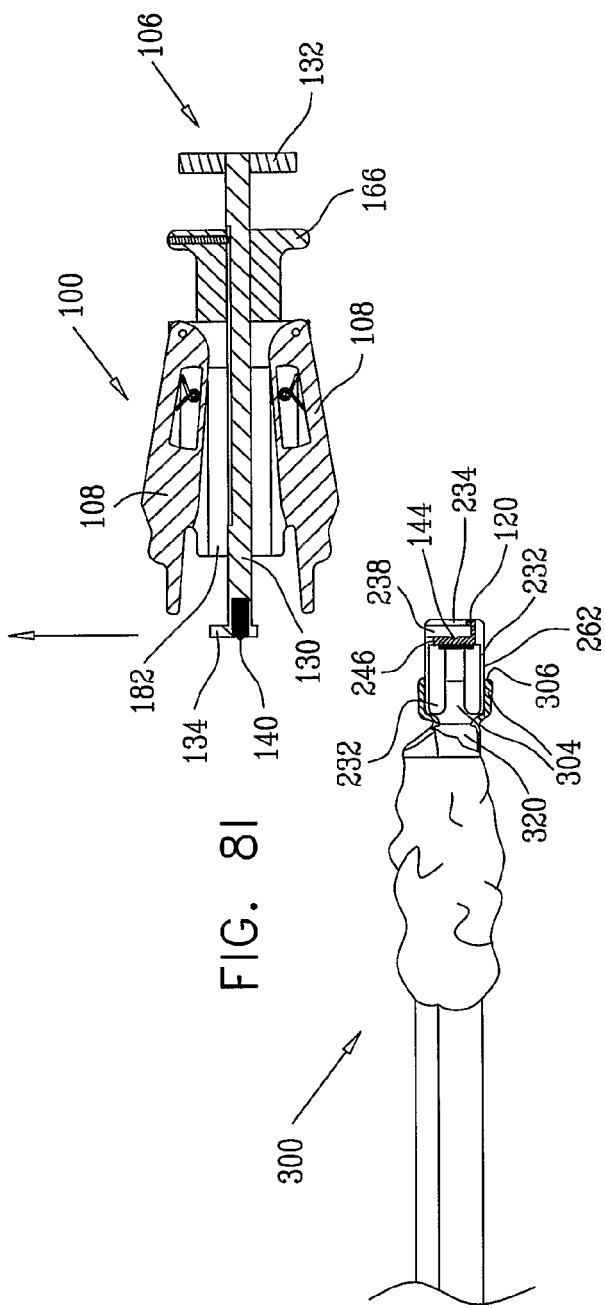
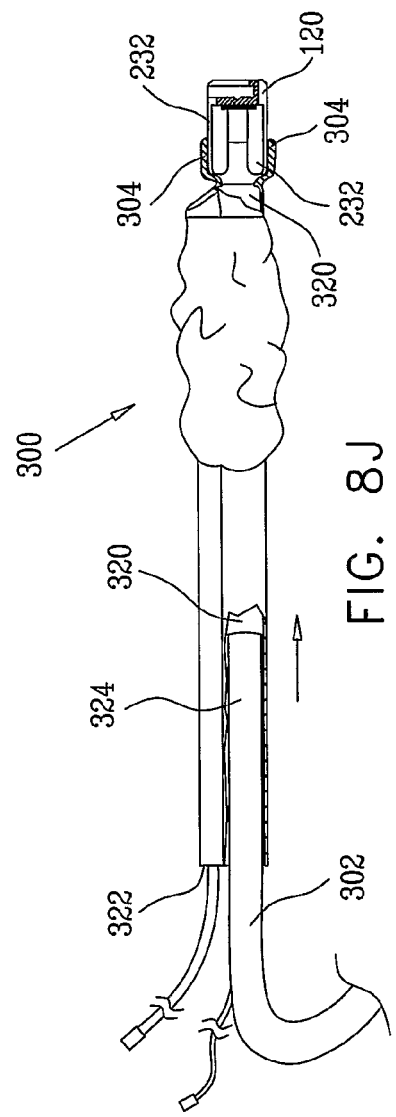
FIG. 8I
FIG. 8J

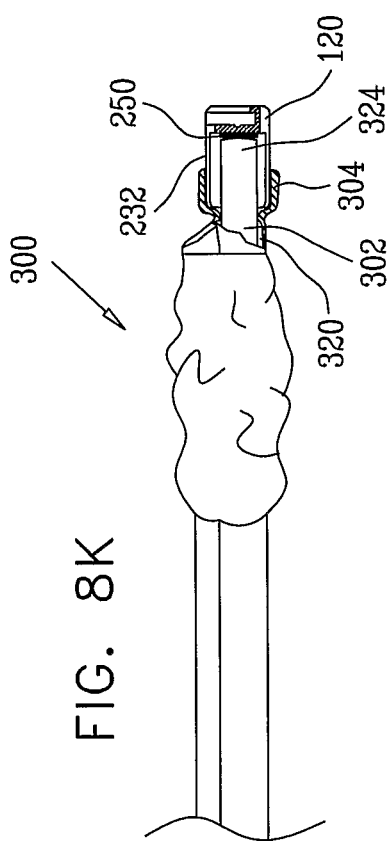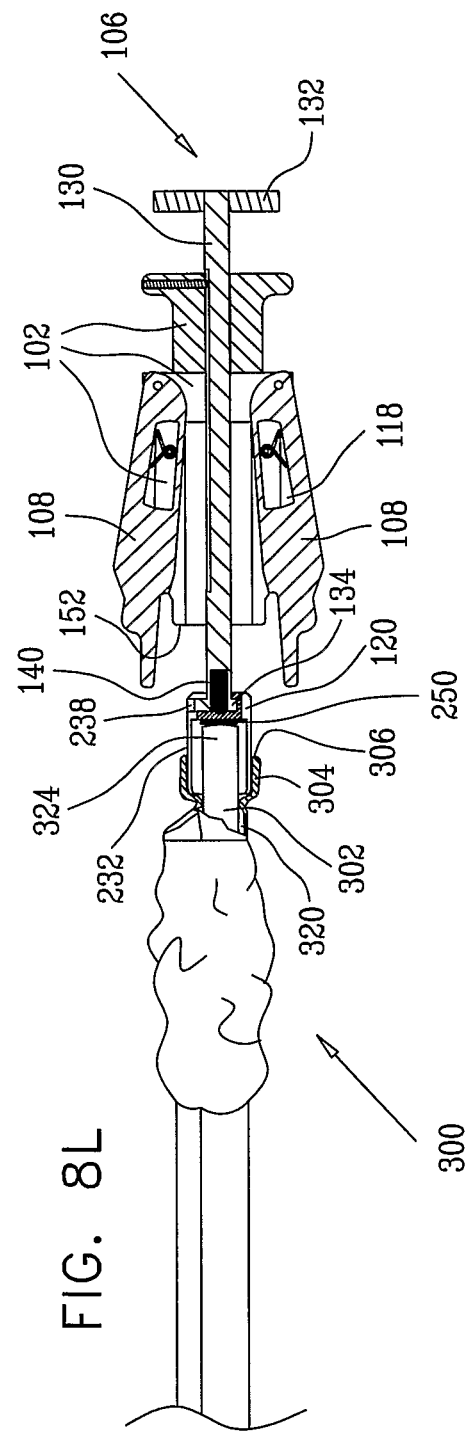

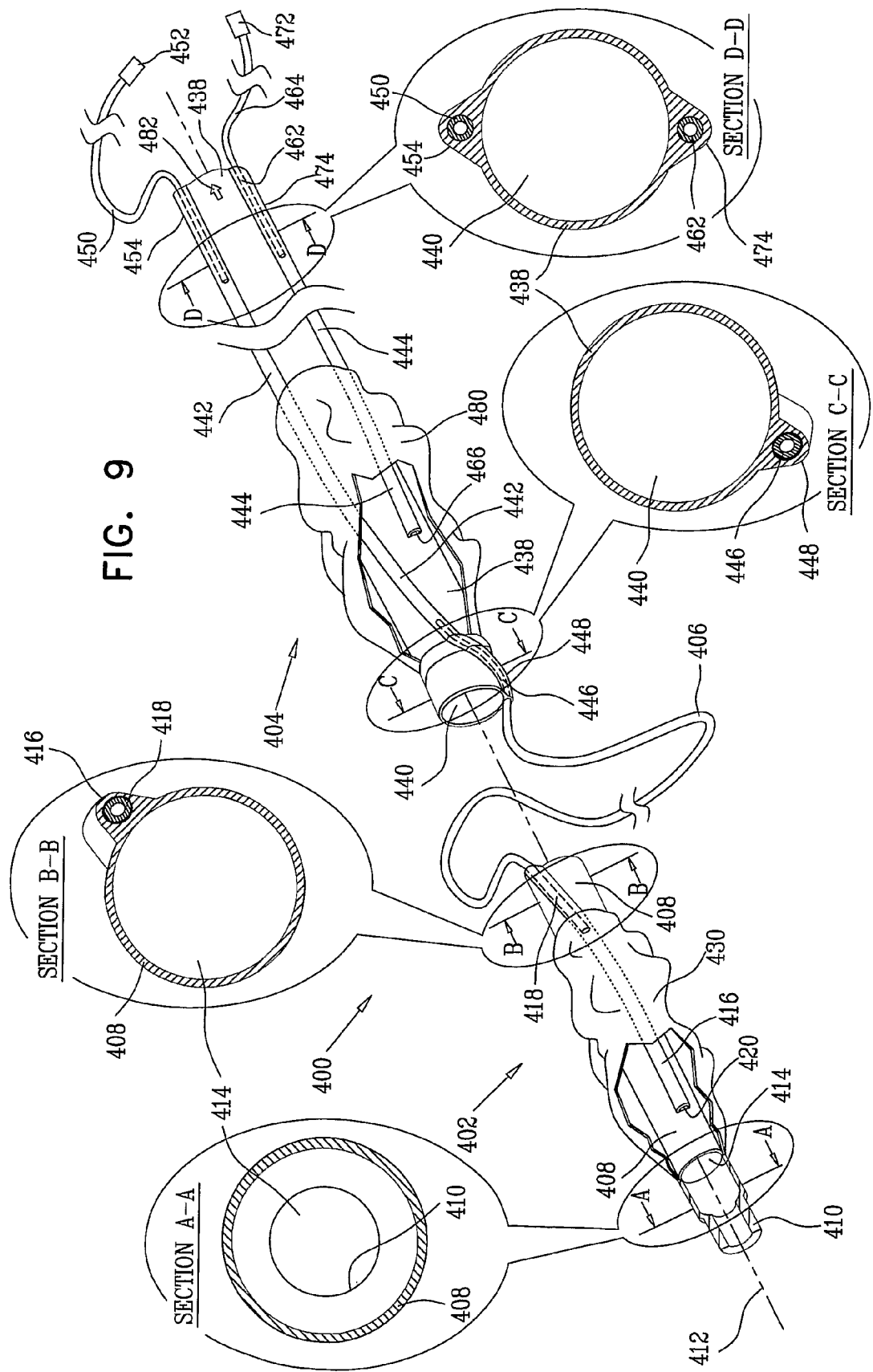

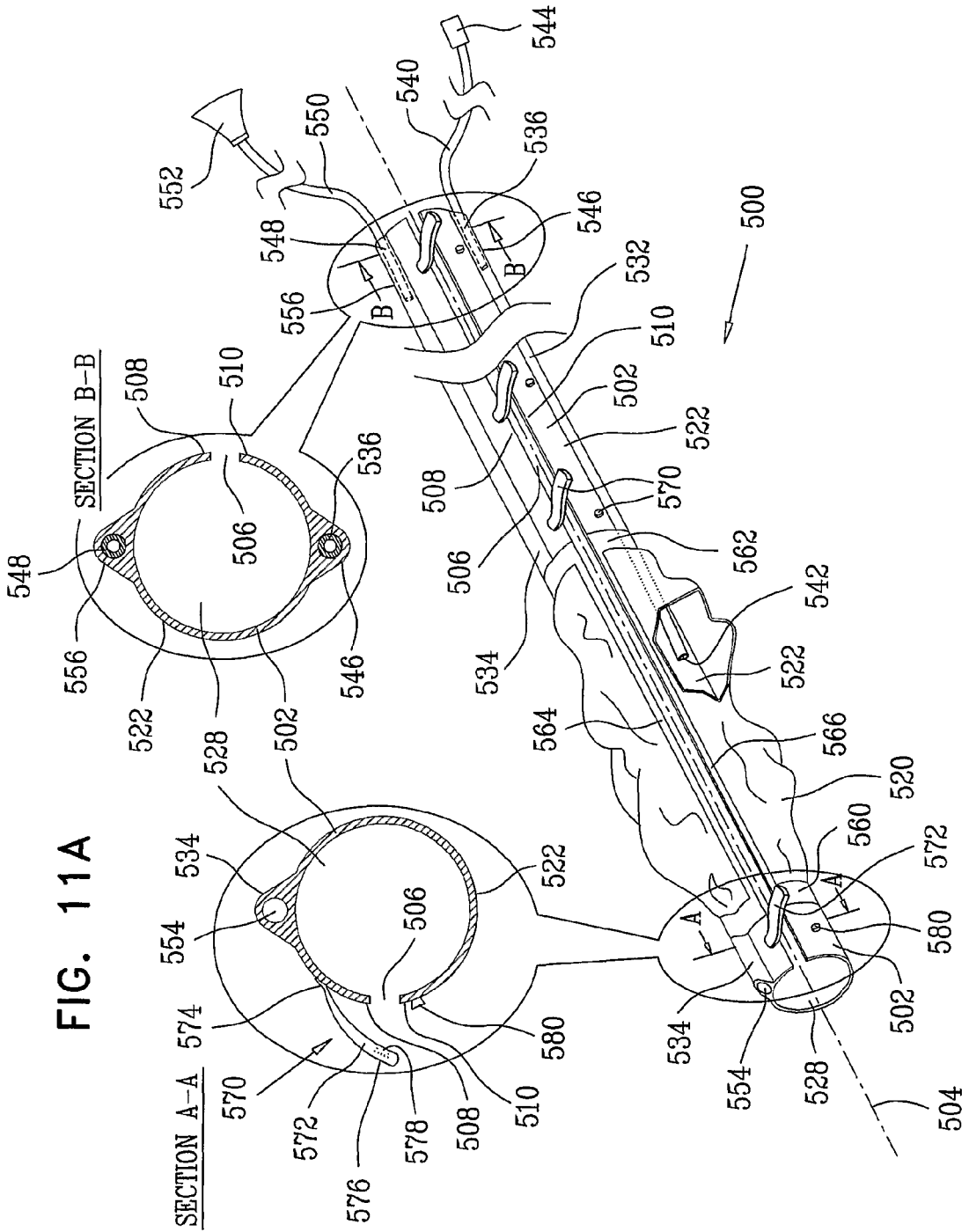

ASSEMBLIES FOR USE WITH AN ENDOSCOPE

REFERENCE TO RELATED APPLICATIONS

Reference is made to the following related application, the disclosure of which is hereby incorporated by reference and priority of which is hereby claimed pursuant to 35 U.S.C. 37 CFR 1.78(a) (4) and (5)(i):

U.S. Provisional Patent Application Ser. No. 61/064,881, filed Mar. 31, 2008, entitled DEVICE AND METHOD FOR EXPANDABLE ELEMENT.

Reference is also made to applicant's copending PCT Application No. PCT/IL2005/000152, filed Feb. 7, 2005; PCT Application No. PCT/IL2005/000849, filed Aug. 8, 2005; PCT Application No. PCT/IL2007/000600, filed May 17, 2007; and PCT Application No. PCT/IL2007/000832, filed Jul. 4, 2007, the disclosures of which are hereby incorporated by reference.

FIELD OF THE INVENTION

The present invention relates to endoscope systems generally.

BACKGROUND OF THE INVENTION

The following patent publications and commercially available products are believed to represent the current state of the art:

U.S. Pat. Nos. 4,040,413; 4,148,307; 4,195,637; 4,453,545; 4,676,228; 4,862,874; 5,025,778; 6,007,482; 6,309,346; 6,461,294; 6,585,639;

U.S. Patent Application publication Nos. 2004/0102681; 2005/0124856; 2005/0125005; 2005/0137457; 2005/0165273; 2006/0111610; 2006/0161044 and 2007/0244361;

Double Balloon Endoscope product, including EN-450T5 enteroscope, TS-13140 overtube and BS-2 front balloon, which interface with balloon pump control BP-20 and 2200 video system, all commercially available from Fujinon Inc., of 10 High Point Drive, Wayne, N.J., USA; and Sleeve Expander Tool product, manufactured by HellermannTyton of 7930N. Faulkner Road, Milwaukee, Wis. USA, and commercially distributed in the UK by Canford Audio PLC of Crowther Road, Wash., UK under catalog number 55-601.

SUMMARY OF THE INVENTION

The present invention seeks to provide improved assemblies for operation with elongate articles such as endoscopes.

There is thus provided in accordance with a preferred embodiment of the present invention an expander for mounting a resilient outer tubular article over an elongate article including a chassis element having associated therewith at least one outwardly movable element which is selectably engageable with at least a portion of the resilient outer tubular article, a driver which is movable with respect to the chassis element and is operative to selectably engage the at least one outwardly movable element, when the outwardly movable element is in engagement with the at least a portion of the resilient outer tubular article, for producing corresponding outward motion and outward expansion thereof and an engagement element, associated with the driver, for insertion into the at least a portion of the resilient outer tubular article upon expansion thereof by operation of the driver, the engagement element being configured to accommodate at least a portion of the elongate article.

In accordance with a preferred embodiment of the present invention the expander also includes resilient outer tubular article disengagement functionality operative for disengagement of the at least a portion of the resilient outer tubular article from the engagement element. Preferably, the disengagement functionality is associated with the chassis element. Additionally or alternatively, the disengagement functionality is operative for sliding the at least a portion of the resilient outer tubular article relative to the engagement element.

Preferably, the expander is operative for mounting the resilient outer tubular article over the elongate article at a generally predetermined distance from a forward end thereof. Additionally or alternatively, the engagement element is removably associated with the driver. Additionally or alternatively, the engagement element is adapted for accommodating the at least a portion of the elongate article up to a predetermined length thereof. Preferably, the engagement element is generally smaller then the chassis element. Yet preferably, the driver is axially movable with respect to the chassis element.

There is also provided in accordance with another preferred embodiment of the present invention a method for mounting a resilient outer tubular article over an elongate article including employing an expander which includes a chassis element which is selectably engageable with at least one resilient portion of the resilient outer tubular article, a driver which is movable with respect to the chassis, and an engagement element configured to accommodate at least a portion of the elongate article, to carry out the functions of expanding the at least one resilient portion of the resilient outer tubular article, followed by insertion of the engagement element into the at least one resilient portion, followed by engagement of the elongate article with the engagement element, followed by disengagement of the engagement element from the at least one resilient portion.

In accordance with a preferred embodiment of the present invention, the method of mounting a resilient outer tubular article over an elongate article also includes, following the insertion of the engagement element into the at least one resilient portion, and prior to engagement of the elongate article with the engagement element, the step of disengagement of the engagement element from the remainder of the expander. Additionally or alternatively, the method also includes following the engagement of the elongate article with the engagement element, and prior to the disengagement of the engagement element from the at least one resilient portion, the step of engagement of the engagement element with the remainder of the expander. Additionally or alternatively, the disengagement of the engagement element from the at least one resilient portion includes sliding the engagement element relative to the at least one resilient portion.

There is further provided in accordance with yet another preferred embodiment of the present invention a hand-held collar cutting tool for removal of an auxiliary endoscope assembly having a resilient collar portion from an endoscope, the cutting tool including a hand-held collar cutting tool body portion, a cutting edge associated with the cutting tool body portion and adapted for cutting the resilient collar portion, and a spacer portion protruding from the hand-held collar cutting tool body portion, the spacer portion being adapted for insertion between the resilient collar portion and the endoscope for spacing the endoscope from the resilient collar portion and from the cutting edge.

In accordance with a preferred embodiment of the present invention, the spacer portion has an elongate, tapered shape. Preferably, the spacer portion has varied flexibility along its length. Additionally or alternatively, the spacer portion is softer than an external surface of the endoscope.

There is also provided in accordance with still another preferred embodiment of the present invention a method for removal of an auxiliary endoscope assembly having a resilient collar portion from an endoscope including employing a hand-held collar cutting tool having a spacer portion and a cutting edge to perform the sequential functions of inserting the spacer portion between the resilient collar portion and the endoscope, thereby spacing the resilient collar portion from the endoscope and spacing the endoscope from the cutting edge, and bringing the cutting edge into cutting engagement with the resilient collar portion when the resilient collar portion and the cutting edge are both spaced from the endoscope, thereby to prevent cutting damage to the endoscope.

There is even further provided in accordance with still another preferred embodiment of the present invention a double-balloon auxiliary endoscope assembly suitable for use with a conventional endoscope, the assembly including a forward balloon subassembly including a forward balloon support sleeve arranged for mounting in a fixed position over the conventional endoscope and having a forward balloon support sleeve mounted, forward balloon inflation lumen extending at least partially along the forward balloon support sleeve, and a forward balloon mounted on the forward balloon support sleeve and together therewith defining a forward inflatable volume which is inflatable via the forward balloon support sleeve mounted, forward balloon inflation lumen, an overtube subassembly including an overtube sleeve arranged for slidable mounting over the conventional endoscope, and an overtube balloon mounted on the overtube sleeve and together therewith defining a rearward inflatable volume, and the overtube sleeve having first and second lumens extending at least partially therealong, the first lumen being an overtube mounted, forward balloon inflation lumen, and the second lumen being an overtube mounted, overtube balloon inflation lumen, the rearward inflatable volume being inflatable via the overtube mounted, overtube balloon inflation lumen, and an overtube rearward displacement accommodating, flexible interconnection tube interconnecting the forward balloon support sleeve mounted, forward balloon inflation lumen and the overtube mounted, forward balloon inflation lumen.

Preferably, the interconnection tube is selectably extendible by being at least partially straightened. Additionally or alternatively, the double-balloon auxiliary endoscope assembly also includes a forward balloon inflation/deflation supply and exhaust tube connected to the first lumen and an overtube balloon inflation/deflation supply and exhaust tube connected to the second lumen. Additionally or alternatively, the forward balloon support sleeve includes a resilient collar. Preferably, the forward balloon support sleeve includes a collar which is adapted to fixedly mount the forward balloon support sleeve onto endoscopes of varying outer diameter.

There is also provided in accordance with another preferred embodiment of the present invention a method for mounting a double-balloon auxiliary endoscope assembly over a conventional endoscope, the method including sliding an overtube subassembly over the conventional endoscope, and thereafter sliding over the conventional endoscope, while connected to the overtube subassembly via a flexible interconnection tube, a forward balloon sleeve of a forward balloon subassembly also including a forward balloon fixedly mounted on the forward balloon support sleeve and defining together therewith a forward inflatable volume.

In accordance with a preferred embodiment of the present invention, the method for mounting a double-balloon auxiliary endoscope assembly over a conventional endoscope also includes fixedly and removably mounting the forward balloon support sleeve onto the conventional endoscope. Additionally or alternatively, the method also includes initially stretching and then releasing a resilient collar associated with the forward balloon support sleeve for fixedly and removably mounting of the forward balloon support sleeve onto the conventional endoscope.

There is further provided in accordance with yet another embodiment of the present invention a wrap-around overtube which is side-mountable onto an endoscope without access to an end of the endoscope, the overtube including a generally cylindrical sleeve having relatively high axial rigidity and relatively low radial rigidity, the tube being formed with an expandable generally axial slit, the sleeve being configured to permit circumferential expansion of the slit to an extent sufficient to accommodate an endoscope and subsequent circumferential contraction of the slit to provide wrap-around mounting of the overtube onto the endoscope.

Preferably, the sleeve is configured with respect to the endoscope to permit slidable axial displacement of the sleeve along the endoscope. Additionally or alternatively, the wrap-around overtube also includes a wrap-around balloon mounted over at least a portion of the sleeve, the wrap-around balloon being configured for wrap-around mounting thereof onto the endoscope. Additionally or alternatively, the wrap-around overtube also includes an external tube extending at least partially along the sleeve, the external tube being configured for passage of an endoscope tool therethrough. Preferably, the external tube traverses the balloon. Yet preferably, the external tube includes a low-friction lumen through which the endoscope tool is slidably movable.

There is further provided in accordance with still another preferred embodiment of the present invention a method for mounting an overtube onto an endoscope without access to an end of the endoscope, the method including providing a wrap-around overtube having an expandable generally axial slit, expanding the generally axial slit so as to accommodate the endoscope at a location spaced from an end thereof, placing the overtube, with the generally axial slit expanded, over the endoscope at a location spaced from an end thereof, and at least partially closing the generally axial slit thereby to retain the overtube over the endoscope at the location spaced from the end thereof.

Preferably, the method also includes sliding displacement of the overtube along the endoscope following at least partially closing of the generally axial slit.

There is even further provided in accordance with still another preferred embodiment of the present invention a wrap-around balloon which is side-mountable onto an endoscope without access to an end of the endoscope, the wrap-around balloon including a generally cylindrical balloon being formed with an expandable generally axial slit, the balloon being configured to permit circumferential expansion of the slit to an extent sufficient to accommodate an endoscope and subsequent circumferential contraction of the slit to provide wrap-around mounting of the balloon onto the endoscope.

There is also provided in accordance with yet another preferred embodiment of the present invention a method for mounting a balloon onto an endoscope without access to an end of the endoscope, the method including providing a wrap-around balloon, placing the wrap-around balloon over the endoscope at a location spaced from an end thereof, and retaining the wrap-around balloon over the endoscope.

There is further provided in accordance with still another preferred embodiment of the present invention a slidable external tube assembly for use with an endoscope, including an elongate tube having a lumen, the lumen being configured for passage therethrough of an endoscope tool, and at least one side-mountable element configured for removably and slidably mounting the elongate tube onto the endoscope without requiring access to an end of the endoscope.

Preferably, the elongate tube and the at least one side-mountable element are integrally formed as one piece.

There is also provided in accordance with another preferred embodiment of the present invention a method for slidable mounting of an external tube assembly onto an endoscope, including providing an elongate tube having a lumen, the lumen being configured for passage therethrough of an endoscope tool, employing at least one side mountable element for removably and slidably mounting the elongate tube onto the endoscope without requiring access to an end of the endoscope, and sliding the elongate tube axially relative to the endoscope.

BRIEF DESCRIPTION OF THE DRAWINGS

The present invention will be understood and appreciated from the following detailed description, taken in conjunction with the drawings in which:

FIG. 2 is a simplified exploded view illustration of the device for mounting an auxiliary endoscope assembly onto an endoscope of FIG. 1;

FIGS. 3A, 3B, 3C and 3D are simplified illustrations of a driver assembly forming part of the device of FIGS. 1 & 2;

FIGS. 4A, 4B, 4C, 4D and 4E are simplified illustrations of a flange element forming part of the device of FIGS. 1 & 2;

FIGS. 5A, 5B and 5C are simplified illustrations of an arm element forming part of the device of FIGS. 1 & 2;

FIGS. 7A, 7B, 7C, 7D, 7E, 7F, 7G, 7H, 7I, 7J, 7K, 7L, 7M, 7N, 7O, 7P and 7Q are simplified illustrations of various stages in the operation of the device of FIGS. 1 & 2 for mounting an auxiliary endoscope assembly onto an endoscope, and of various stages in the operation of a collar cutting tool for cutting a collar of an auxiliary endoscope assembly mounted on an endoscope;

FIGS. 8A, 8B, 8C, 8D, 8E, 8F, 8G, 8H, 8I, 8J, 8K, 8L, 8M, 8N, 8O and 8P are sectional illustrations, taken along lines VIII-VIII in FIGS. 1 and 7A-7P, in corresponding FIGS. 7A-7P;

FIG. 9 is a simplified, partially cut away, pictorial illustration of a double balloon device, constructed and operative in accordance with a preferred embodiment of the present invention, which is suitable for mounting on a conventional endoscope;

FIGS. 11A and 11B are simplified pictorial illustrations of an endoscope overtube constructed and operative in accordance with a preferred embodiment of the present invention in respective open and closed orientations;

DETAILED DESCRIPTION OF PREFERRED EMBODIMENTS

Reference is now made to FIGS. 1-6F, which illustrate a device 100 for mounting an auxiliary device, having a resilient, expandable collar portion, such as an auxiliary endoscope assembly (shown in FIGS. 7A-8P) onto an endoscope (shown in FIGS. 7J-7L, 7O-7Q, and 8J-8P), constructed and operative in accordance with a preferred embodiment of the present invention.

The terms "endoscope" and "endoscopy" are used throughout in a manner somewhat broader than their customary meaning and refer to apparatus and methods which operate within body cavities, passageways and the like, such as, for example, the small intestine, the large intestine, arteries and veins. Although these terms normally refer to visual inspection, as used herein they are not limited to applications which employ visual inspection and refer as well to apparatus, systems and methods which need not necessarily involve visual inspection.

Figure 1:
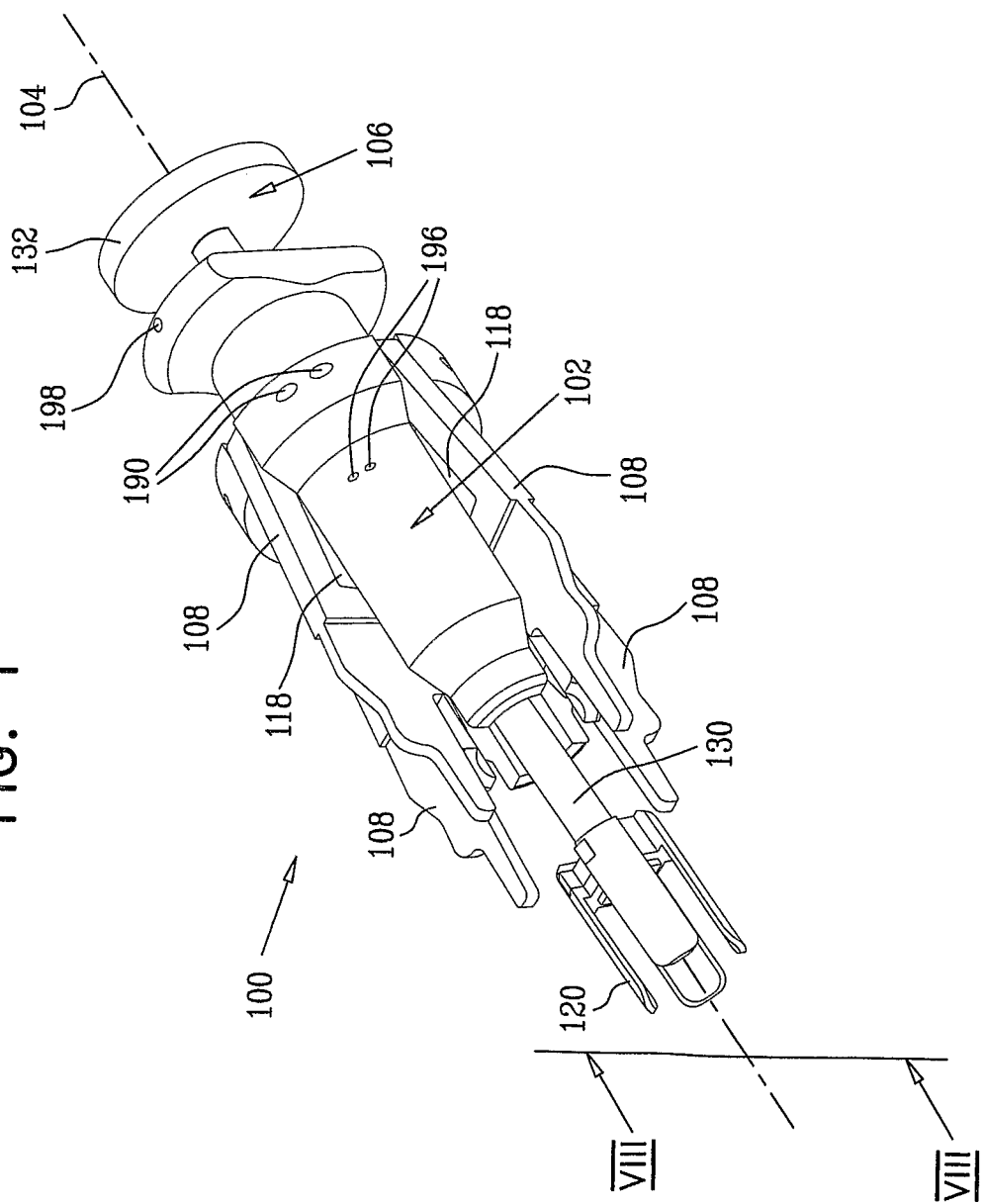
FIG. 1 is a simplified assembled view illustration of a device for mounting an auxiliary endoscope assembly onto an endoscope, constructed and operative in accordance with a preferred embodiment of the present invention.
Figure 4D:
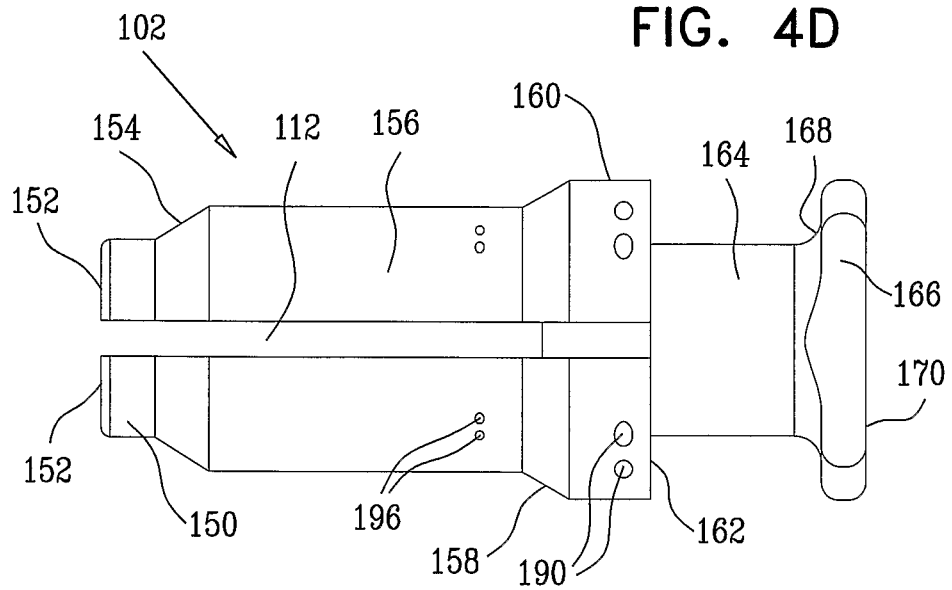
Figure 4E:
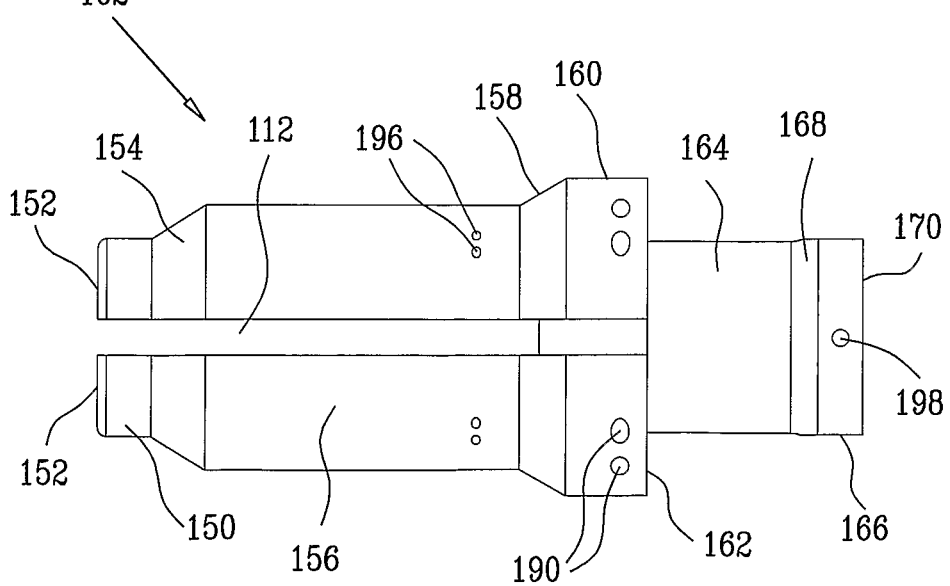
Figure 6A:
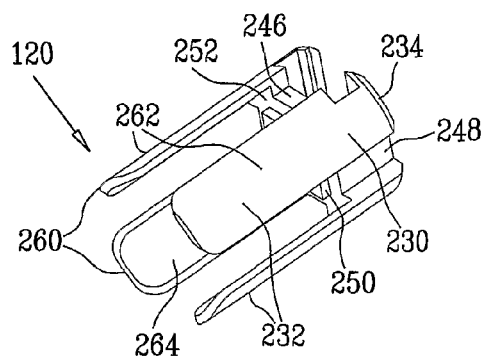
FIGS. 6A, 6B, 6C, 6D, 6E and 6F are simplified illustrations of an axially driven collar engagement element forming part of the device of FIGS. 1 & 2.
Figure 6B:
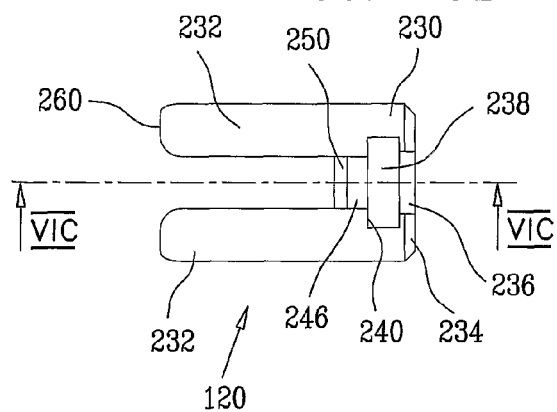
Figure 6C:
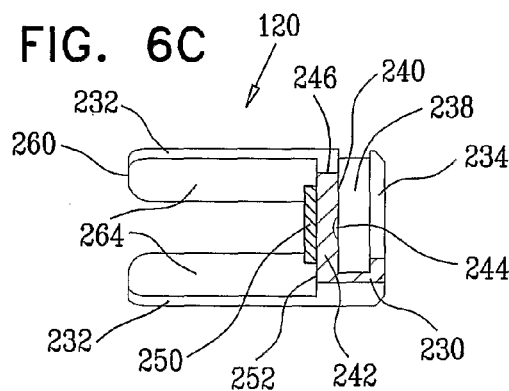
Figure 6D:
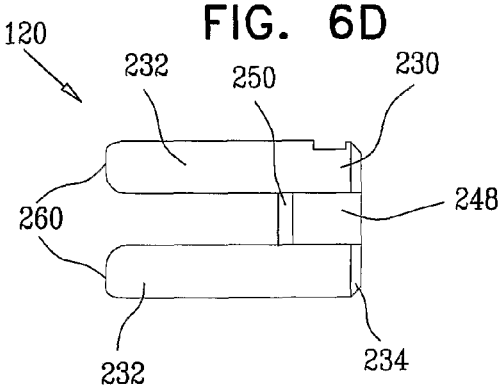
Figure 6E:
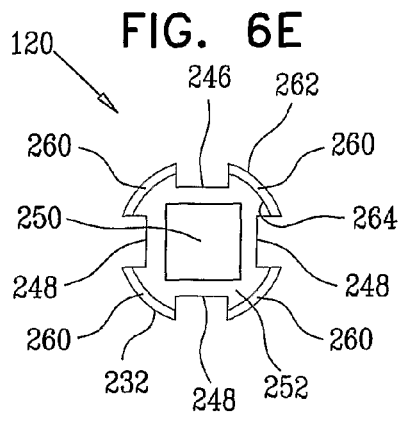
Figure 6F:
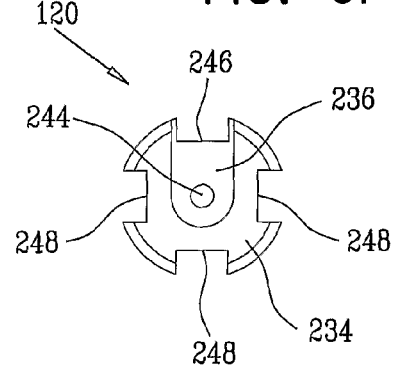

Referring generally to FIGS. 1 and 2, it is seen that device 100 preferably comprises a chassis element, such as a hand-engageable element 102 (FIGS. 4A-4E) which is generally symmetric about a longitudinal axis 104. A driver assembly 106 (FIGS. 3A-3D) is arranged for hand-driven displacement relative to element 102 along longitudinal axis 104.

Four arm elements 108 are individually pivotably mounted onto element 102 as by respective pins 110 for selectable pivotable displacement into and partially out of respective radially and axially extending slots 112 formed in element 102 and generally symmetrically distributed about longitudinal axis 104.

Springs 114 are disposed in respective slots 112 and engage respective arm elements 108 to urge the arm elements 108 radially outwardly. Springs 114 are preferably mounted on respective pins 116 and are located in respective cut outs 118 formed in each of arm elements 108. An axially driven collar engagement element 120 is removably mounted onto a forward end of driver assembly 106. A rotation preventing pin 122 engages an axially extending slot 124 in driver assembly 106 to prevent rotation of collar engagement element 120 relative to element 102 about axis 104.

As seen particularly in FIGS. 3A-3D, driver assembly 106 preferably comprises a generally cylindrical rod portion 130 in which is axially extending slot 124 is formed. At a rear end of generally cylindrical rod portion 130 there is preferably provided a hand engagement portion 132, such as a disc. At a forward end of generally cylindrical rod portion 130 there is preferably formed a quick release connector portion 134 which is generally planar and extends in a plane perpendicular to longitudinal axis 104 and has a cut out 136 having an edge surface 138. Disposed partially within and normally extending axially forward of connector portion 134 along axis 104 is a spring loaded ball engagement assembly 140, such as a spring loaded ball assembly product GN-614.3-4-NI, commercially available from ELESA-GANTER of 3 Triberger, Furtwangen, Germany.

Reference is now additionally made to FIGS. 4A-4E, which illustrate the hand-engageable element 102. The hand engageable element 102 preferably comprises an integrally formed generally circularly symmetric body, preferably formed of a molded or machined rigid plastic or metal, such as DELRIN® or stainless steel, including a generally cylindrical forward portion 150 having a forward-facing generally circular edge 152. Rearward of forward portion 150 there is preferably provided a forward generally conical transition portion 154 having a rearwardly increasing outer diameter.

Rearward of portion 154 there is preferably formed a main cylindrical portion 156, followed by a rearward generally conical transition portion 158 having an rearwardly increasing outer diameter. Rearward of portion 158 there is preferably formed a rearward cylindrical portion 160 having a rearward facing bulkhead surface 162. Rearward of portion 160 there is preferably formed a relatively narrow cylindrical portion 164 which terminates in a winged generally planar end portion 166 having forward-facing wing surfaces 168 and a rearward-facing surface 170.

Extending axially entirely through portions 166, 164, 160 and part of portion 158 of hand-engageable element 102 along longitudinal axis 104 is a relatively narrow generally circular cylindrical bore 180, which is sized to slidably accommodate and guide generally cylindrical rod portion 130 in its axial displacement relative to hand-engageable element 102.

Forwardly of cylindrical bore 180 there is formed in part of portion 158 and in portions 156, 154 and 150 of hand-engageable element 102 a relatively wide generally circular cylindrical bore 182 which defines the inner diameter of forward-facing generally circular edge 152.

Axially extending slots 112 are seen to extend in mutually adjacent 90 degree relative orientations forward from a location in portion 164 slightly rearwardly of surface 162, forwardly through portions 160, 158, 156, 154 and 150.

Bores 190 are formed in portion 160 to accommodate respective pins 110. Bores 196 are formed in main cylindrical portion 156 to accommodate respective pins 116 and bore 198 is formed in portion 166 to accommodate pin 122, which extends partly into bore 180 and thus engages axially extending slot 124 in driver assembly 106.

Reference is now additionally made to FIGS. 5A-5C, which illustrate the arm elements 108. As seen particularly in FIGS. 5A-5C, each arm element 108 is a generally planar element including a rearward portion 200 of a first, relatively greater thickness and a forward portion 202 of a second, relatively lesser thickness.

The rearward portion includes a rearwardly-disposed transversely extending bore 204 which accommodates pin 110 and cutout 118. Rearward portion includes an outer-facing edge surface 206 and a partially curved inward-facing edge surface 208.

Forward portion 202 includes a forwardmost finger portion 210 having a collar engagement edge surface 212 and a forward disposed, inward-facing edge surface 214 which extends rearwardly to a shoulder 216, rearward of which is a rearward disposed, inward-facing edge surface 218. Extending rearwardly of collar engagement edge surface 212 is partially curved outward-facing edge surface 220.

Reference is now additionally made to FIGS. 6A-6F, which illustrate axially driven collar engagement element 120. As seen in FIGS. 6A-6F, the collar engagement element 120 is a generally cylindrical symmetric element having a rearwardly-disposed hub 230 from which four collar engagement vanes 232, distributed about the circumference of hub 230, extend axially forward.

Hub 230 defines a rearward-facing wall portion 234 having formed therein an axial recess 236, which accommodates generally cylindrical rod portion 130. Forwardly of rearward-facing wall portion 234 there is provided a transverse slot 238, which accommodates quick release connector portion 134 and separates rearward-facing wall portion 234 from a rearward facing surface 240 of an intermediate wall portion 242, having formed therein a recess 244, arranged and configured to accommodate spring loaded ball engagement assembly 140. When quick release connector portion 134 is inserted in transverse slot 238, edge surface 138 of cut out 136 is preferably aligned with or located radially interior of a corresponding edge surface 246 of intermediate wall portion 242, which is preferably at the same radial separation from axis 104 and other corresponding edge surfaces 248 of intermediate wall portion 242 lying intermediate vanes 232.

Preferably a pad 250 formed of a resilient material is attached to a forward facing surface 252 of intermediate wall portion 242. Pad 250 typically engages a forward end of an endoscope and is provided to protect that forward end against impact damage.

Collar engagement vanes 232 preferably have a generally rounded forward-facing edge surface 260 and a somewhat rounded outer-facing collar engagement surface 262 as well as a somewhat rounded inner-facing endoscope engagement surface 264.

In accordance with a preferred embodiment of the present invention, vanes 232 have a length of approximately 16.5 mm and a width of approximately 6.5 mm, and the thickness of pad 250 is approximately 1.5 mm. According to a yet preferred embodiment of the present invention, the distance between inner-facing endoscope engagement surfaces 264 of opposing vanes 232 is approximately 14 mm, thereby allowing the insertion therebetween of endoscopes having any diameter of up to approximately 13 mm without causing damage to the endoscope.

It is appreciated that any suitable number of vanes 232 may be employed. Accordingly, it is appreciated that any suitable number of arm elements 108 may be employed. Specifically, three vanes 232 and three arm elements 108 may be employed.

Figure 7B:
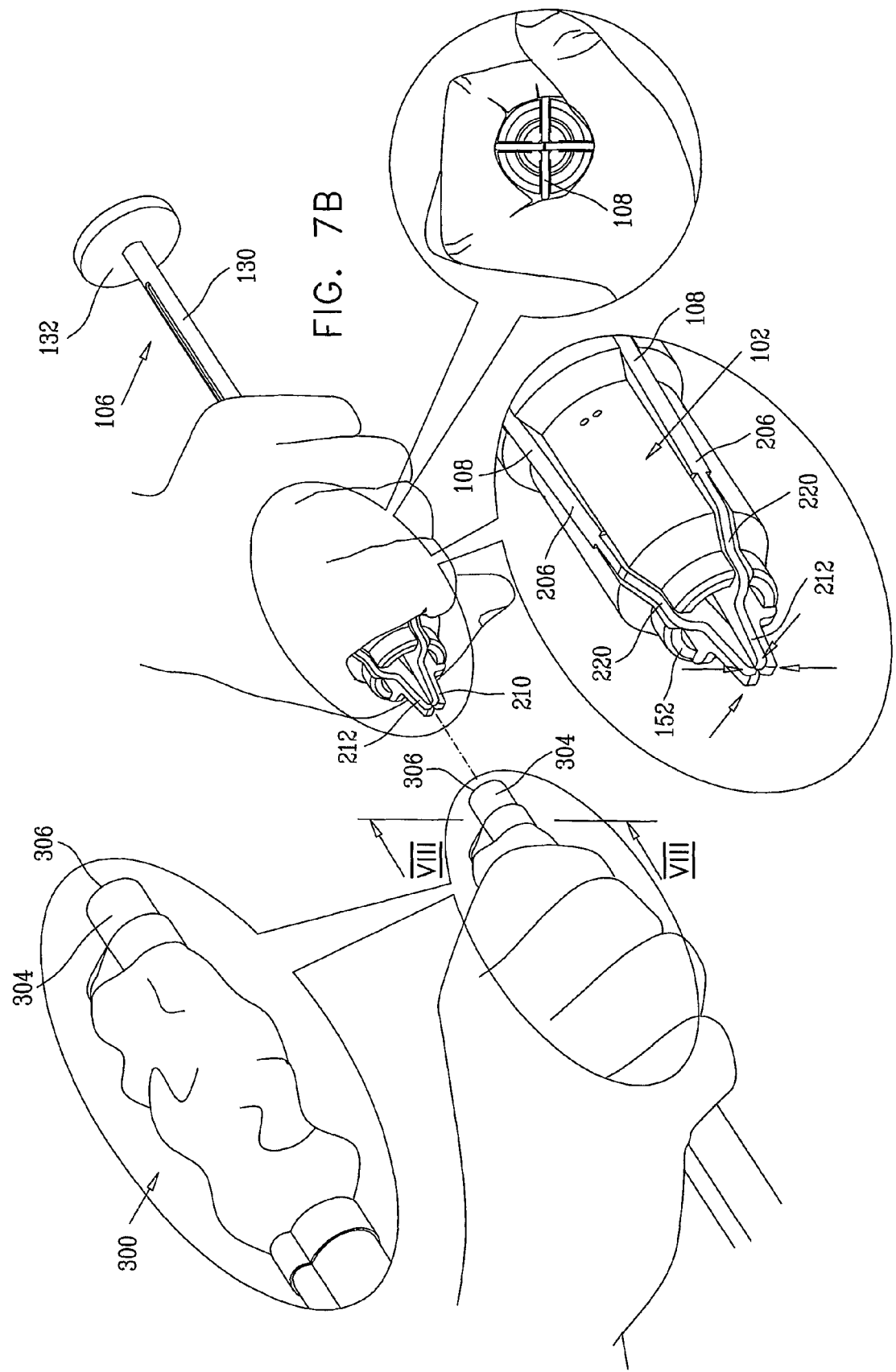
Figure 7F:
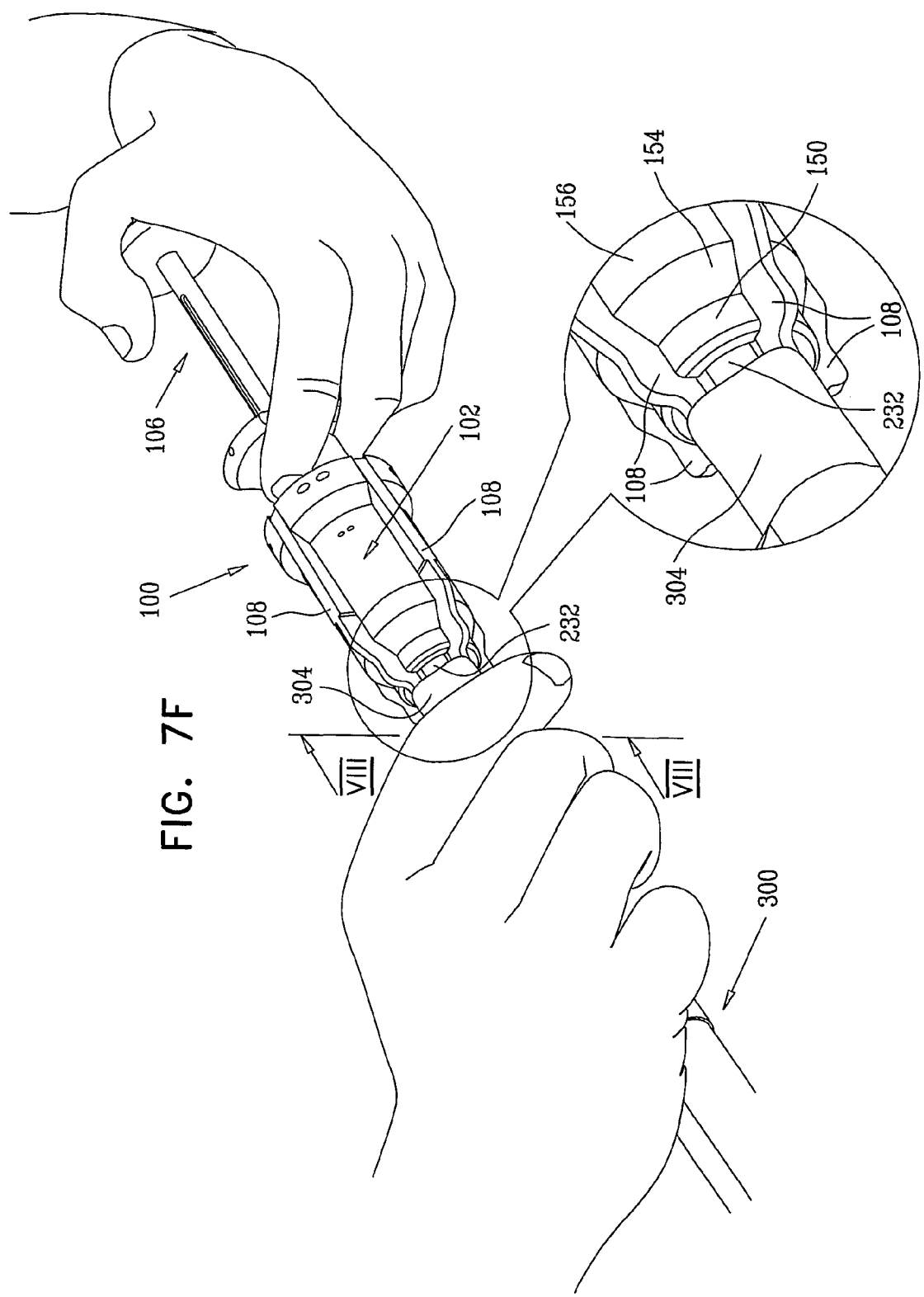
Figure 7G:
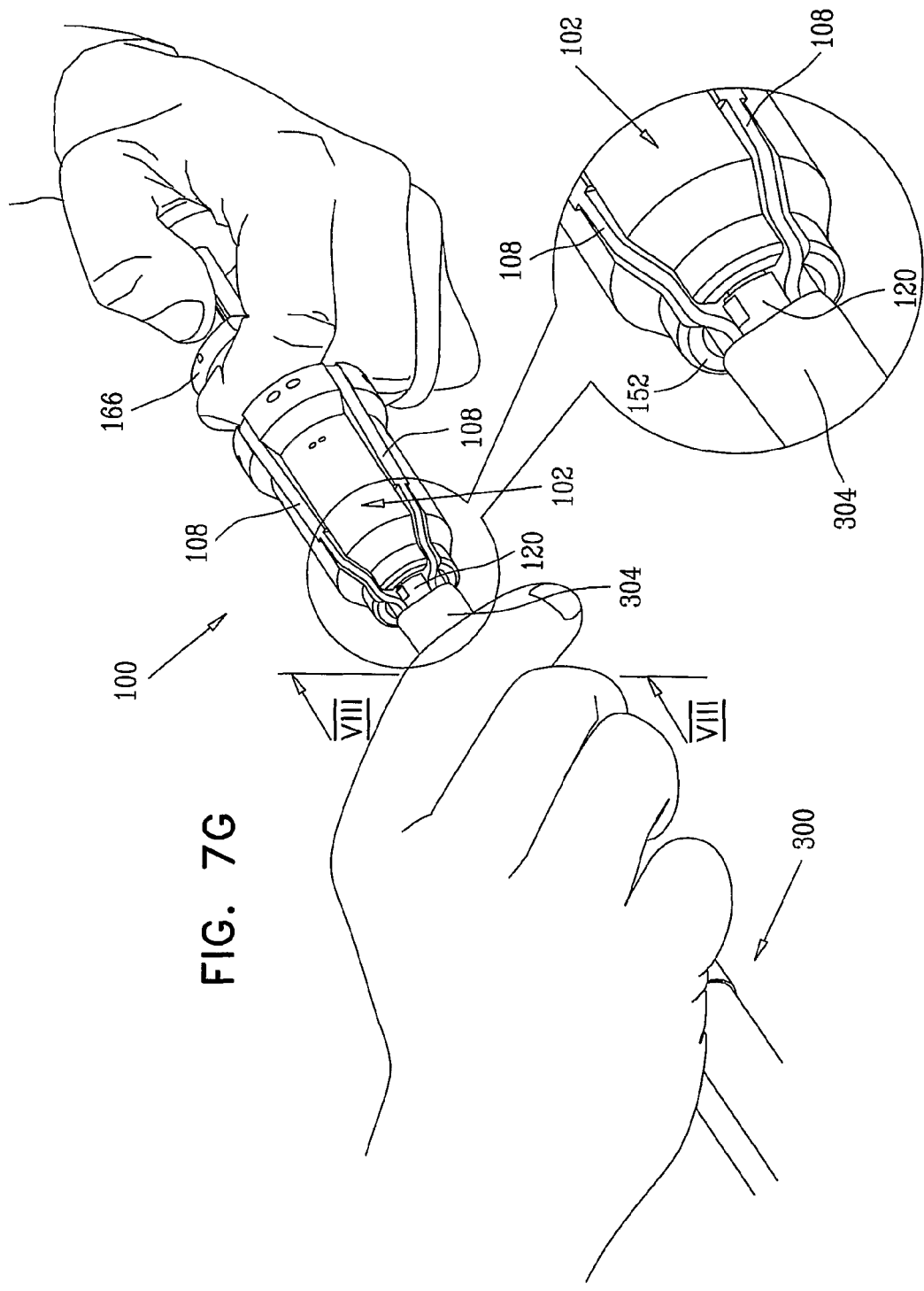
Figure 7H:
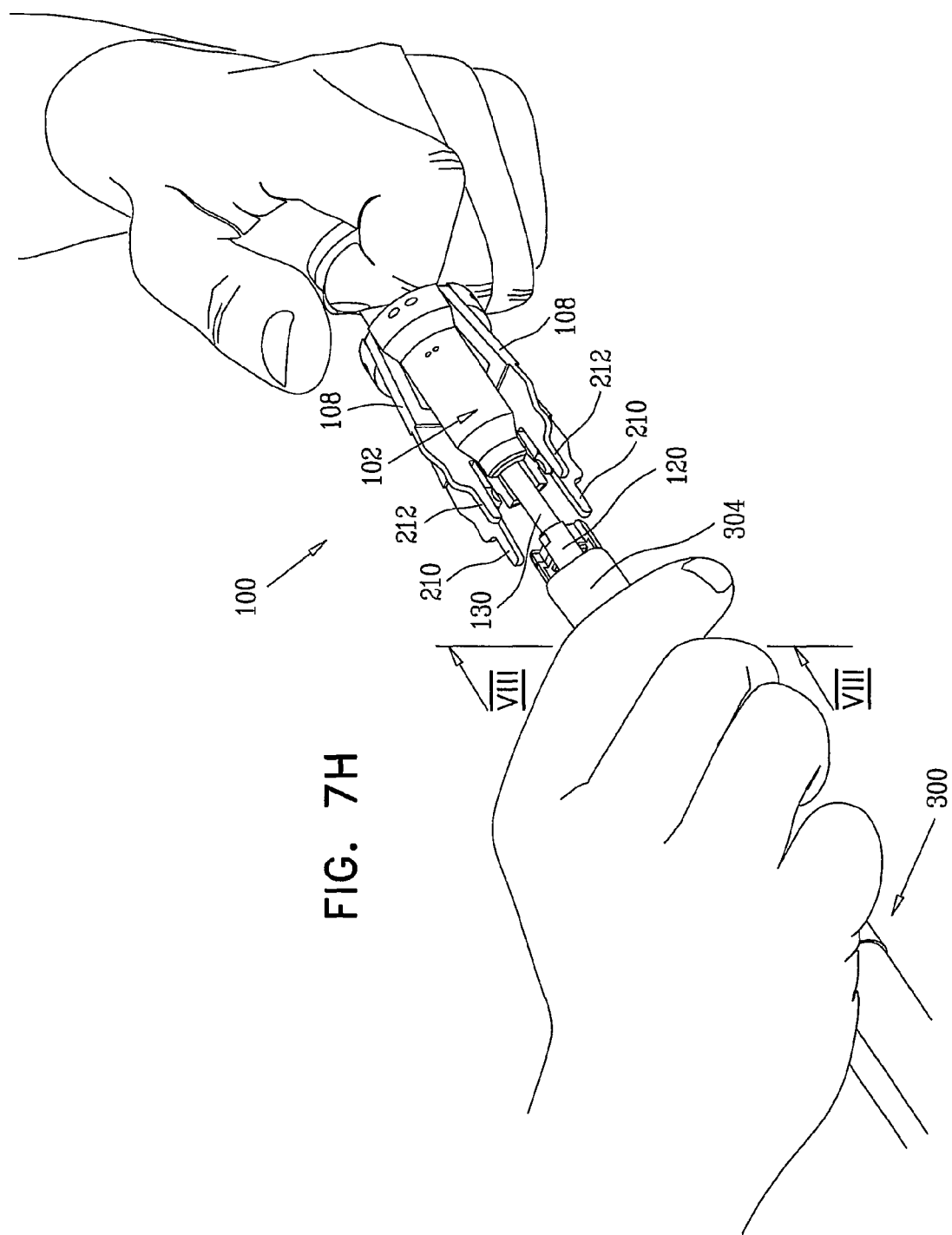
Figure 7J:
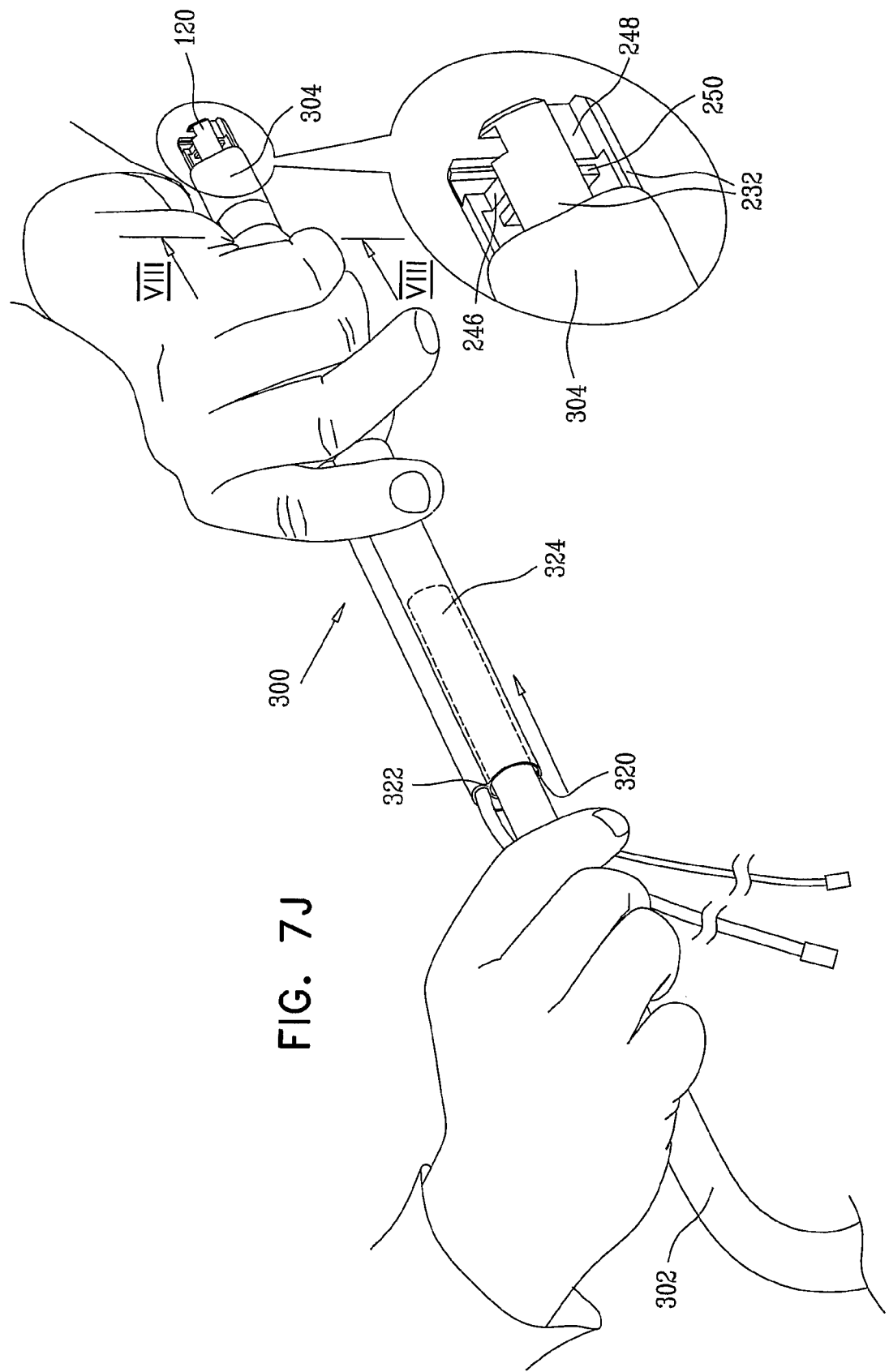
Figure 7K:
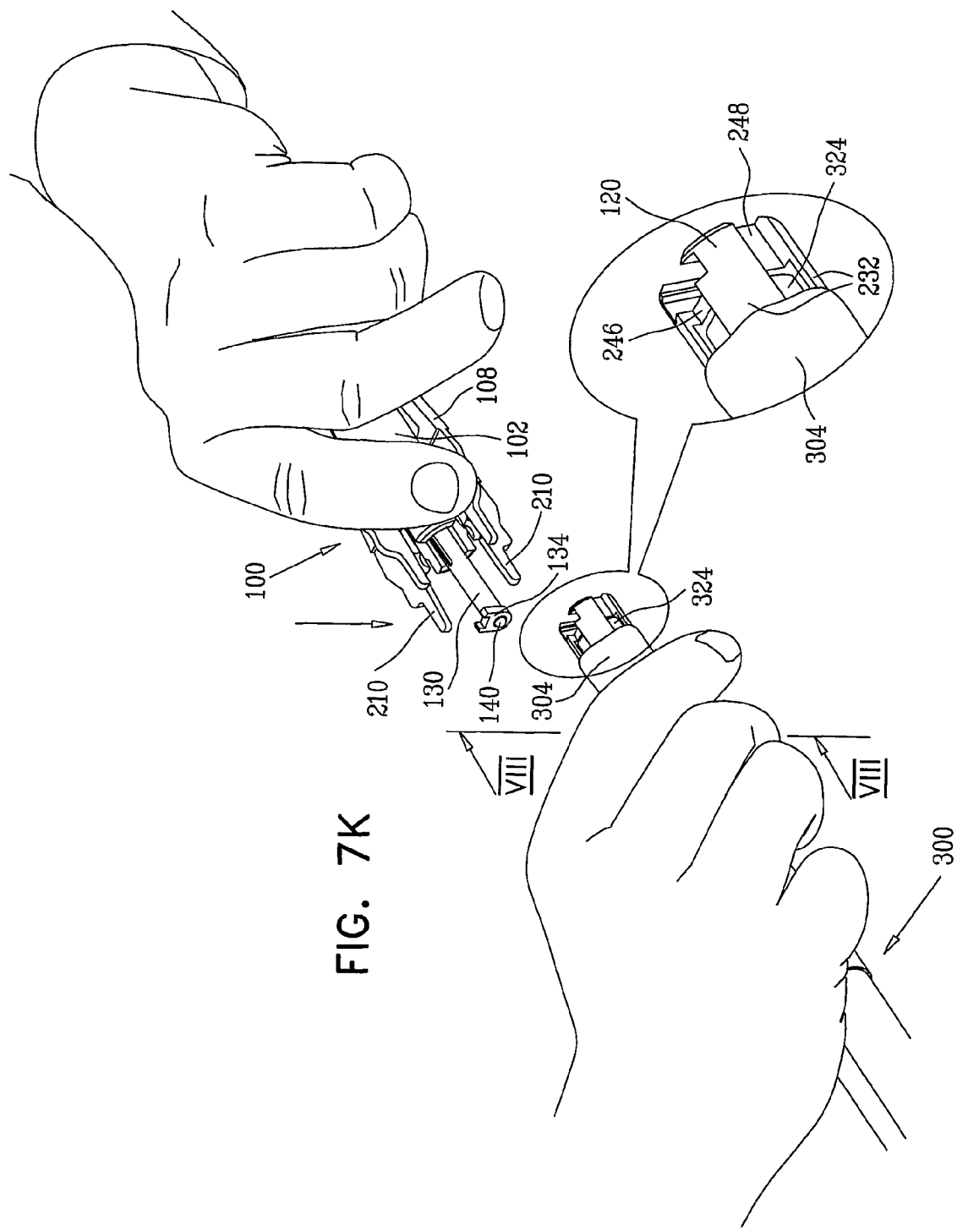
Figure 7M:
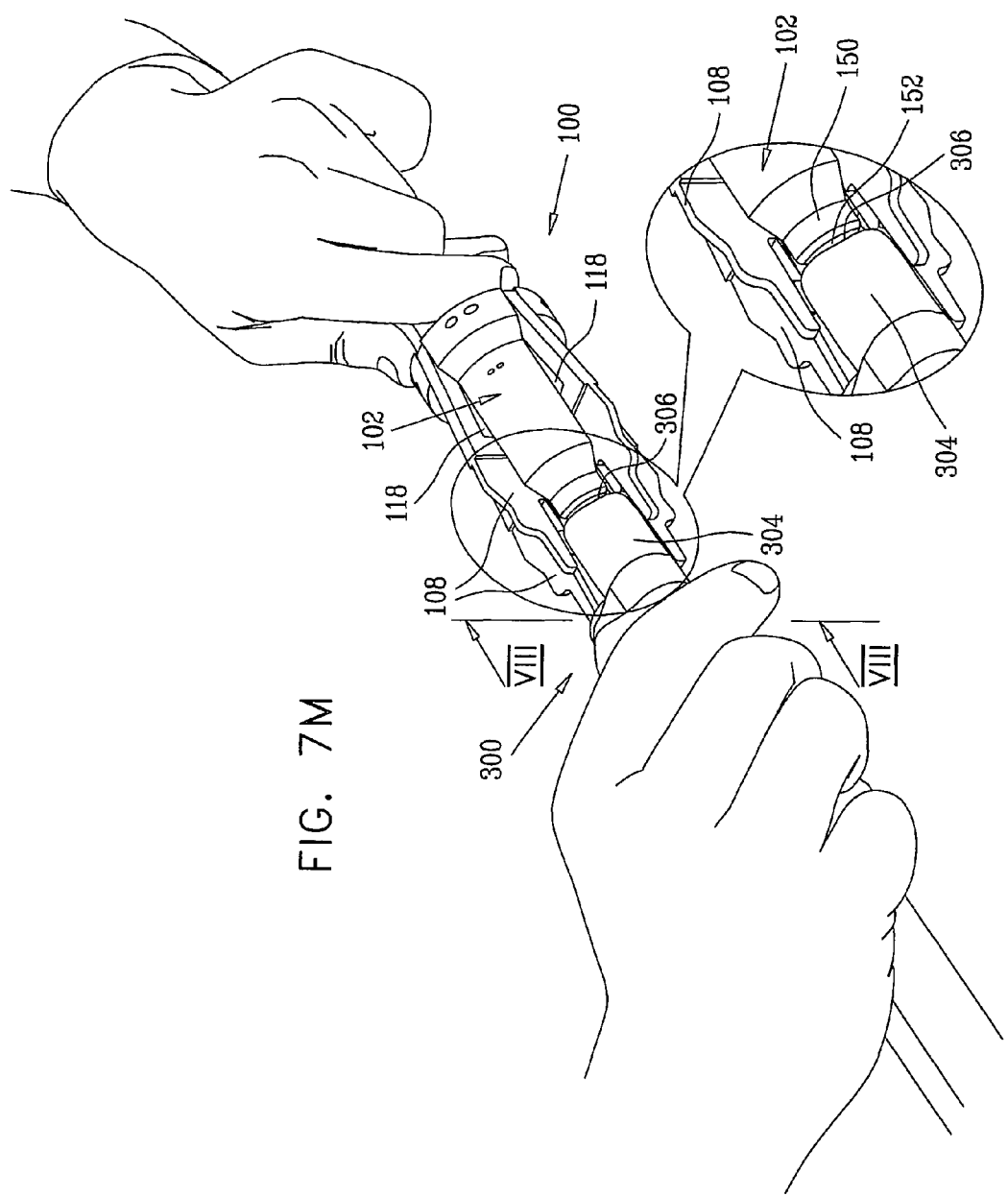
Figure 7N:
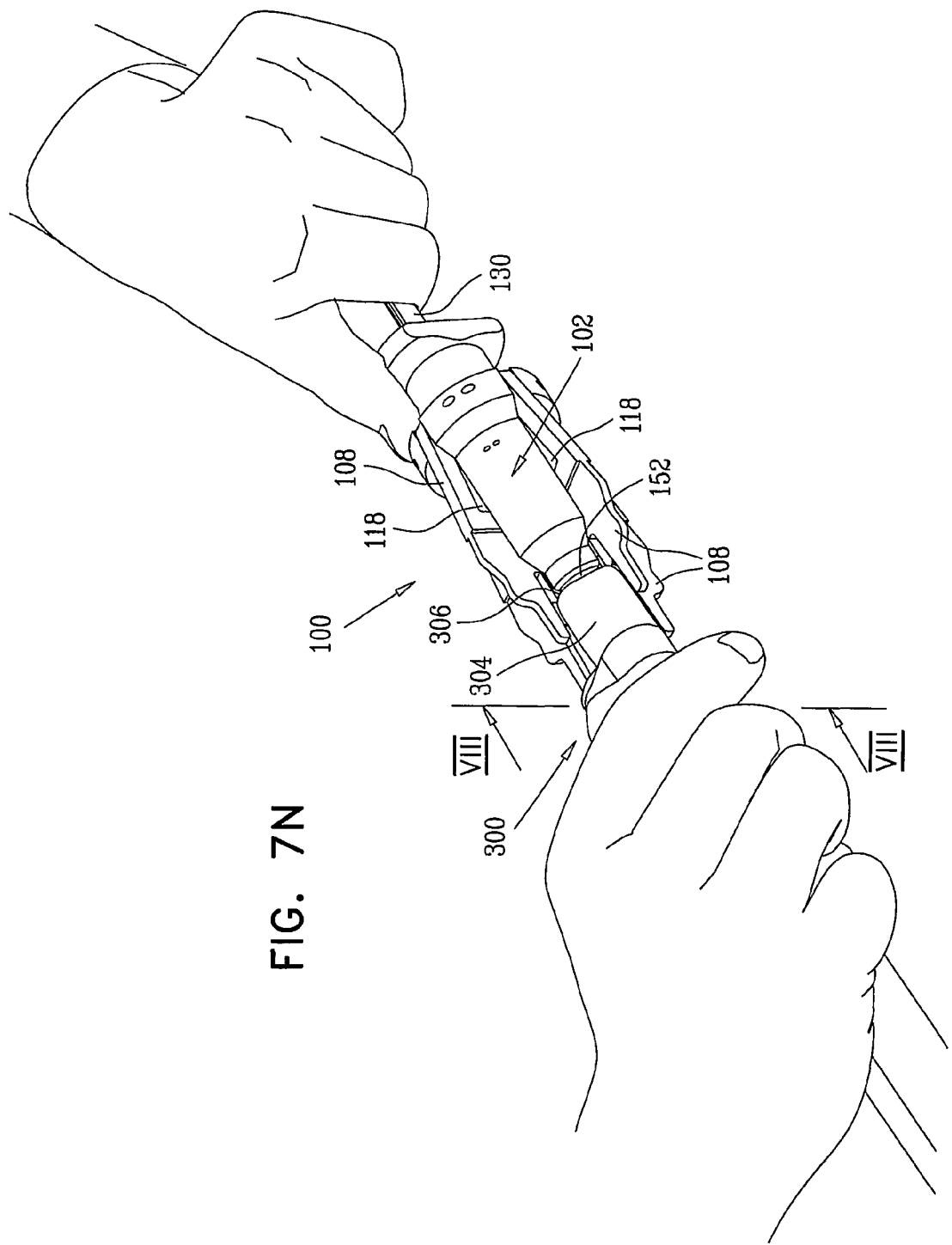
Figure 70:
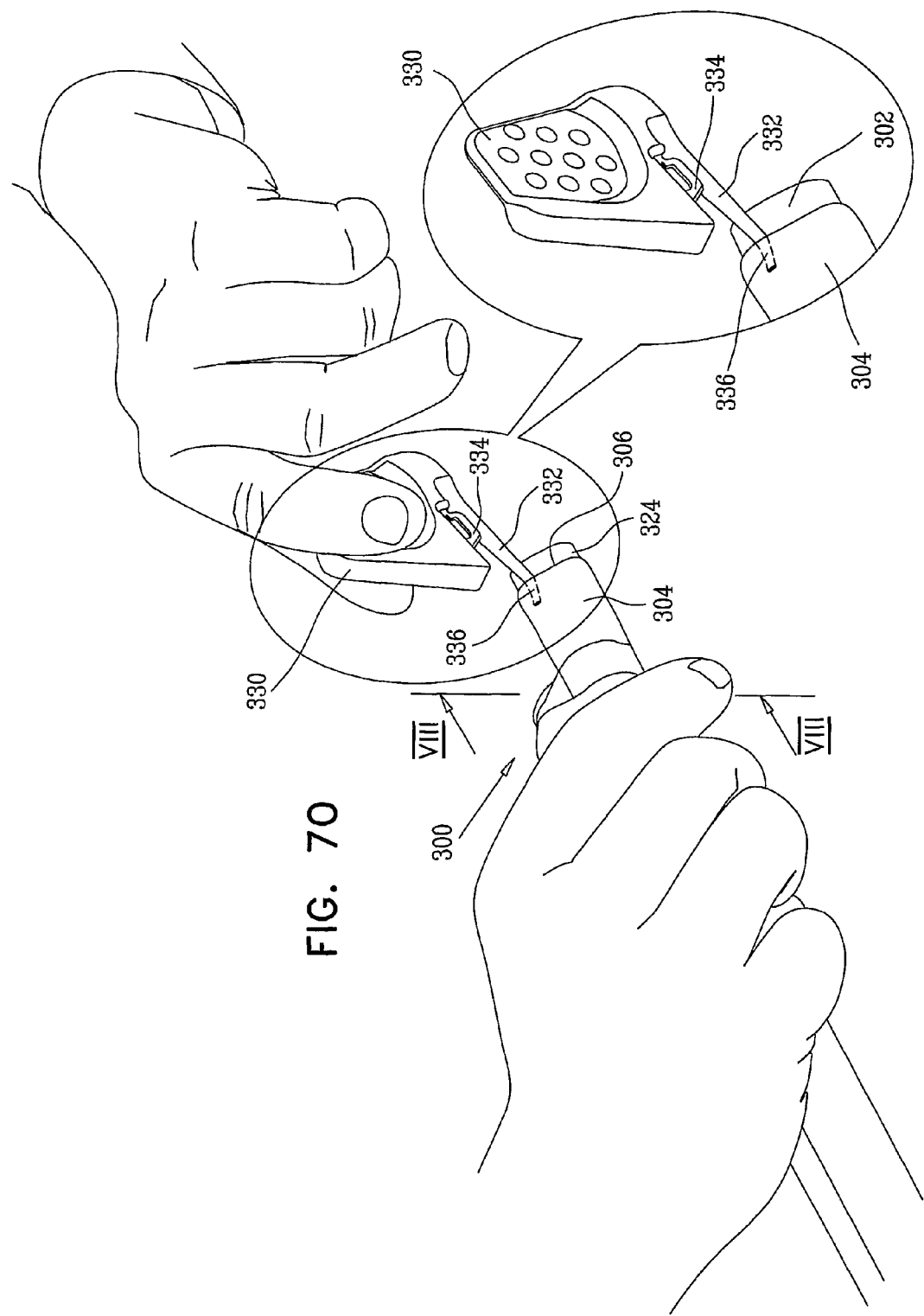
Figure 7P:
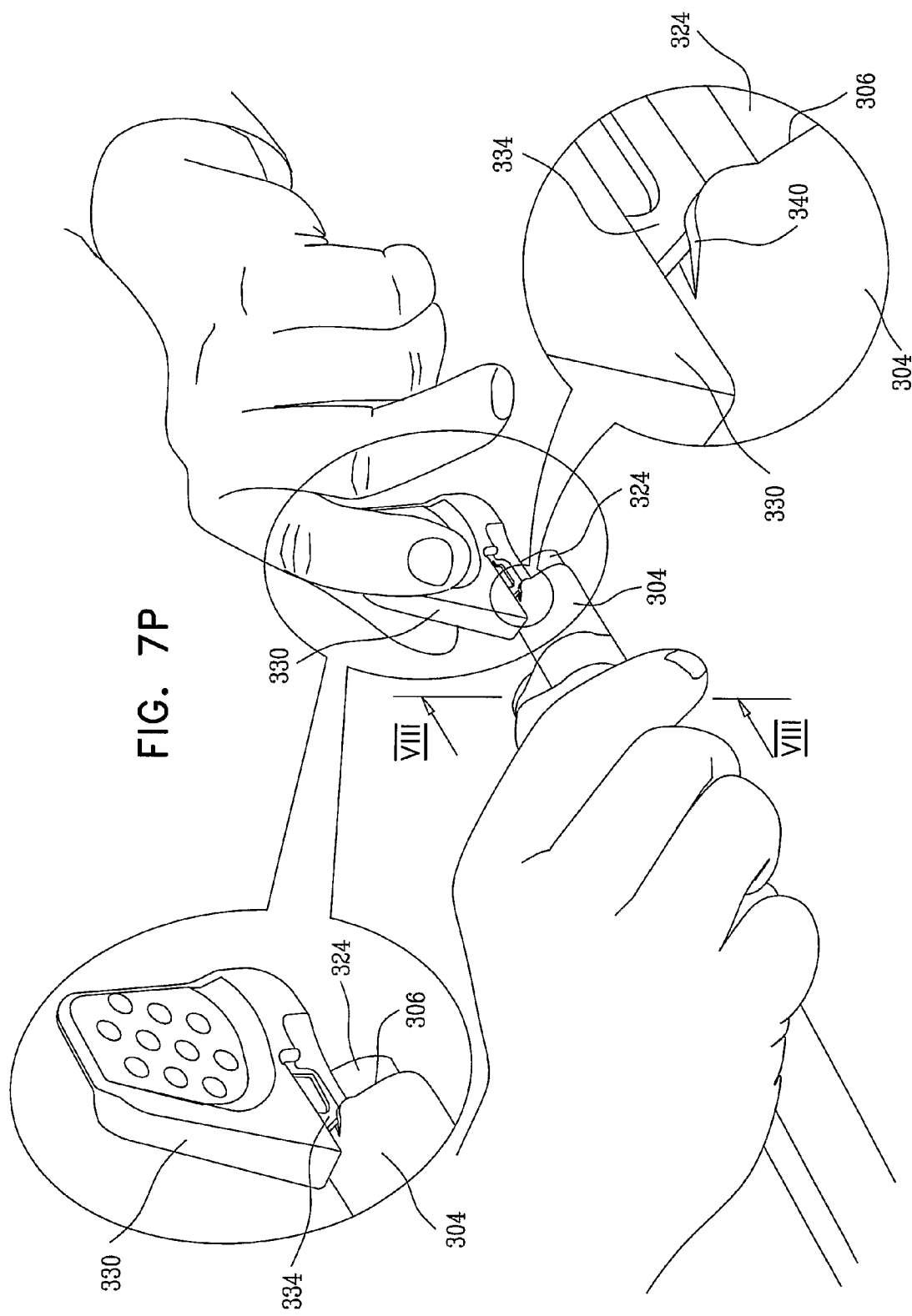

Reference is now made to FIGS. 7A, 7B, 7C, 7D, 7E, 7F, 7G, 7H, 7I, 7J, 7K, 7L, 7M, 7N, 7O, 7P and 7Q, which are simplified illustrations of various stages in the operation of the device of FIGS. 1 & 2 for mounting an auxiliary endoscope assembly onto an endoscope, and of various stages in the operation of a collar cutting tool for cutting a collar of an auxiliary endoscope assembly mounted on an endoscope; and to FIGS. 8A, 8B, 8C, 8D, 8E, 8F, 8G, 8H, 8I, 8J, 8K, 8L, 8M, 8N, 8O and 8P, which are sectional illustrations, taken along lines VIII-VIII in FIGS. 1 and 7A-7P in corresponding FIGS. 7A-7P.

As seen in FIGS. 7A-8P, the device 100 is employed to mount an auxiliary endoscope assembly 300 (shown in FIGS. 7A-8P) onto an endoscope 302 (shown in FIGS. 7J-7L, 7O-7Q, and 8J-8P). Endoscope 302 is preferably a conventional endoscope, such as a VSB-3430K video enteroscope or a EC-3470LK video colonoscope, which are connectable to an endoscopy console such as a console including a EPK-1000 video processor and a SONY LMD-2140MD medical grade flat panel LCD monitor, all commercially available from Pentax Europe GmbH, 104 Julius-Vosseler St., 22527 Hamburg, Germany.

In the illustrated example, the auxiliary endoscope assembly is commercially available from Smart Medical Systems Ltd. of Raanana, Israel under model designation NaviAid BGE and is described in PCT Published Applications PCT/IL2005/000849, PCT/IL2007/000600 and PCT/IL2007/000832, the disclosures of which are hereby incorporated by reference. It is appreciated that device 100 may be employed alternatively to mount another type of assembly having a resilient collar 304 onto an endoscope or other elongate element. Resilient collar 304 has an axially outward facing circumferential edge 306.

Preferably, collar 304 is formed of a resilient, relatively stretchable material such as latex or stretchable silicone. Preferably, the dimensions of collar 304 in a relaxed state are length in the range of 6-20 mm, inner diameter in the range of 6-10 mm, and thickness in the range of 1-2 mm. In accordance with a preferred embodiment of the present invention, collar 304 has a length of approximately 10 mm, an inner diameter of approximately 8 mm, and an outer diameter of approximately 11 mm.

Preferably, collar 304 is configured for tight and fixed mounting over endoscopes of various diameters. For example, a collar 304 having a length of 10 mm, inner and outer diameters of 8 and 11 mm respectively in a relaxed state, and an inner diameter of 23 mm in the maximally stretched state, is suitable for tight and fixed mounting on endoscopes having a diameter in the range of 9.8-13 mm.

Figure 8A:
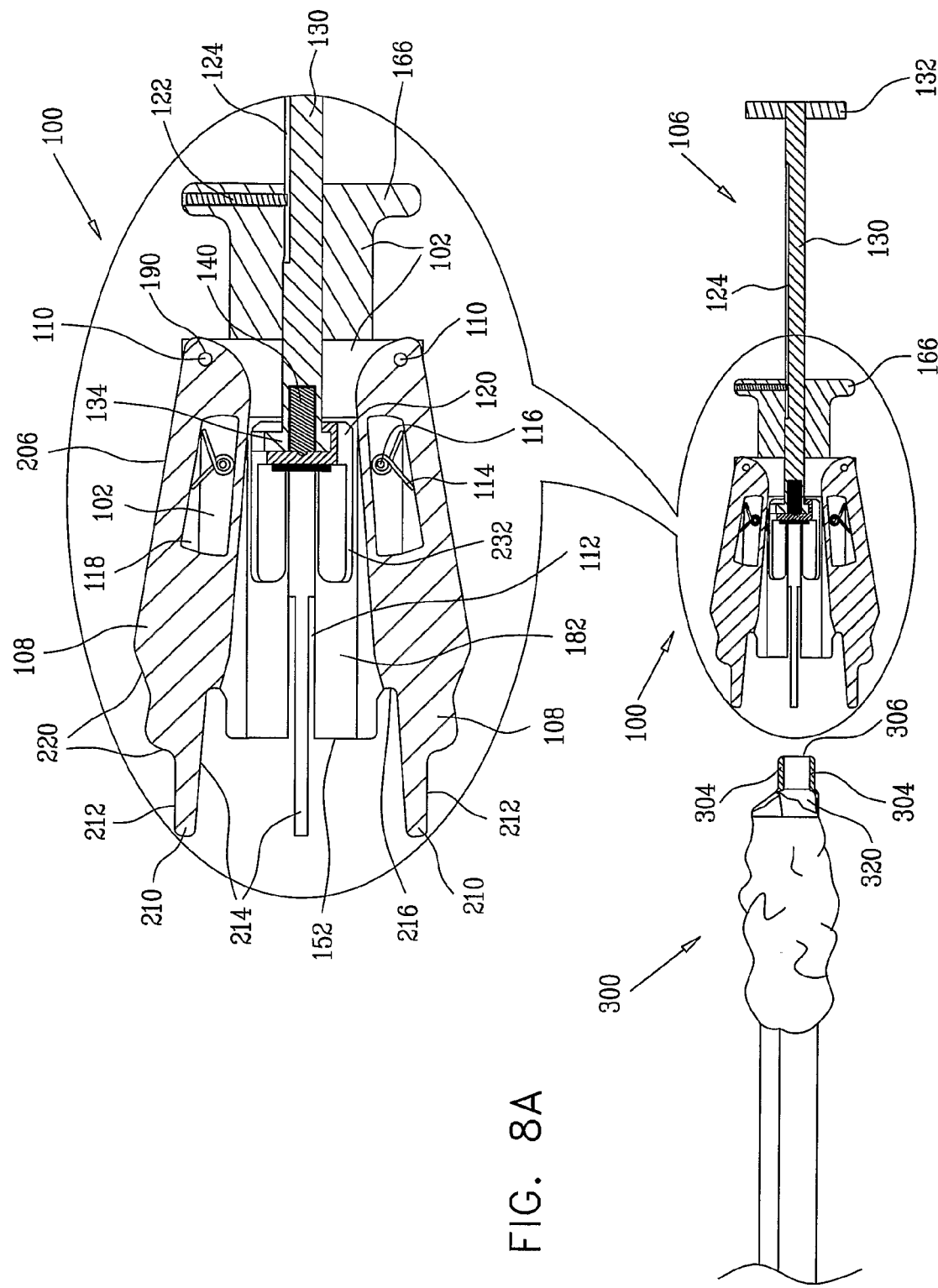

FIGS. 7A and 8A show the device 100 and the auxiliary endoscope assembly 300 prior to mutual engagement. Collar engagement element 120 is engaged by quick release connector portion 134. This engagement is maintained at least partially by the engagement of spring loaded ball engagement assembly 140 with recess 244.

Figure 8B:
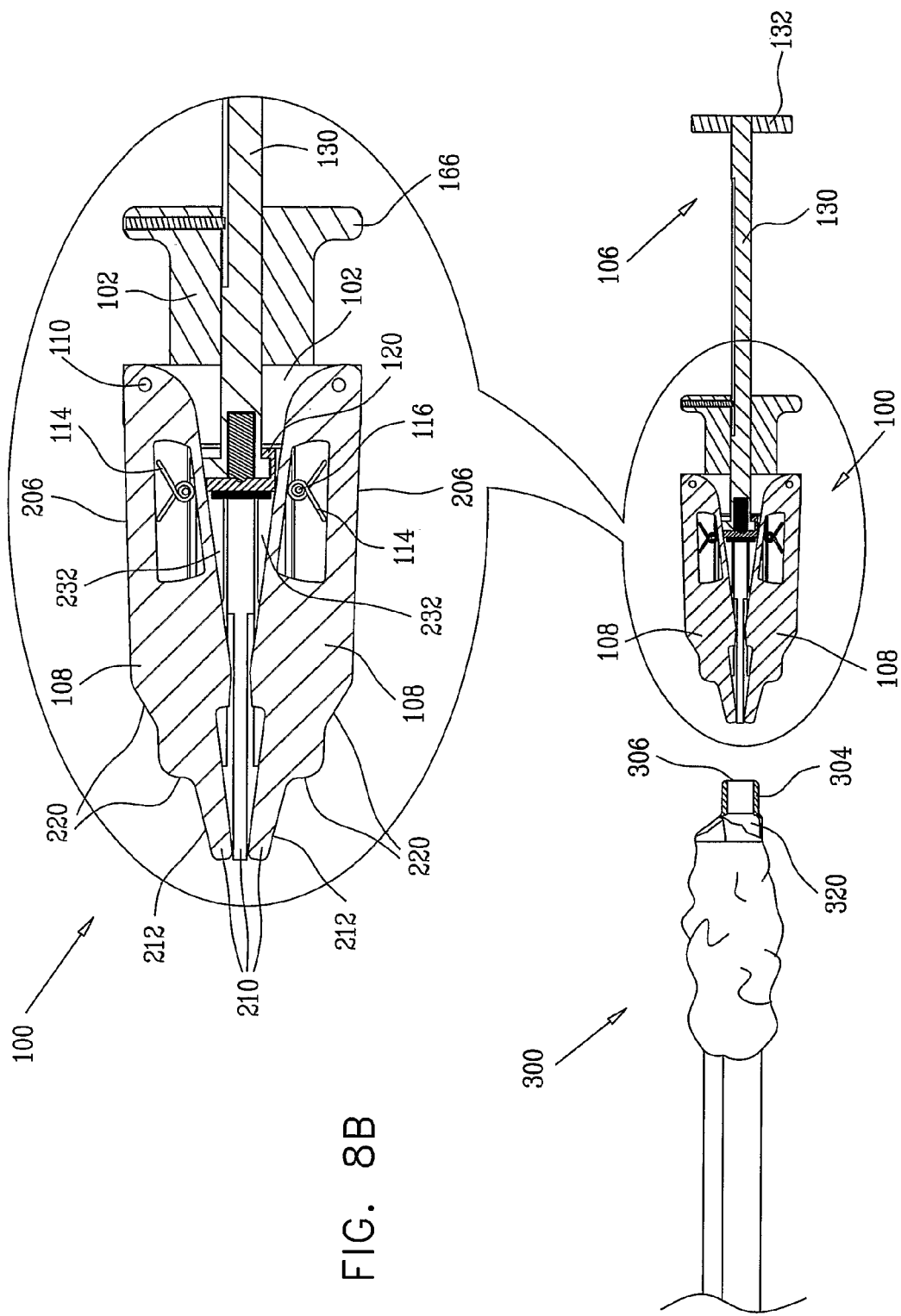

FIGS. 7B and 8B show a user holding the device 100 in one hand and holding the auxiliary endoscope assembly 300 in his other hand, with the collar 304 facing the device 100. It is noted that at this stage the driver assembly 106 is fully retracted with respect to the hand-engageable element 102. It is also noted that at this stage the user's hand engages outer-facing edge surfaces 206 and 220 of arm elements 108 and forces them, against the urging of springs 114, radially inwardly to a maximum possible degree such that collar engagement edge surfaces 212 of arm elements 108 define a generally non-truncated cone and thus can enter collar 304 as seen in FIGS. 7C and 8C and partially stretch the collar 304.

FIGS. 7D and 8D show collar engagement edge surfaces 212 partially stretching collar 304, when the user's hands no longer force arm elements 108 inwardly. Normally springs 114 are selected so that further stretching of collar 304 does not occur at this stage, as can be seen from a comparison of FIGS. 8C and 8D, which are identical.

FIGS. 7E and 8E show slight forward axial displacement of the driver assembly 106 relative to hand-engageable element 102. This forward displacement causes collar engagement element 120 to move axially forward such that engagement between edge surface 246 and 248 of hub 230 of collar engagement element 120 and corresponding inward-facing edge surfaces 208 forces arm elements 108 to pivot radially outwardly about pins 110 in bores 190 in hand-engageable element 102, thus expanding the cone defined by collar engagement edge surfaces 212 of finger portions 210 and further stretching collar 304.

FIGS. 7F and 8F show additional forward axial displacement of the driver assembly 106 relative to hand-engageable element 102. This additional forward displacement causes collar engagement element 120 to move axially forward to an additional extent such that engagement between edge surface 246 and 248 of hub 230 of collar engagement element 120 and corresponding inward-facing edge surfaces 218 forces arm elements 108 to pivot radially further outwardly about pins 110 in bores 190 in hand-engageable element 102, thus additionally expanding the cone defined by collar engagement edge surfaces 212 of finger portions 210 and even further stretching collar 304. This additional forward displacement also causes forward portions of vanes 232 to be located inside collar 304 but not in touching engagement therewith.

FIGS. 7G and 8G show further forward axial displacement of the driver assembly 106 relative to hand-engageable element 102. This further forward displacement causes collar engagement element 120 to move axially forward to a further extent such that engagement between edge surfaces 246 and 248 of hub 230 of collar engagement element 120 and corresponding inward-facing edge surfaces 214, which are separated from inward-facing edge surfaces 218 by shoulders 216 and lie radially outward with respect to surfaces 218, allows arm elements 108 to pivot radially inwardly about pins 110 in bores 190 in hand-engageable element 102, under the urging of the collar element 304 in engagement with collar engagement edge surfaces 212. This contracts the truncated cone defined by collar engagement edge surfaces 212 of finger portions 210 allowing collar 304 to be stretched only by virtue of the touching and supporting engagement of outer-facing collar engagement surfaces 262 of vanes 232 with the interior of collar 304.

FIGS. 7H and 8H show maximum forward axial displacement of the driver assembly 106 relative to hand-engageable element 102. This maximum forward displacement causes collar engagement element 120 to move axially forward to a maximum extent limited by the engagement of pin 122 with a rearward end of slot 124 in generally cylindrical rod portion 130 such that finger portions 210 of arm elements 108 are no longer in touching engagement with the collar 304 and are retracted therefrom, thus allowing arm elements 108 to pivot radially outward about pins 110 in bores 190 in hand-engageable element 102, under the urging of springs 114.

FIGS. 7I and 8I show the collar 304 being stretched by engagement with vanes 232 of collar engagement element 120 and disengagement of the collar engagement element 120 from the cylindrical rod portion 130.

FIGS. 7J and 8J show initial insertion of endoscope 302 into a lumen 320 of the auxiliary endoscope assembly 300 from an end 322 of the auxiliary endoscope assembly 300 opposite that at which collar 304 is located, while collar 304 is still being stretched by engagement with vanes 232 of collar engagement element 120.

FIGS. 7K and 8K show full insertion of endoscope 302 into lumen 320 of the auxiliary endoscope assembly 300 such that a forward end 324 of endoscope 302 engages pad 250 on collar engagement element 120.

FIGS. 7L and 8L show reengagement of the cylindrical rod portion 130 with the collar engagement element 120, by insertion of quick release connector portion 134 in slot 238 in collar engagement element 120. This engagement is maintained at least partially by the engagement of spring loaded ball engagement assembly 140 with recess 244. At this stage the driver assembly 106 is preferably in its fully forward position.

Reference is now specifically made to FIGS. 7M, 7N, 8M and 8N which illustrate resilient outer tubular article disengagement functionality operative for disengagement of at least a portion of the resilient outer tubular collar 304 from the collar engagement element 120.

Figure 8M:
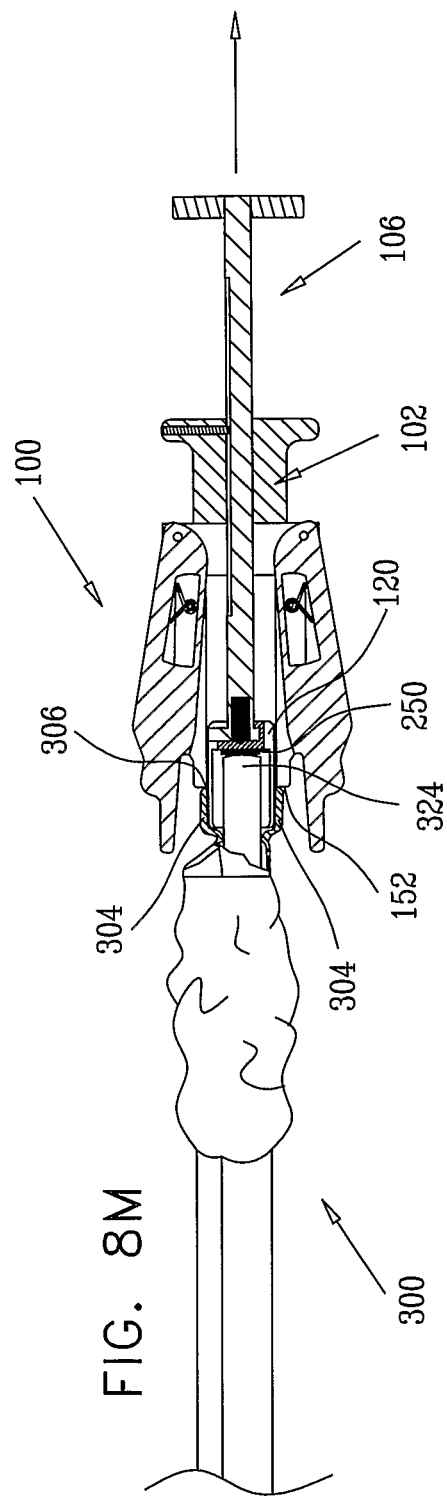

FIGS. 7M and 8M show operation of initial retraction of the driver assembly 106 relative to the hand-engageable element 102 to a stage where forward-facing generally circular edge 152 touchingly engages axially outward facing edge 306 of collar 304.

Figure 8N:
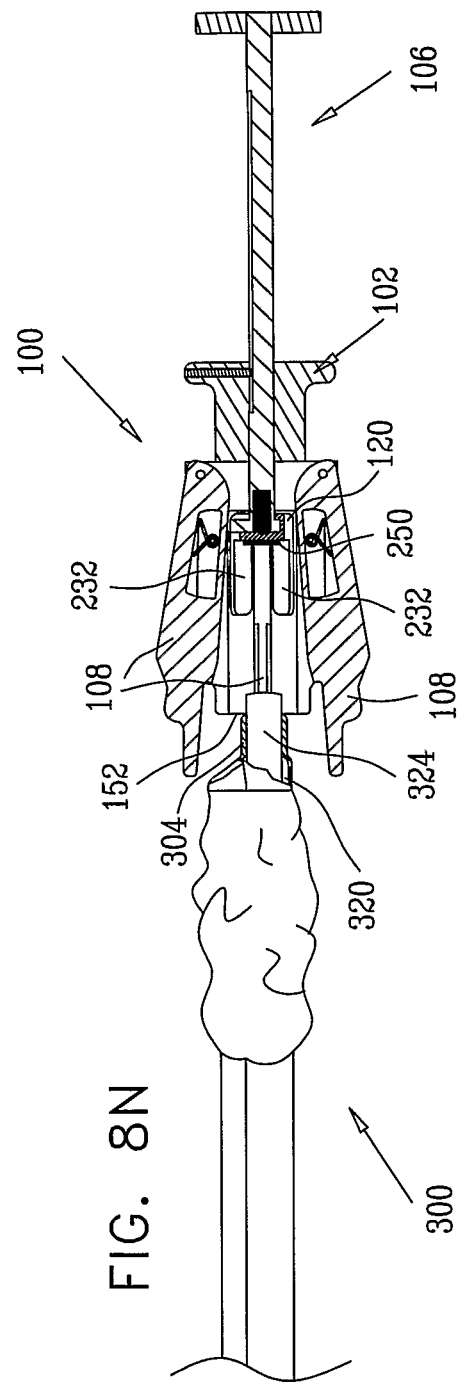
Figure 80:
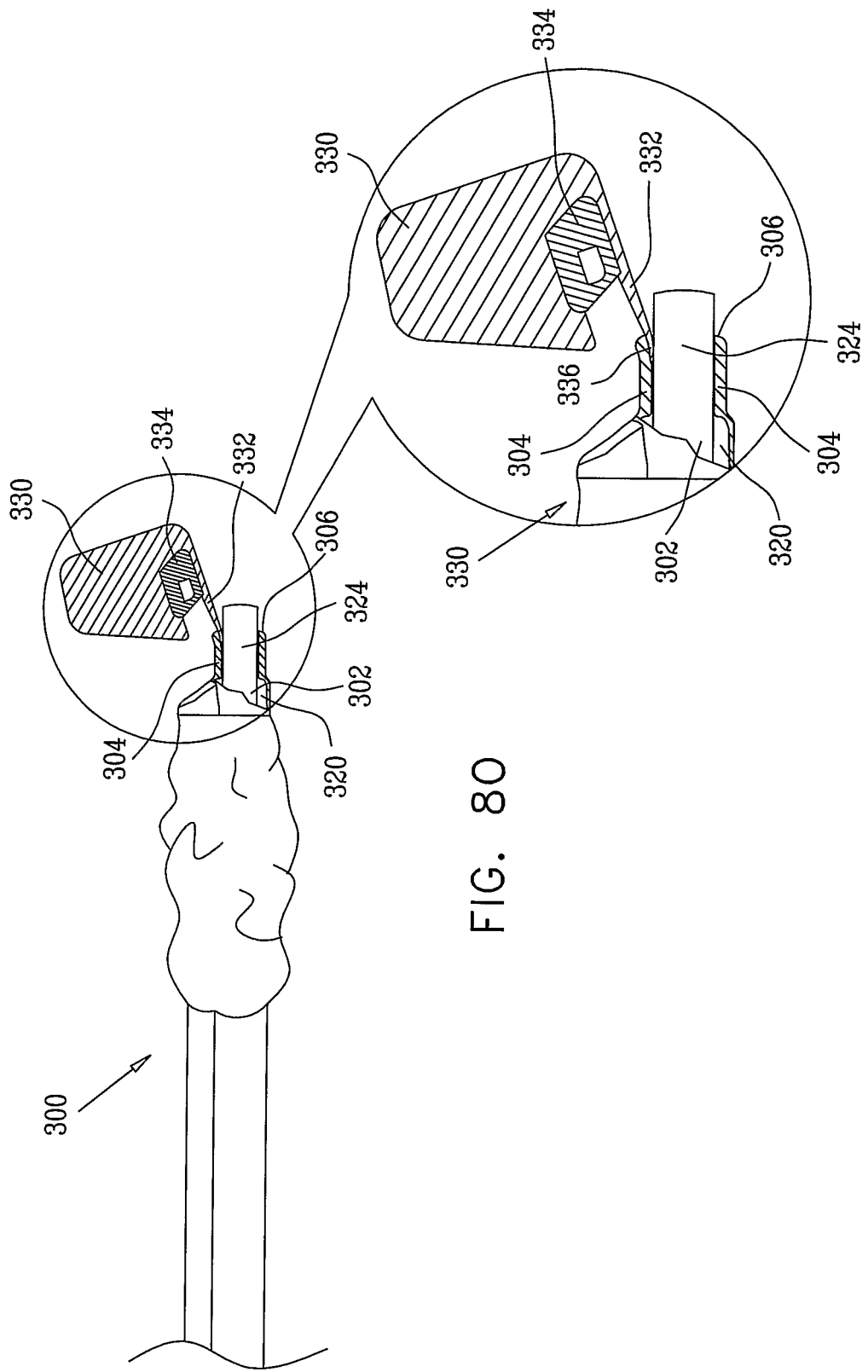

FIGS. 7N and 8N show full retraction of the driver assembly 106 relative to the hand-engageable element 102 to a stage where the vanes 232 of collar engagement element 120 are retracted and disengaged from the interior of the collar 304. At this stage the resilient collar 304 tightly hugs the end 324 of the endoscope 302.

It is appreciated that the structure of device 100 and the methodology described hereinabove normally will position the end 324 of the endoscope 302 at the predetermined distance from the axially outward facing edge 306 of collar 304, which preferably depends on the length of vanes 232. In accordance with a preferred embodiment of the present invention, vanes 232 have a length of approximately 16.5 mm and a width of approximately 6.5 mm, and the thickness of pad 250 is approximately 1.5 mm, thereby providing placement of a resilient collar 304 having a length of approximately 10 mm in a distance of approximately 2-5 mm from the forward edge of endoscope 302.

FIGS. 7O and 8O show an initial step in disengagement of the auxiliary endoscope assembly 300 from endoscope 302. A collar cutting tool 330 preferably having an elongate, tapered forward finger 332 and a collar cutting edge 334 is employed for this purpose. Forward finger 332 preferably demonstrates maximum flexibility at a forward portion 336 thereof and gradually increasing rigidity rearwardly thereof. Forward finger 332 is preferably formed of a material whose hardness is lower than that of an outer surface of endoscope 302, thereby to prevent possible damage thereto. FIGS. 7O and 8O show insertion of forward portion 336 of the forward finger 332 between collar 304 and endoscope 302, such that forward finger 332 functions as a spacer, spacing the endoscope 302 from the collar 304 and the cutting edge 334.

Figure 8P:
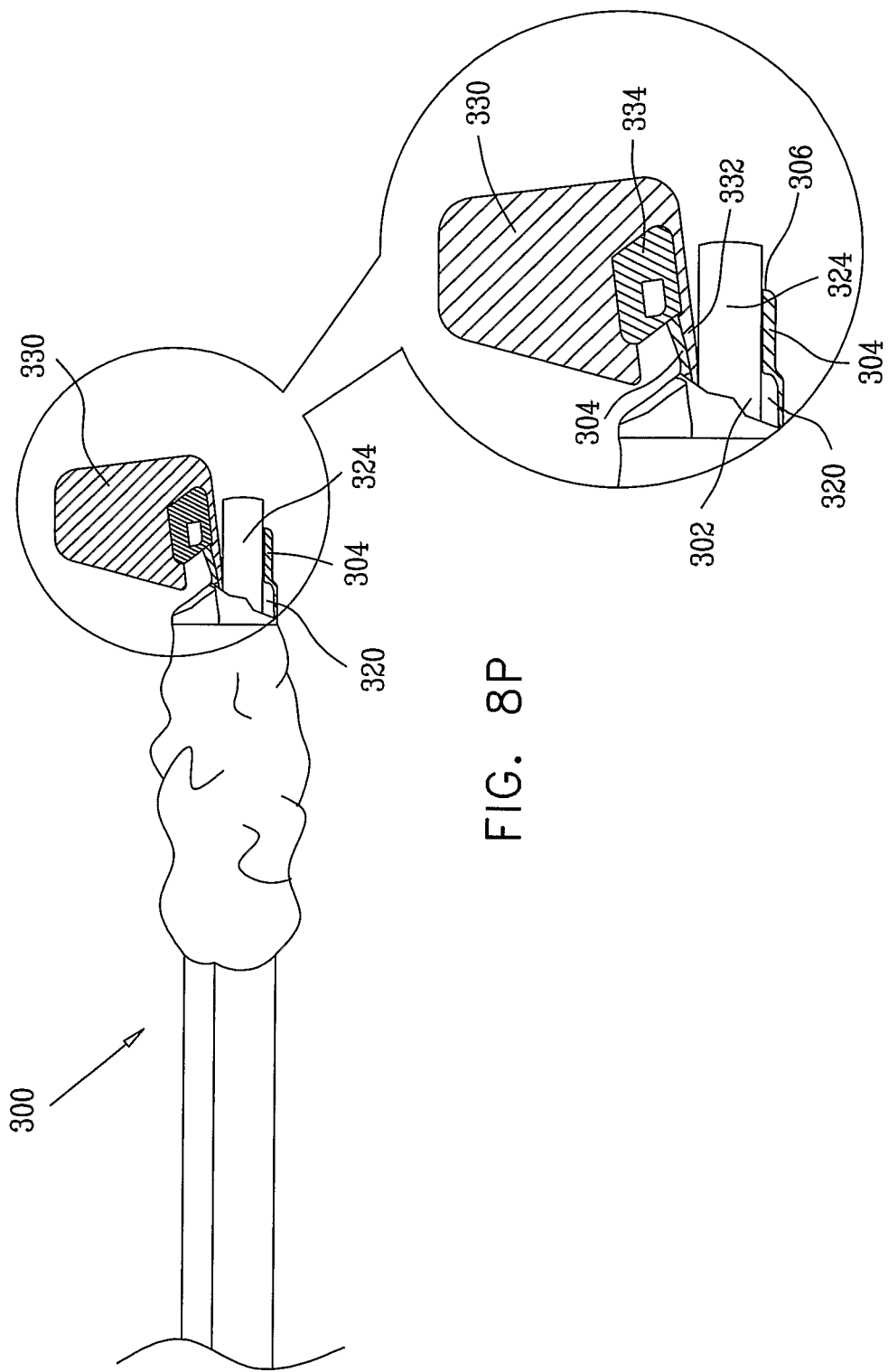

FIGS. 7P and 8P show a further step in disengagement of the auxiliary endoscope assembly 300 from endoscope 302. Collar cutting edge 334 of collar cutting tool 330 engages outward facing edge 306 of collar 304, forming a cut 340 therein.

Figure 7Q:
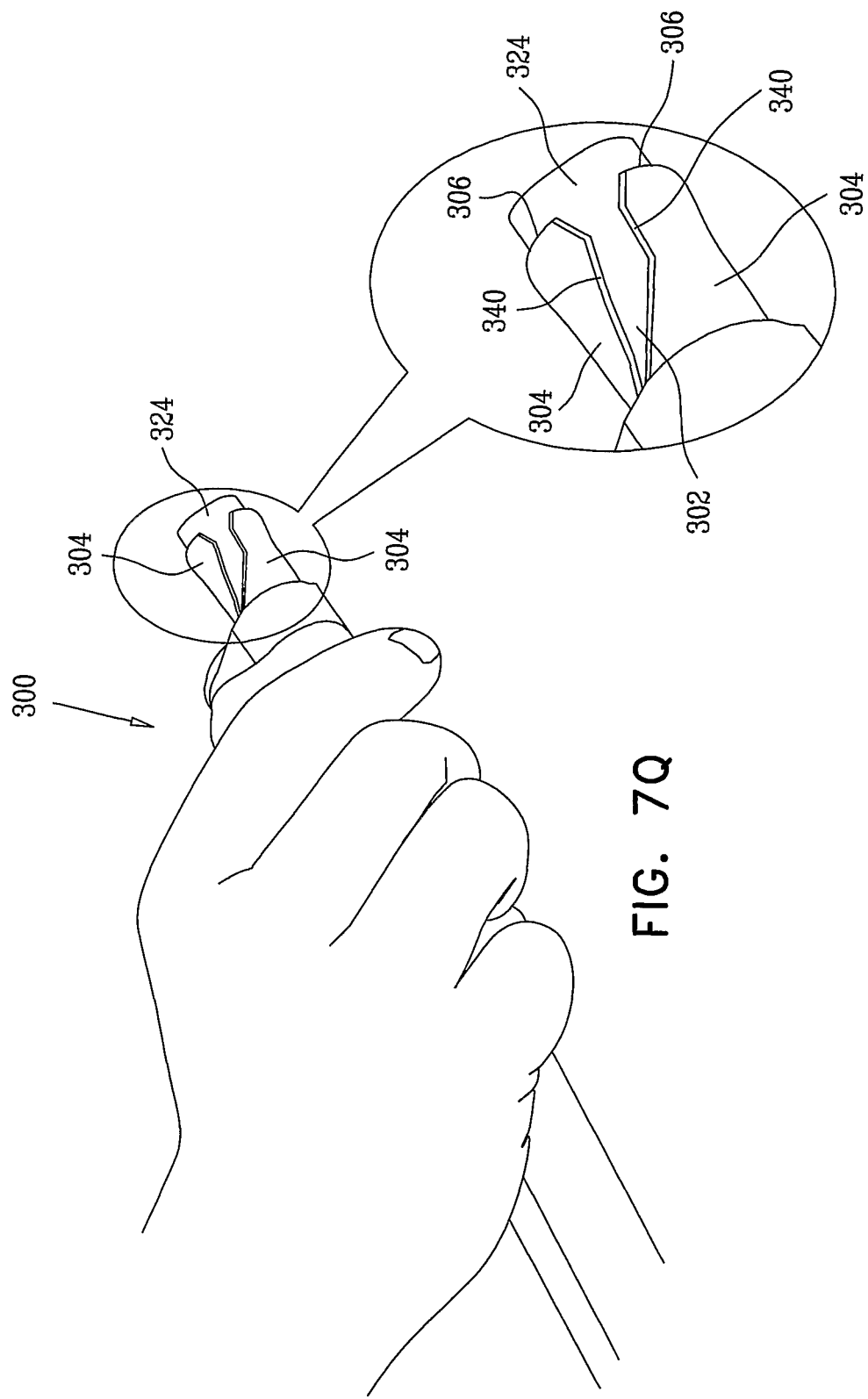

FIG. 7Q shows full slitting of collar 304 at cut 340, thus eliminating the previous hugging engagement of collar 304 and endoscope 302 (FIG. 7N). At this stage, the auxiliary endoscope assembly 300 may be readily slid off the endoscope 302.

Reference is now made to FIG. 9, which is a simplified, partially cut away, pictorial illustration of a double balloon device 400, constructed and operative in accordance with a preferred embodiment of the present invention, which is suitable for mounting on a conventional endoscope. As seen in FIG. 9, the double balloon device comprises a forward endoscope-mountable inflatable balloon assembly 402 and a rearward endoscope-mountable inflatable balloon assembly 404 which are interconnected by a flexible forward balloon inflation/deflation tube 406.

Forward endoscope-mountable inflatable balloon assembly 402 preferably includes a generally flexible, preferably resilient tubular sleeve 408, preferably having a forward-facing resilient collar 410 integrally formed therewith. Collar 410 may be similar to collar 304 described hereinabove and may alternatively be separate from sleeve 408 and attached thereto as by an adhesive. It is appreciated that collar 410 and sleeve 408, which are formed separately, may be formed of different materials, or from similar materials but with different properties such as strength, flexibility, stretchability and dimensions. For example, sleeve 408 may be formed of a highly flexible and stretchable silicone material, and collar 410 may be formed of a less flexible and less stretchable silicone material having a higher expansion resistance.

Sleeve 408 is preferably cylindrical and is arranged about an axis 412 and preferably has a main lumen 414 for accommodating an endoscope and a side lumen 416 for accommodating a forward portion 418 of flexible forward balloon inflation/deflation tube 406. Side lumen 416 extends along part of the length of sleeve 408, forwardly from its rearward facing end and outwardly of main lumen 414 along a generally spiral path with respect to axis 412 and terminates in an open end 420. Preferably forward portion 418 extends partially along and inside side lumen 416 and is fixedly and sealingly attached thereto as by a suitable adhesive, so as to provide a sealed inflation/deflation pathway therewith. Typically sleeve 408 has a length of approximately 8-15 cm.

It is appreciated that sleeve 408 may be constructed of a flexible and stretchable material, such as flexible and stretchable silicon, latex or rubber, thereby enabling it to conform to bending of an endoscope onto which it is mounted. It is further appreciated that main lumen 414 of sleeve 408 preferably has an untensioned inner circumference slightly larger than the cross-sectional circumference of an endoscope being inserted therethrough, thereby allowing it to be pulled and slid over the endoscope during mounting thereof.

A forward inflatable balloon 430 is sealably mounted onto an outer surface of sleeve 408 and arranged with respect to side lumen 416 such that open end 420 of side lumen 416 lies interiorly thereof for providing inflation and deflation thereof.

It is appreciated that in accordance with a preferred embodiment of the present invention balloon 430 is generally inflatable, and can be inflated to a diameter about 3-10 times larger than its diameter when not inflated. In accordance with a preferred embodiment of the present invention, useful for small intestine endoscopy, the diameter of balloon 430 when fully inflated is in the range of 35-45 mm. Preferably, inflation of balloon 430 to a diameter less than 45 mm may be achieved using relatively low pressure, such as in the range of 20-40 millibars.

In another specific embodiment, useful for large intestine endoscopy, the diameter of balloon 430, when fully inflated, is in the range of 4-6 centimeters. In a further embodiment, also useful for large intestine endoscopy, the diameter of balloon 430, when fully inflated, is six centimeters. Preferably, inflation of balloon 430 to a diameter less than six centimeters may be achieved using relatively low pressure, such as in the range of 20-40 millibars.

It is appreciated that in accordance with a preferred embodiment of the present invention, useful for in vivo inspection of a generally tubular body portion having a variable cross-sectional diameter, the expansion diameter range of balloon 430, when mounted onto an endoscope, is larger than the maximum cross-sectional diameter of the generally tubular body portion, thereby enabling engagement of expanded balloon 430 with the interior surface of the generally tubular body portion, and anchoring of the endoscope thereto. Preferably, balloon 430 is a relatively soft, highly compliant balloon, operative to at least partially conform to the shape of the interior surface of the generally tubular body portion when in engagement therewith.

It is appreciated that balloon 430 may be formed of suitable well-known stretchable materials such as latex, flexible silicone, or highly flexible nylon. Alternatively, balloon 430 may be formed of polyurethane, which is less stretchable and conforming than latex, flexible silicone or highly flexible nylon. Preferably, the diameter of balloon 430 is sufficient to ensure tight anchoring at any part of the generally tubular body portion. Alternatively, balloon 430 may be obviated.

Rearward endoscope-mountable inflatable balloon assembly 404 preferably includes a generally non axially compressible, tubular sleeve 438. Sleeve 438 is preferably cylindrical and in use is arranged about axis 412 and preferably has a main lumen 440 for accommodating an endoscope and first and second side lumens 442 and 444.

First side lumen 442 accommodates a rearward portion 446 of flexible forward balloon inflation/deflation tube 406. First side lumen 442 extends along the length of sleeve 438, outwardly of main lumen 440 along a generally spiral path with respect to axis 412. Preferably rearward portion 446 extends partially along and inside a forward facing portion 448 of first side lumen 442 and is fixedly and sealingly attached thereto as by a suitable adhesive, so as to provide a sealed inflation/deflation pathway therewith. A forward balloon inflation/deflation supply and exhaust tube 450 extends from a connector 452 outside of assembly 404, partially along and inside a rearward facing portion 454 of first side lumen 442 and is fixedly and sealingly attached thereto as by a suitable adhesive, so as to provide a sealed inflation/deflation pathway therewith.

Second side lumen 444 accommodates a forward portion 462 of a flexible rearward balloon inflation/deflation supply and exhaust tube 464. Second side lumen 444 extends along part of the length of sleeve 438, outwardly of main lumen 440 along a generally spiral path with respect to axis 412 from a rear edge of sleeve 438 to an open end 466. Rearward balloon inflation/deflation supply and exhaust tube 464 extends from a connector 472 outside of assembly 404, partially along and inside a rearward facing portion 474 of second side lumen 444 and is fixedly and sealingly attached thereto as by a suitable adhesive, so as to provide a sealed inflation/deflation pathway therewith.

A rearward inflatable balloon 480 is sealably mounted onto an outer surface of sleeve 438 and arranged with respect to second side lumen 444 such that open end 466 of second side lumen 444 lies interiorly thereof for providing inflation and deflation thereof. It is appreciated that in accordance with a preferred embodiment of the present invention balloon 480 is generally inflatable, and can be inflated to a diameter about 3-10 times larger than its diameter when not inflated. In accordance with a preferred embodiment of the present invention, useful for small intestine endoscopy, the diameter of balloon 480 when fully inflated is in the range of 35-45 mm. Preferably, inflation of balloon 480 to a diameter less than 45 mm may be achieved using relatively low pressure, such as in the range of 20-40 millibars.

In another specific embodiment, useful for large intestine endoscopy, the diameter of balloon 480, when fully inflated, is in the range of 4-6 centimeters. In a further embodiment, also useful for large intestine endoscopy, the diameter of balloon 480, when fully inflated, is six centimeters. Preferably, inflation of balloon 480 to a diameter less than six centimeters may be achieved using relatively low pressure, such as in the range of 20-40 millibars.

It is appreciated that in accordance with a preferred embodiment of the present invention, useful for in vivo inspection of a generally tubular body portion having a variable cross-sectional diameter, the expansion diameter range of balloon 480, when mounted onto sleeve 438, is larger than the maximum cross-sectional diameter of the generally tubular body portion, thereby enabling engagement of expanded balloon 480 with the interior surface of the generally tubular body portion, and anchoring of sleeve 438 thereto. Preferably, balloon 480 is a relatively soft, highly compliant balloon, operative to at least partially conform to the shape of the interior surface of the generally tubular body portion when in engagement therewith.

It is appreciated that balloon 480 may be formed of suitable well-known stretchable materials such as latex, flexible silicone, or highly flexible nylon. Alternatively, balloon 480 may be formed of polyurethane, which is less stretchable and conforming than latex, flexible silicone or highly flexible nylon. Preferably, the diameter of balloon 480 is sufficient to ensure tight anchoring at any part of the generally tubular body portion. Alternatively, balloon 480 may be obviated.

Preferably a fiducial mark 482 is provided at a rearward end of sleeve 438 to enable an operator to monitor and prevent undesired rotation of tube 438 about axis 412. Preferably, sleeve 438 is of a typical length of approximately 120-150 cm and has an inner diameter of approximately 10-13.5 mm and an outer diameter of approximately 12-15.5 mm, so as to be readily slidable over a conventional endoscope. Preferably, sleeve 438 is configured for mounting over endoscopes of various diameters, such as in the range of 9.5-13 mm.

It is appreciated that sleeve 438 is relatively flexible, thereby being able to conform to bending of the endoscope onto which it is slidably mounted, and is yet sufficiently rigid so as to allow its sliding over the endoscope by pushing it forward at a rearward end thereof.

Sleeve 438 may be formed of any suitable material such as silicone, PEBAX®, PVC or polyurethane. In accordance with a preferred embodiment of the present invention, the inner surface of sleeve 438 is formed of a low-friction material, such as thin and flexible internal TEFLON® tube or a hydrophilic coating, so as to allow low resistance sliding of sleeve 438 over an endoscope in a bent orientation.

Figure 10:
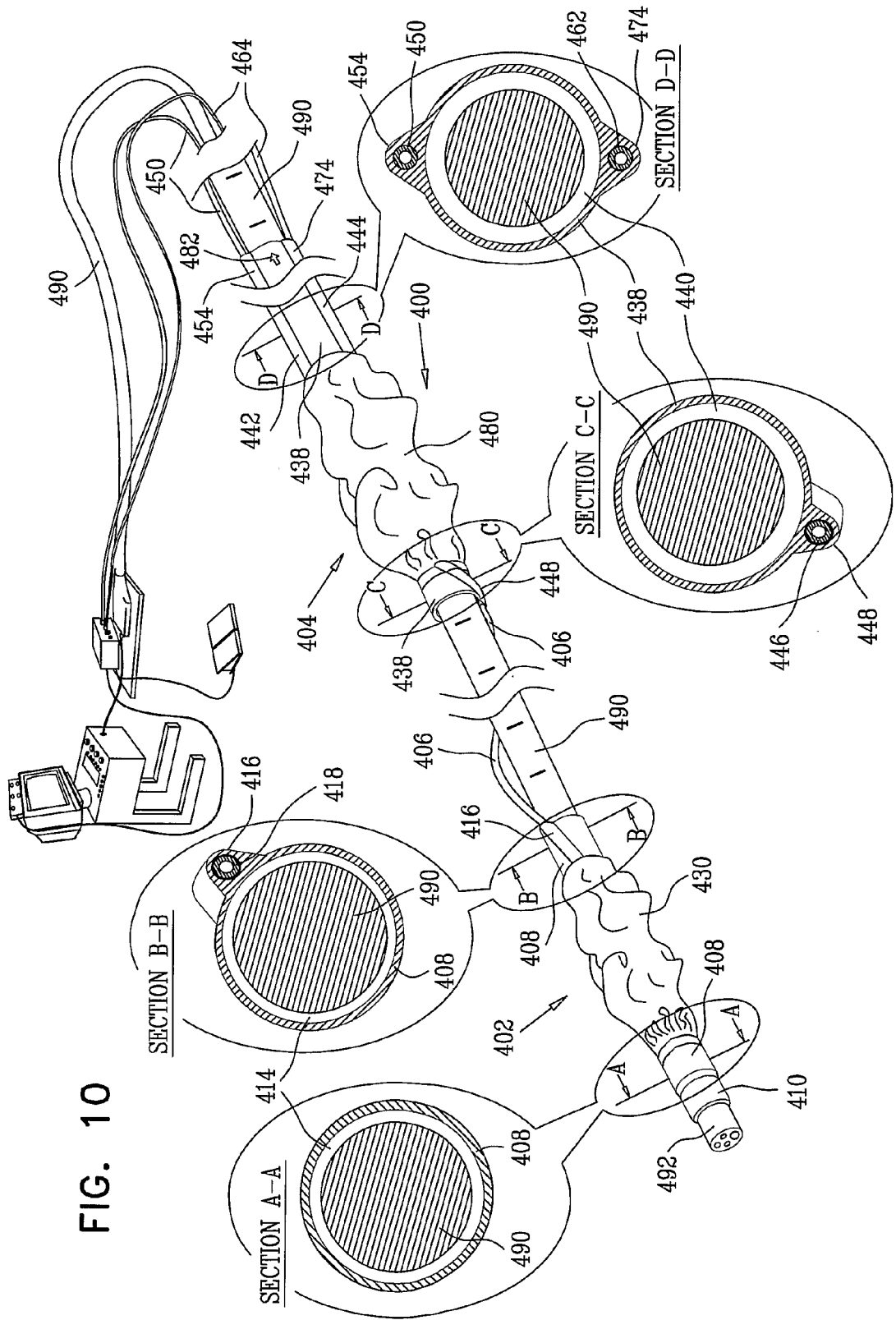
FIG. 10 is a simplified pictorial illustration of the double balloon device of FIG. 9, mounted on a conventional endoscope assembly.

Reference is now made to FIG. 10, which is a simplified pictorial illustration of the double balloon device of FIG. 9, mounted on a conventional endoscope 490 forming part of a conventional endoscope system. Endoscope 490 may be identical to endoscope 302 described hereinabove.

In practice, initially the rearward endoscope-mountable inflatable balloon assembly 404 is slid over a forward end 492 of endoscope 490 in the manner of a conventional overtube. Thereafter the forward endoscope-mountable inflatable balloon assembly 402 is fitted onto the endoscope with collar 410 being snugly mounted adjacent the forward end 492 of endoscope 490 preferably by using the device 100 described hereinabove with reference to FIGS. 1-7N and 8A-8N.

Operation of the double balloon device 400 may be identical or similar to that of a commercially available double-balloon endoscope, such as a double balloon endoscope assembly including EN-450T5 enteroscope, TS-13140 overtube and BS-2 front balloon, which interface with balloon pump control BP-20 and 2200 video system, all commercially available from Fujinon Inc., of 10 High Point Drive, Wayne, N.J., USA.

Disengagement of the double balloon device 400 from endoscope 490 following use, may be readily achieved by using the collar cutting tool 330 described hereinabove with reference to FIGS. 7O-7Q and 8O-8P.

Figure 11B:
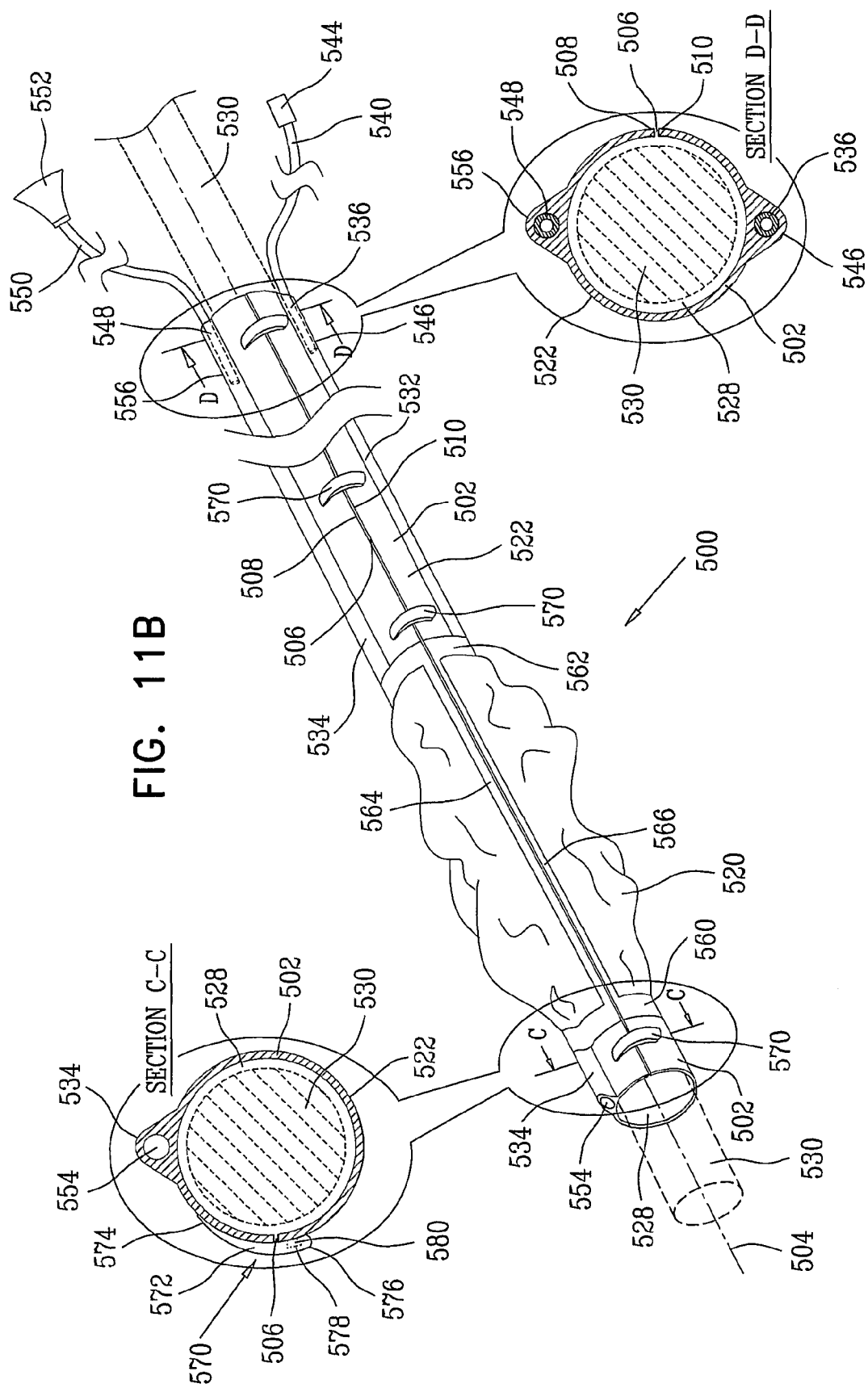
Figure 12:
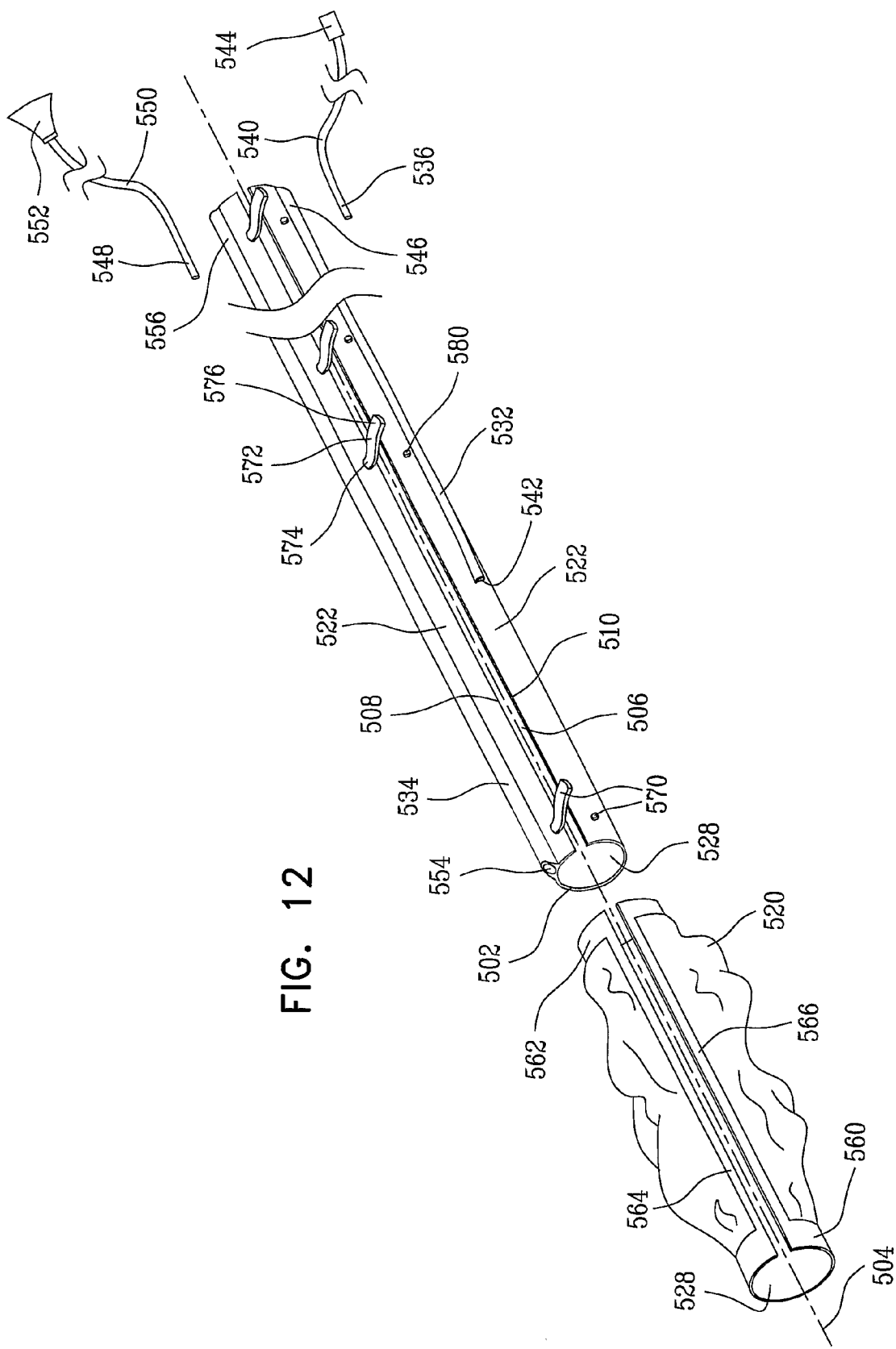
FIG. 12 is a simplified exploded pictorial illustration of the endoscope overtube of FIGS. 11A & 11B.
Figure 13A:
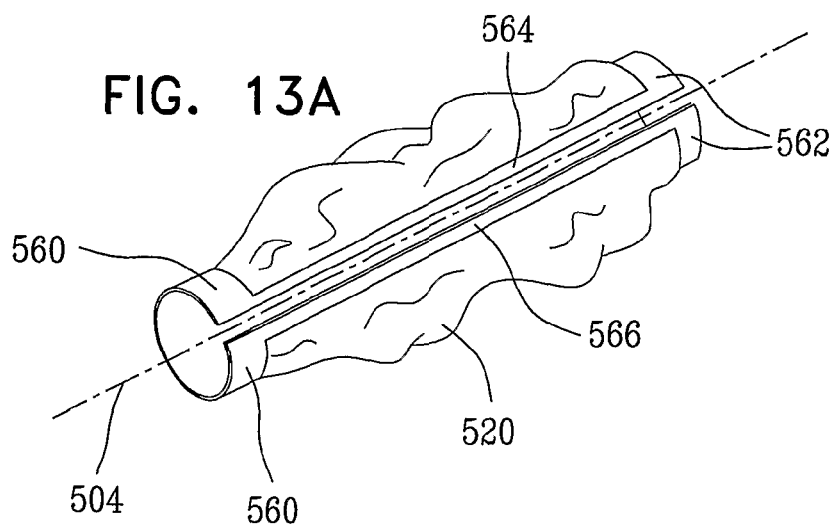
FIGS. 13A, 13B and 13C are respective simplified pictorial, end view and side view illustrations of a balloon employed in the endoscope overtube of FIGS. 11A-12.
Figure 13B:
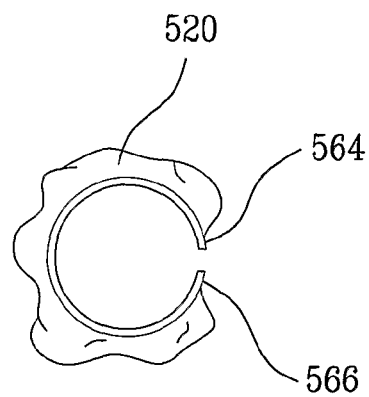
Figure 13C:
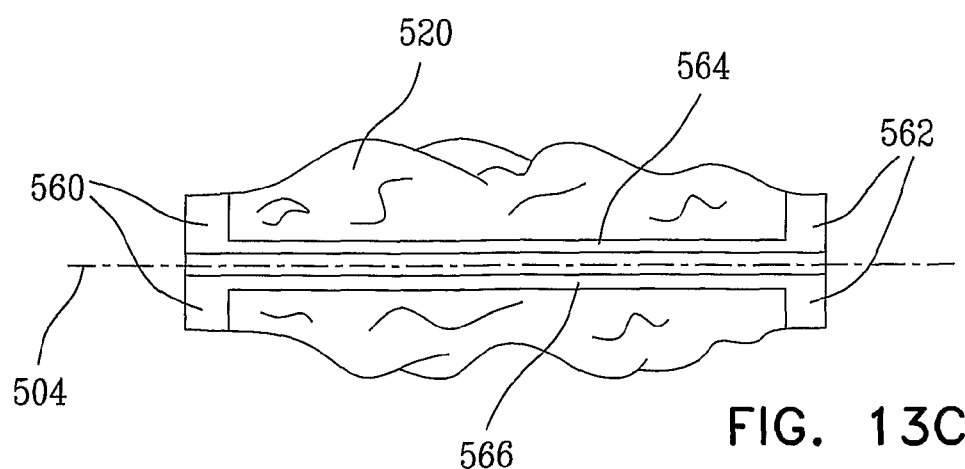

Reference is now made to FIGS. 11A & 11B, which are simplified pictorial illustrations of an endoscope overtube constructed and operative in accordance with a preferred embodiment of the present invention in respective open and closed orientations; FIG. 12, which is a simplified exploded pictorial illustration of the endoscope overtube of FIGS. 11A & 11B and FIGS. 13A, 13B & 13C, which are respective simplified pictorial, end view and side view illustrations of a balloon employed in the endoscope overtube of FIGS. 11A-12.

As seen in FIGS. 11A-12, there is provided an endoscope overtube 500 constructed and operative in accordance with a preferred embodiment of the present invention including a generally non axially compressible, tubular generally cylindrical sleeve 502 arranged about a longitudinal axis 504. Sleeve 502 is preferably slit axially, as indicated by reference numeral 506, thus defining axial slit edges 508 and 510 and thus is circumferentially expandable and compressible. A selectably inflatable/deflatable balloon 520 is mounted over part of an outer surface 522 of sleeve 502.

Sleeve 502 preferably has a main lumen 528 for accommodating an endoscope 530, which may be similar to endoscope 302 described hereinabove, and first and second side lumens 532 and 534 which are circumferentially spaced from each other along outer surface 522 of sleeve 502.

First side lumen 532 accommodates a forward portion 536 of a flexible balloon inflation/deflation tube 540 and extends partially along the length of sleeve 502, outwardly of main lumen 528, to an opening 542 underlying and in fluid communication with the interior of balloon 520. Preferably, flexible tube 540 extends from a connector 544 outside of sleeve 502 and forward portion 536 thereof extends partially along and inside a rearward-facing portion 546 of first side lumen 532 and is fixedly and sealingly attached thereto as by a suitable adhesive, so as to provide a sealed inflation/deflation pathway therewith.

Second side lumen 534 accommodates a forward portion 548 of a flexible instrument channel tube 550 which extends from a tool insertion port 552 outside of sleeve 502. Second side lumen 534 extends along the entire length of sleeve 502, along outer surface 522 thereof and underlying balloon 520 from a rear edge of sleeve 502 to an open end 554. Instrument channel tube 550 extends from port 552, partially along and inside a rearward facing portion 556 of second side lumen 534 and is fixedly attached thereto as by a suitable adhesive.

Balloon 520 is preferably a preformed, flexible element, having a generally cylindrical configuration when assembled onto sleeve 502 and securely mounted onto endoscope 530 (FIG. 11B). Balloon 520 includes peripheral sealing surfaces which are preferably adhesively joined or heat welded onto outer surface 522 of sleeve 502. The peripheral sealing surfaces preferably include respective forward and rearward circumferential collar sealing surfaces 560 and 562 and first and second axial sealing surfaces 564 and 566 which extend parallel to slit edges 508 and 510.

It is appreciated that the generally axial slit 506 of sleeve 502 may be straight or curved, such as a straight slit parallel to longitudinal axis 504, a spiral slit along longitudinal axis 504, or a sinusoidal slit. The forward edge of sleeve 502 is preferably smooth and rounded so as to avoid damage to tissue under examination during in vivo inspection of a generally tubular body portion such as the intestine.

Preferably, sleeve 502 is of a typical length of approximately 100-160 cm and has an inner diameter of approximately 10-13.5 mm and an outer diameter of approximately 12-15.5 mm, so as to be readily slidable over a conventional endoscope. Preferably, sleeve 502 is configured for mounting over endoscopes of various diameters, such as in the range of 9.5-13 mm. Yet preferably, the thickness of sleeve 502 is in the range of 0.3-2 mm, and may be constant or varying along its length.

In accordance with a preferred embodiment of the present invention, the forward portion of sleeve 502 underlying balloon 520 is relatively rigid, thereby not allowing inward expansion of sleeve 502 during inflation of balloon 520, so as to allow slidable motion of endoscope 530 through sleeve 502 when balloon 520 is inflated. Alternatively, the forward portion of sleeve 502 underlying balloon 520 is highly flexible, thereby allowing inward expansion of sleeve 502 during inflation of balloon 520, so as to engage endoscope 530 and fix its position relative to sleeve 502 when balloon 520 is inflated, thereby preventing slidable motion therebetween.

It is appreciated that sleeve 502 is relatively flexible, thereby being able to conform to bending of endoscope 530 onto which it is slidably mounted, and is yet sufficiently rigid so as to allow its sliding over endoscope 530 by pushing it forward at a rearward end thereof. Sleeve 502 may be formed of any suitable material such as silicone, PEBAX®, PVC or polyurethane. In accordance with a preferred embodiment of the present invention, the inner surface of sleeve 502 is formed of a low-friction material, such as thin and flexible internal TEFLON® tube or a hydrophilic coating, so as to allow low resistance sliding of sleeve 502 over an endoscope in a bent orientation.

It is appreciated that in accordance with a preferred embodiment of the present invention balloon 520 is generally inflatable, and can be inflated to a diameter about 3-10 times larger than its diameter when not inflated. In accordance with a preferred embodiment of the present invention, useful for small intestine endoscopy, the diameter of balloon 520 when fully inflated is in the range of 35-45 mm. Preferably, inflation of balloon 520 to a diameter less than 45 mm may be achieved using relatively low pressure, such as in the range of 20-40 millibars.

In another specific embodiment, useful for large intestine endoscopy, the diameter of balloon 520, when fully inflated, is in the range of 4-6 centimeters. In a further embodiment, also useful for large intestine endoscopy, the diameter of balloon 520, when fully inflated, is six centimeters. Preferably, inflation of balloon 520 to a diameter less than six centimeters may be achieved using relatively low pressure, such as in the range of 20-40 millibars.

It is appreciated that in accordance with a preferred embodiment of the present invention, useful for in vivo inspection of a generally tubular body portion having a variable cross-sectional diameter, the expansion diameter range of balloon 520, when mounted onto sleeve 502, is larger than the maximum cross-sectional diameter of the generally tubular body portion, thereby enabling engagement of expanded balloon 520 with the interior surface of the generally tubular body portion, and anchoring of sleeve 502 thereto. Preferably, balloon 520 is a relatively soft, highly compliant balloon, operative to at least partially conform to the shape of the interior surface of the generally tubular body portion when in engagement therewith.

It is appreciated that balloon 520 may be formed of suitable well-known stretchable materials such as latex, flexible silicone, or highly flexible nylon. Alternatively, balloon 520 may be formed of polyurethane, which is less stretchable and conforming than latex, flexible silicone or highly flexible nylon. Preferably, the diameter of balloon 520 is sufficient to ensure tight anchoring at any part of the generally tubular body portion. Alternatively, balloon 520 may be obviated. A plurality of latches 570 are provided for selectably securely mounting overtube 500 onto endoscope 530 and are distributed along the length of overtube 500 other than underlying balloon 520. These latches preferably each include an arm portion 572, which is joined at one end 574 thereof, to outer surface 522 of sleeve 502 adjacent one of edges 508 and 510 of slit 506 as by adhesive or heat welding. At an opposite end 576 of each arm there is provided a first attachment portion 578 which removably engages a corresponding second attachment portion 580 mounted adjacent an opposite one of edges 508 and 510. In the illustrated embodiment, the arm portions 572 are attached adjacent edges 508 and the first attachment portion 578 is a recess which mates with a corresponding protrusion defining the second attachment portion 580. Any other suitable arrangement may be employed.

Reference is now made to FIGS. 14A, 14B, 14C, 14D and 14E, which are simplified illustrations of association of the endoscope overtube of FIGS. 11A-12 with a conventional endoscope and a conventional endoscope tool.

Figure 14A:
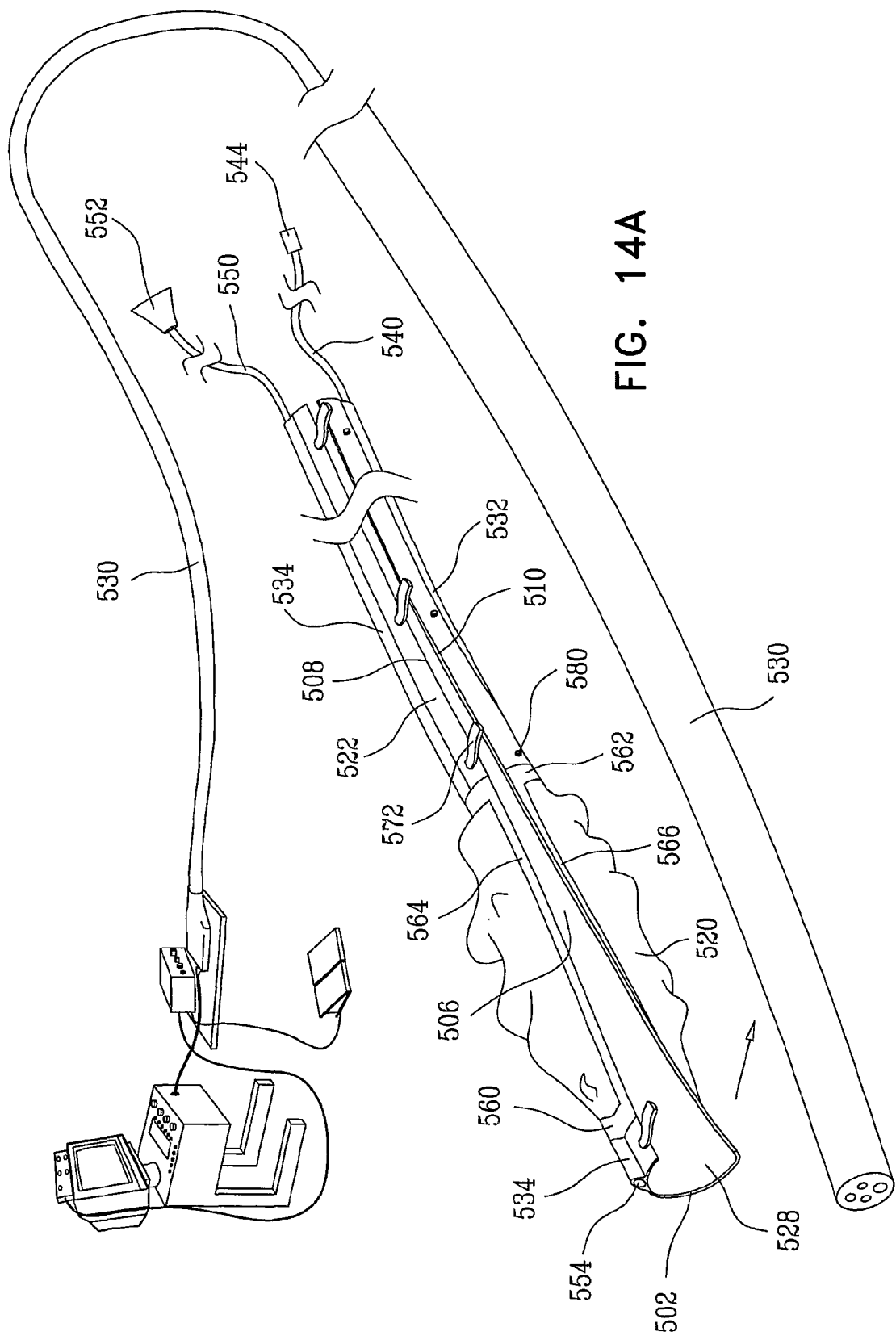
FIGS. 14A, 14B, 14C, 14D and 14E are simplified illustrations of association of the endoscope overtube of FIGS. 11A-12 with a conventional endoscope and a conventional endoscope tool.

FIG. 14A shows the overtube 500 of FIGS. 11A-12 about to be mounted on an endoscope 530 forming part of a conventional endoscope system. The endoscope system may comprise, for example, a conventional endoscope such as a VSB-3430K video enteroscope or a EC-3470LK video colonoscope, which are connectable to an endoscopy console such as a console including a EPK-1000 video processor and a SONY LMD-2140MD medical grade flat panel LCD monitor, all commercially available from Pentax Europe GmbH, 104 Julius-Vosseler St., 22527 Hamburg, Germany. It is seen that a forward part of overtube 500 is in an expanded open orientation such that slit 506 can accommodate the thickness of endoscope 530.

Figure 14B:
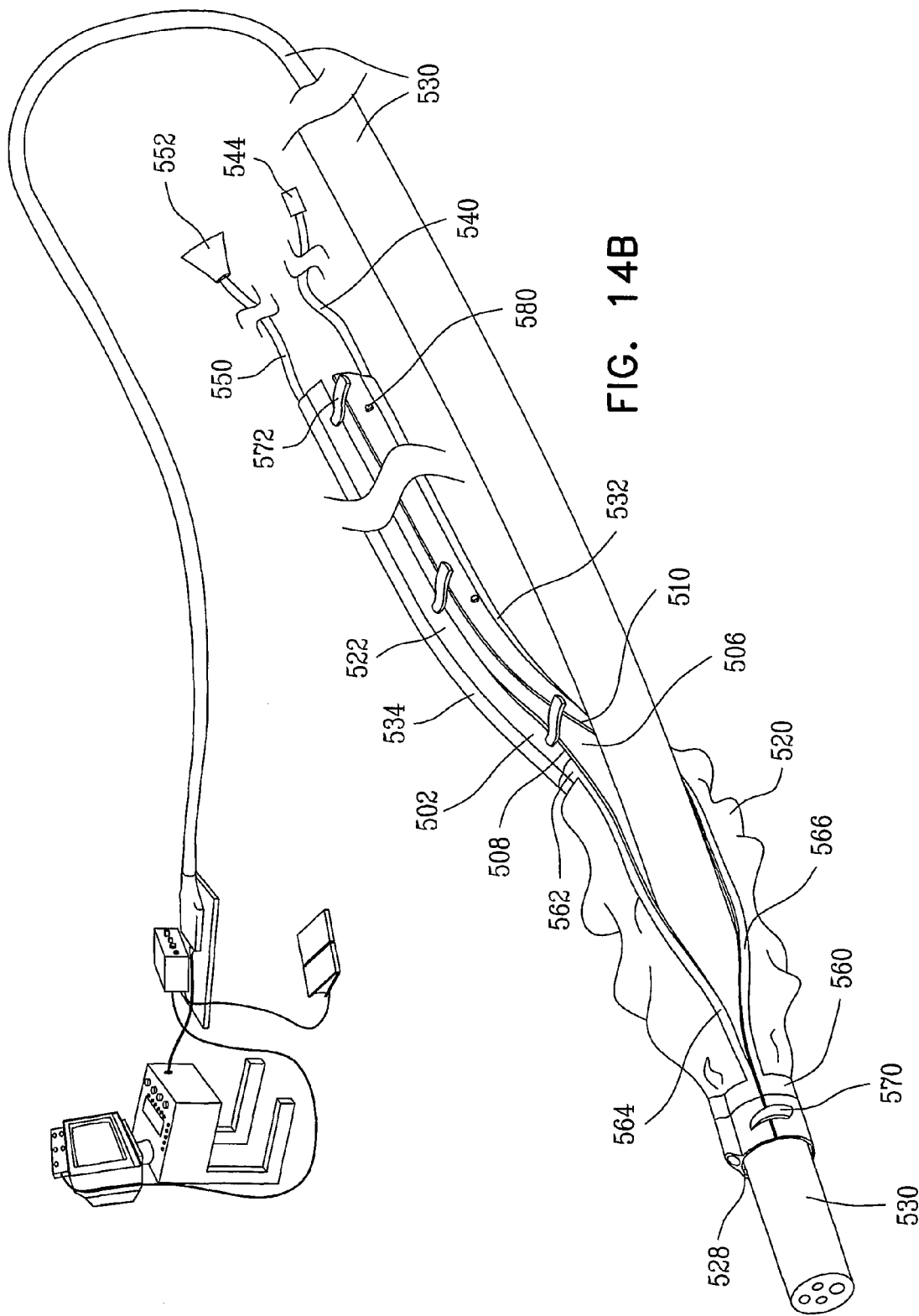
Figure 14C:
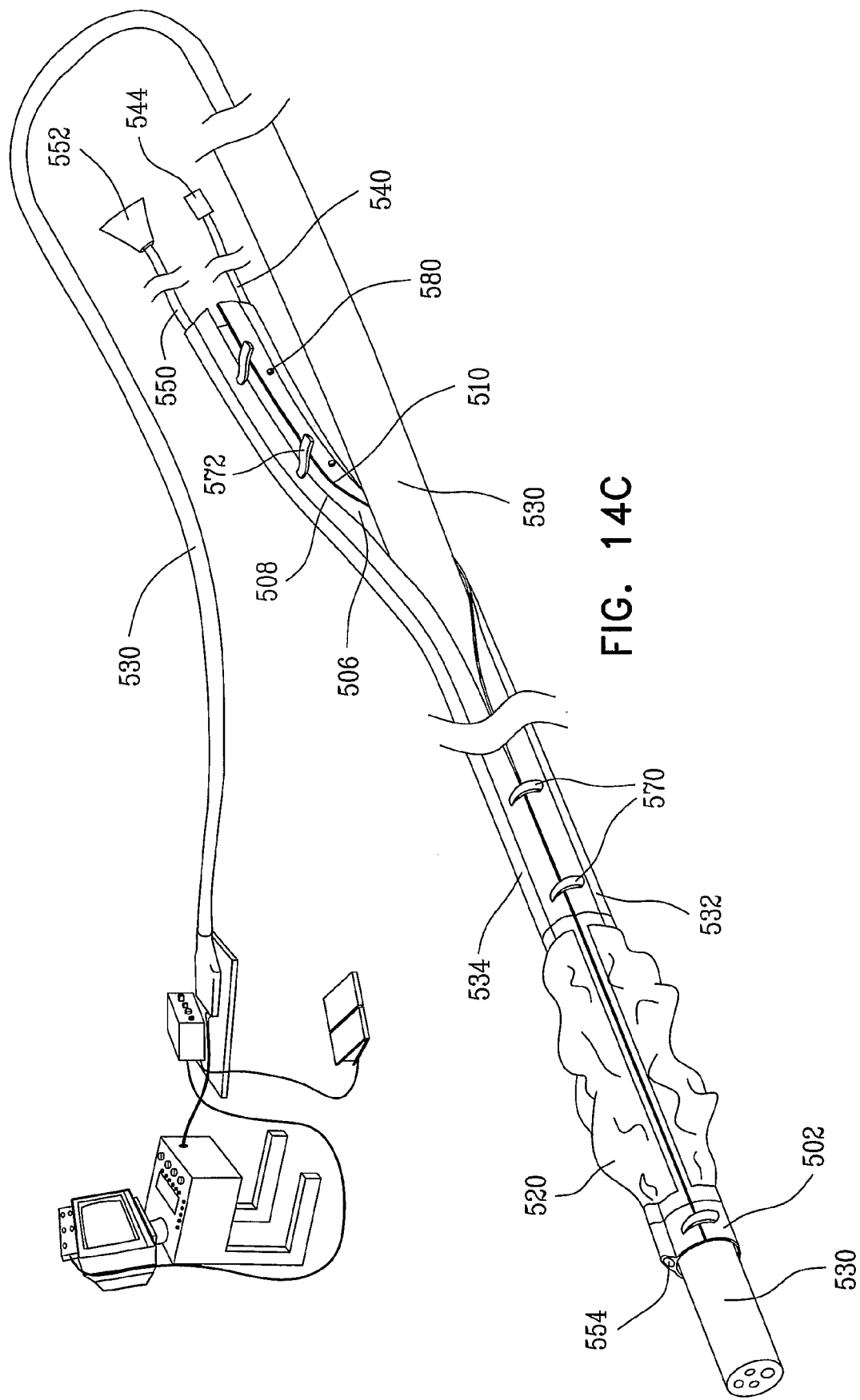
Figure 14D:
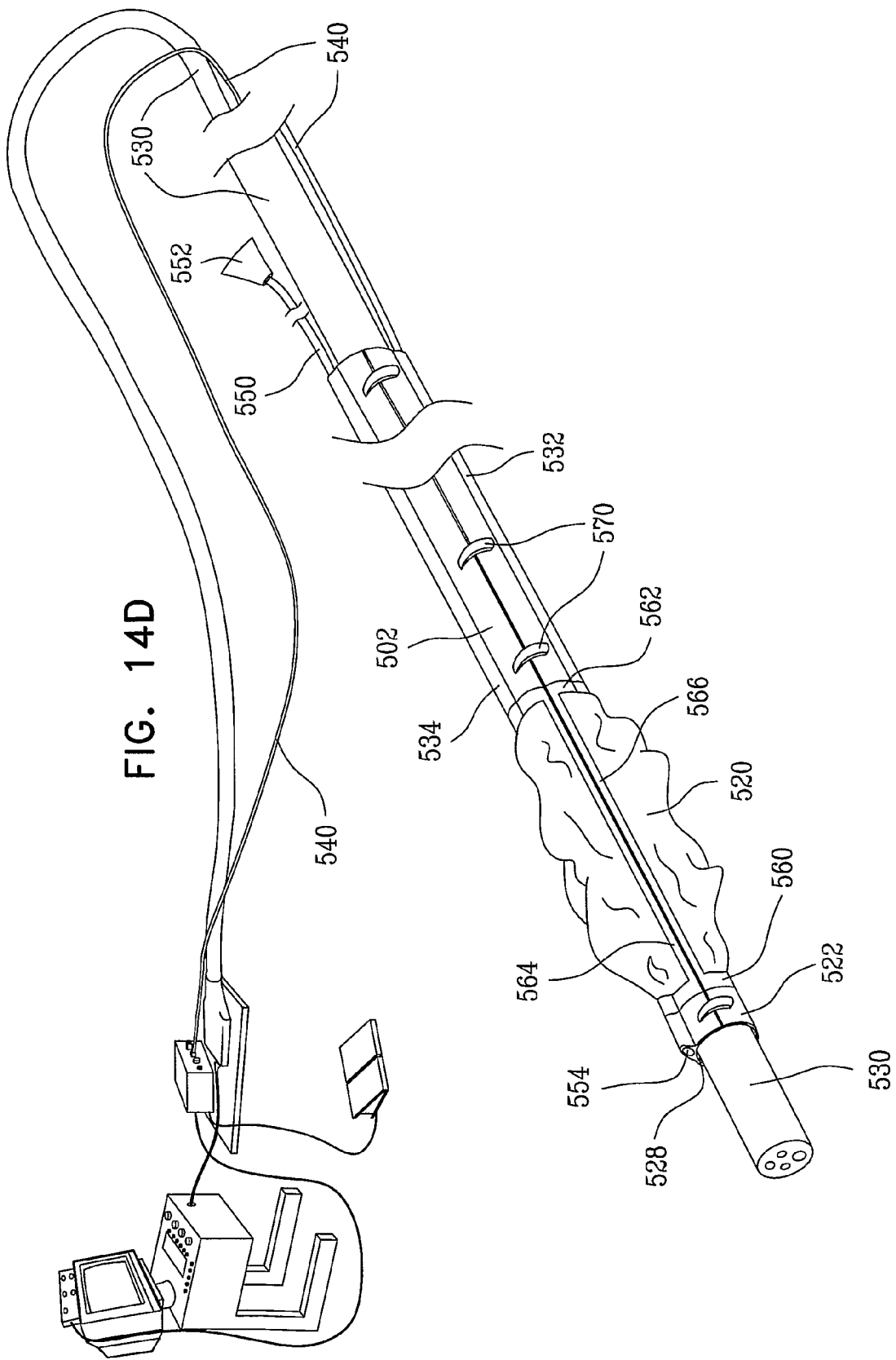
Figure 14E:
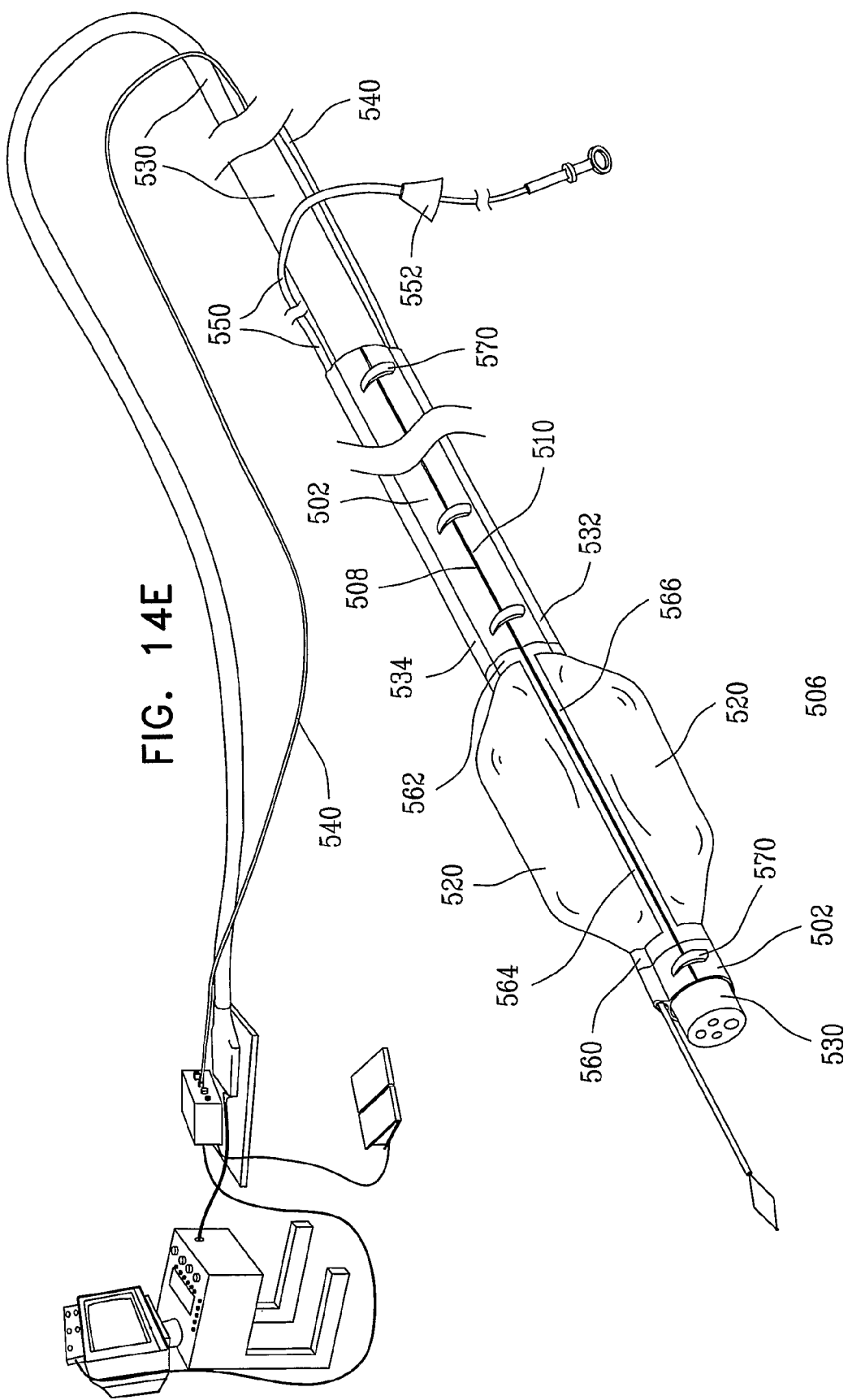

FIG. 14B shows a most forward part of overtube 500, including part of balloon 520, latched in secure engagement with endoscope 530. FIG. 14C shows more of overtube 500, including all of balloon 520, latched in secure engagement with endoscope 530. FIG. 14D shows all of overtube 500, latched in secure engagement with endoscope 530. FIG. 14E illustrates the general configuration of balloon 520 when inflated and the insertion of a conventional endoscope tool through the instrument channel, defined by port 552, tube 550 and second side lumen 534, which is preferably a low friction lumen comprising a flexible internal TEFLON® tube, a hydrophilic coating, or any alternative suitable low friction lumen.

It will be appreciated by persons skilled in the art that the present invention is not limited by what has been particularly shown and described herein above. Rather the scope of the present invention includes both combinations and subcombinations of the various features described hereinabove as well as variations and modifications which would occur to persons skilled in the art upon reading the specifications and which are not in the prior art.

The invention claimed is:

1. An expander for mounting a resilient outer tubular article over an elongate article comprising:
   a chassis element having a generally circular cylindrical bore defined therein, said chassis element having associated therewith at least one outwardly movable element which is selectably engageable with at least a portion of said resilient outer tubular article, said at least one outwardly movable element having a radially contracted state and a radially expanded state;
   a driver having a connector portion at a forward end thereof, said driver being movable with respect to said chassis element and being operative to selectably engage said at least one outwardly movable element, when said outwardly movable element is in engagement with said at least a portion of said resilient outer tubular article, for producing corresponding outward motion and outward expansion thereof; and
   an engagement element which is removably connectable to said connector portion forwardly of said driver, for insertion into said at least a portion of said resilient outer tubular article upon expansion thereof by operation of said driver, said engagement element being insertable into said generally circular cylindrical bore of said chassis element when said at least one outwardly movable element is in said radially contracted state and being configured to accommodate at least a portion of said elongate article.

2. An expander according to claim 1 and wherein said expander is configured to disengage said at least a portion of said resilient outer tubular article from said engagement element.

3. An expander according to claim 2 and wherein said chassis element is configured to disengage said at least a portion of said resilient outer tubular article from said engagement element.

4. An expander according to claim 2 and wherein said expander is configured to disengage said at least a portion of said resilient outer tubular article from said engagement element by sliding said at least a portion of said resilient outer tubular article relative to said engagement element.

5. An expander according to claim 1 and wherein said expander is operative for mounting said resilient outer tubular article over said elongate article at a generally predetermined distance from a forward end thereof.

6. An expander according to claim 1 and wherein said engagement element is adapted for accommodating said at least a portion of said elongate article up to a predetermined length thereof.

7. An expander according to claim 1 and wherein said engagement element is generally smaller then said chassis element.

8. An expander according to claim 1 and wherein said driver is axially movable with respect to said chassis element.

* * * * *